(12) United States Patent
Bäuerle et al.

(10) Patent No.: US 7,964,707 B2
(45) Date of Patent: Jun. 21, 2011

(54) ANTI-IL2 ANTIBODIES

(75) Inventors: Patrick Bäuerle, Gauting (DE); John Lumsden, München (DE); Stefan Pflanz, Redwood City, CA (US); Tobias Raum, München (DE); Jörg Volkland, Neuried (DE)

(73) Assignee: Micromet AG, Munich (DE)

( * ) Notice: Subject to any disclaimer, the term of this patent is extended or adjusted under 35 U.S.C. 154(b) by 398 days.

(21) Appl. No.: 11/916,017

(22) PCT Filed: May 31, 2006

(86) PCT No.: PCT/EP2006/005194
§ 371 (c)(1),
(2), (4) Date: Aug. 27, 2008

(87) PCT Pub. No.: WO2006/128690
PCT Pub. Date: Dec. 7, 2006

(65) Prior Publication Data
US 2008/0317746 A1     Dec. 25, 2008

(30) Foreign Application Priority Data

Jun. 1, 2005   (EP) .................................. 05011845

(51) Int. Cl.
*C12P 21/08*   (2006.01)
*C07K 16/00*   (2006.01)
*A61K 39/00*   (2006.01)
*A61K 39/395*  (2006.01)

(52) U.S. Cl. ............... 530/388.1; 530/387.1; 530/387.3; 530/388.23; 424/133.1; 424/141.1; 424/145.1

(58) Field of Classification Search .......................... None
See application file for complete search history.

(56) References Cited

U.S. PATENT DOCUMENTS 7,439,041 B2 * 10/2008 Michelitsch et al. ........ 435/69.3
2002/0151682 A1 * 10/2002 Athwal et al. ............... 530/350

FOREIGN PATENT DOCUMENTS

WO    WO 01/90193    11/2001

OTHER PUBLICATIONS

Skolnick and Fetrow. From genes to protein structure and function: novel applications of computational approaches in the genomic era. Trends in Biotechnology, 2000. vol. 18, pp. 34-39.*

Mac Callum, Martin, and Thornton. Antibody-antigen interactions: contact analysis and binding site topography. Journal of Molecular Biology, 1996. vol. 262, pp. 732-745.*

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*

Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*

Wu, Nie, Huse, and Watkins. Humanization of a murine monoclonal antibody by simultaneous optimization of framework and CDR residues. Journal of Molecular Biology, 1999. vol. 294, pp. 151-162.*

Kircher et al., "Comparative in vitro study of the immunomodulatory activity of humanized and chimeric anti-CD25 monoclonal antibodies," *Clinical and Experimental Immunol.*, 134:426-430, 2003.

Nussenblatt et al., "Treatment of noninfectious intermediate and posterior uveitis with the humanized anti-Tac mAb: a phase I/II clinical trial," *Proc. Natl. Acad. Sci. USA*, 96:7462-7466, 1999.

Raum et al., "Anti-self antibodies selected from a human IgD heavy chain repertoire: a novel approach to generate therapeutic human antibodies against tumor-associated differentiation antigens," *Cancer Immunol. Immunother.*, 50:141-150, 2001.

Setoguchi et al., "Homeostatic maintenance of natural Foxp3(+) CD25(+) CD4(+) regulatory T cells by interleukin (IL)-2 and induction of autoimmune disease by IL-2 neutralization," *J. Exp. Med.*, 201:723-735, 2005.

Waldmann et al., "Contrasting Roles of IL-2 and IL-15 in the Life and Death of Lymphocytes: Implications for Immunotherapy," *Immunity*, 14:105-110, 2002.

Waldmann, "The contrasting roles of IL-2 and IL-15 in the life and death of lymphocytes: implications for the immunotherapy of rheumatological diseases," *Arthritis Res.*, 4:S161-S167, 2002.

Waldmann, "The IL-2/IL-15 receptor systems: targets for immunotherapy," *J. Clin. Immunol.*, 22:51-56, 2002.

Hooks et al., "Identification of the lymphokines, interferon-gamma and interleukin-2, in inflammatory eye diseases," *Investigative Ophthalmology & Visual Science*, 29(6):1444-1451, 1988.

\* cited by examiner

*Primary Examiner* — Anne M. Gussow
(74) *Attorney, Agent, or Firm* — Fulbright & Jaworski

(57) ABSTRACT

The invention relates to a humanized monoclonal antibody or fragment thereof which specifically binds to human interlukin-2 (IL2), whereby said humanized monoclonal antibody neutralizes the activity of human IL2 by binding to the human IL2 prior to, during, and/or subsequent to the binding of the human IL2 to the human IL2-receptor, and wherein the light chain variable region of the humanized monoclonal antibody comprises in its second framework region the contiguous amino acid sequence KAPKA at amino acid positions 42-46.

19 Claims, 18 Drawing Sheets

Fig. 7a

Figure 1:
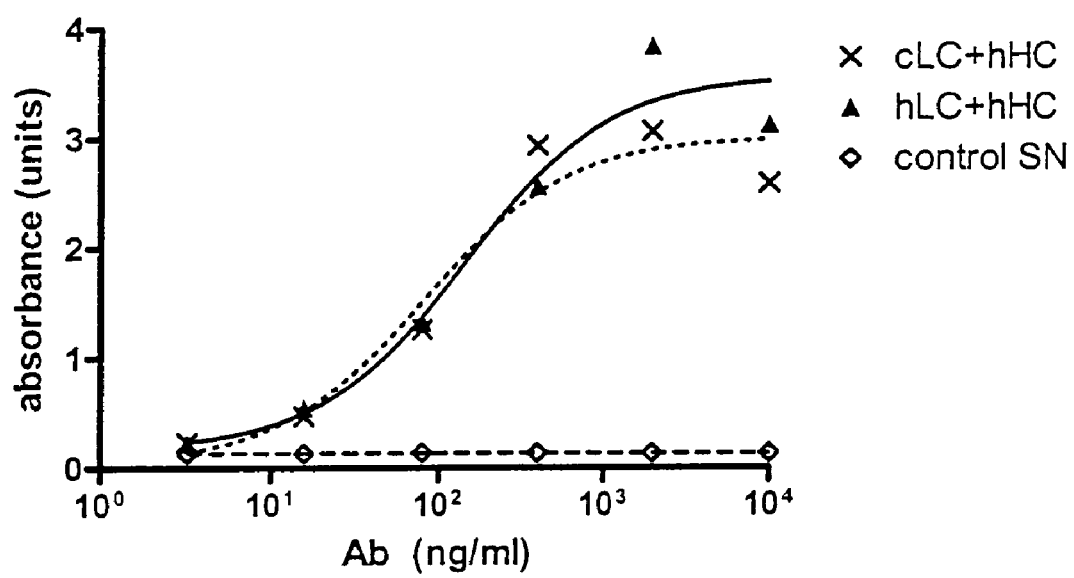

| | | FR1 | | | FR2 | | |
|---|---|---|---|---|---|---|---|
| | | 1 | 2 | SEQ NO: | 3 | 4 | SEQ NO: |
| | Locus | 12345678901234567890123 | | | 567890123456789 | | |
| VKI | O12 | DIQMTQSPSSLSASVGDRVTITC | | 40 | WYQQKPGKAPKLLIY | | 41 |
| | O2 | DIQMTQSPSSLSASVGDRVTITC | | 40 | WYQQKPGKAPKLLIY | | 41 |
| | O18 | DIQMTQSPSSLSASVGDRVTITC | | 40 | WYQQKPGKAPKLLIY | | 41 |
| | O8 | DIQMTQSPSSLSASVGDRVTITC | | 40 | WYQQKPGKAPKLLIY | | 41 |
| | A20 | DIQMTQSPSSLSASVGDRVTITC | | 40 | WYQQKPGKVPKLLIY | | 42 |
| | A30 | DIQMTQSPSSLSASVGDRVTITC | | 40 | WYQQKPGKAPKRLIY | | 43 |
| | L14 | NIQMTQSPSAMSASVGDRVTITC | | 44 | WFQQKPGKVPKHLIY | | 45 |
| | L1 | DIQMTQSPSSLSASVGDRVTITC | | 40 | WFQQKPGKAPKSLIY | | 46 |
| | L15 | DIQMTQSPSSLSASVGDRVTITC | | 40 | WYQQKPEKAPKSLIY | | 47 |
| | L4 | AIQLTQSPSSLSASVGDRVTITC | | 48 | WYQQKPGKAPKLLIY | | 41 |
| | L18 | AIQLTQSPSSLSASVGDRVTITC | | 48 | WYQQKPGKAPKLLIY | | 41 |
| | L5 | DIQMTQSPSSVSASVGDRVTITC | | 49 | WYQQKPGKAPKLLIY | | 41 |
| | L19 | DIQMTQSPSSVSASVGDRVTITC | | 49 | WYQQKPGKAPKLLIY | | 41 |
| | L8 | DIQLTQSPSFLSASVGDRVTITC | | 50 | WYQQKPGKAPKLLIY | | 41 |
| | L23 | AIRMTQSPFSLSASVGDRVTITC | | 51 | WYQQKPAKAPKLFIY | | 52 |
| | L9 | AIRMTQSPSSFSASTGDRVTITC | | 53 | WYQQKPGKAPKLLIY | | 41 |
| | L24 | VIWMTQSPSLLSASTGDRVTISC | | 54 | WYQQKPGKAPELLIY | | 55 |
| | L11 | AIQMTQSPSSLSASVGDRVTITC | | 56 | WYQQKPGKAPKLLIY | | 41 |
| | L12 | DIQMTQSPSTLSASVGDRVTITC | | 57 | WYQQKPGKAPKLLIY | | 41 |
| VKII | O11 | DIVMTQTPLSLPVTPGEPASISC | | 58 | WYLQKPGQSPQLLIY | | 59 |
| | O1 | DIVMTQTPLSLPVTPGEPASISC | | 58 | WYLQKPGQSPQLLIY | | 59 |
| | A17 | DVVMTQSPLSLPVTLGQPASISC | | 60 | WFQQRPGQSPRRLIY | | 61 |
| | A1 | DVVMTQSPLSLPVTLGQPASISC | | 60 | WFQQRPGQSPRRLIY | | 61 |
| | A18 | DIVMTQTPLSLSVTPGQPASISC | | 62 | WYLQKPGQSPQLLIY | | 59 |
| | A2 | DIVMTQTPLSLSVTPGQPASISC | | 62 | WYLQKPGQPPQLLIY | | 63 |
| | A19 | DIVMTQSPLSLPVTPGEPASISC | | 64 | WYLQKPGQSPQLLIY | | 59 |
| | A3 | DIVMTQSPLSLPVTPGEPASISC | | 64 | WYLQKPGQSPQLLIY | | 59 |
| | A23 | DIVMTQTPLSSPVTLGQPASISC | | 65 | WLQQRPGQPPRLLIY | | 66 |
| VKIII | A27 | EIVLTQSPGTLSLSPGERATLSC | | 67 | WYQQKPGQAPRLLIY | | 68 |
| | A11 | EIVLTQSPATLSLSPGERATLSC | | 69 | WYQQKPGLAPRLLIY | | 70 |
| | L2 | EIVMTQSPATLSVSPGERATLSC | | 71 | WYQQKPGQAPRLLIY | | 68 |
| | L16 | EIVMTQSPATLSVSPGERATLSC | | 71 | WYQQKPGQAPRLLIY | | 68 |
| | L6 | EIVLTQSPATLSLSPGERATLSC | | 69 | WYQQKPGQAPRLLIY | | 68 |
| | L20 | EIVLTQSPATLSLSPGERATLSC | | 69 | WYQQKPGQAPRLLIY | | 68 |
| | L25 | EIVMTQSPATLSLSPGERATLSC | | 72 | WYQQKPGQAPRLLIY | | 68 |
| VKIV | B3 | DIVMTQSPDSLAVSLGERATINC | | 73 | WYQQKPGQPPKLLIY | | 74 |
| VKV | B2 | ETTLTQSPAFMSATPGDKVNISC | | 75 | WYQQKPGEAAIFIIQ | | 76 |
| VKVI | A26 | EIVLTQSPDFQSVTPKEKVTITC | | 77 | WYQQKPDQSPKLLIK | | 78 |
| | A10 | EIVLTQSPDFQSVTPKEKVTITC | | 77 | WYQQKPDQSPKLLIK | | 78 |
| | A14 | DVVMTQSPAFLSVTPGEKVTITC | | 79 | WYQQKPDQAPKLLIK | | 80 |

Fig. 7b

|  |  | FR3 |  |
|---|---|---|---|
|  |  | 5  6     7     8 | SEQ NO: |
|  | Locus | 7890123456789012345678901 2345678 |  |
| VKI | O12 | GVPSRFSGSGSGTDFTLTISSLQPEDFATYYC | 81 |
|  | O2 | GVPSRFSGSGSGTDFTLTISSLQPEDFATYYC | 81 |
|  | O18 | GVPSRFSGSGSGTDFTFTISSLQPEDIATYYC | 82 |
|  | O8 | GVPSRFSGSGSGTDFTFTISSLQPEDIATYYC | 82 |
|  | A20 | GVPSRFSGSGSGTDFTLTISSLQPEDVATYYC | 83 |
|  | A30 | GVPSRFSGSGSGTEFTLTISSLQPEDFATYYC | 84 |
|  | L14 | GVPSRFSGSGSGTEFTLTISSLQPEDFATYYC | 84 |
|  | L1 | GVPSRFSGSGSGTDFTLTISSLQPEDFATYYC | 81 |
|  | L15 | GVPSRFSGSGSGTDFTLTISSLQPEDFATYYC | 81 |
|  | L4 | GVPSRFSGSGSGTDFTLTISSLQPEDFATYYC | 81 |
|  | L18 | GVPSRFSGSGSGTDFTLTISSLQPEDFATYYC | 81 |
|  | L5 | GVPSRFSGSGSGTDFTLTISSLQPEDFATYYC | 81 |
|  | L19 | GVPSRFSGSGSGTDFTLTISSLQPEDFATYYC | 81 |
|  | L8 | GVPSRFSGSGSGTEFTLTISSLQPEDFATYYC | 84 |
|  | L23 | GVPSRFSGSGSGTDYTLTISSLQPEDFATYYC | 85 |
|  | L9 | GVPSRFSGSGSGTDFTLTISCLQSEDFATYYC | 86 |
|  | L24 | GVPSRFSGSGSGTDFTLTISCLQSEDFATYYC | 86 |
|  | L11 | GVPSRFSGSGSGTDFTLTISSLQPEDFATYYC | 81 |
|  | L12 | GVPSRFSGSGSGTEFTLTISSLQPDDFATYYC | 87 |
| VKII | O11 | GVPDRFSGSGSGTDFTLKISRVEAEDVGVYYC | 88 |
|  | O1 | GVPDRFSGSGSGTDFTLKISRVEAEDVGVYYC | 88 |
|  | A17 | GVPDRFSGSGSGTDFTLKISRVEAEDVGVYYC | 88 |
|  | A1 | GVPDRFSGSGSGTDFTLKISRVEAEDVGVYYC | 88 |
|  | A18 | GVPDRFSGSGSGTDFTLKISRVEAEDVGVYYC | 88 |
|  | A2 | GVPDRFSGSGSGTDFTLKISRVEAEDVGVYYC | 88 |
|  | A19 | GVPDRFSGSGSGTDFTLKISRVEAEDVGVYYC | 88 |
|  | A3 | GVPDRFSGSGSGTDFTLKISRVEAEDVGVYYC | 88 |
|  | A23 | GVPDRFSGSGAGTDFTLKISRVEAEDVGVYYC | 89 |
| VKIII | A27 | GIPDRFSGSGSGTDFTLTISRLEPEDFAVYYC | 90 |
|  | A11 | GIPDRFSGSGSGTDFTLTISRLEPEDFAVYYC | 90 |
|  | L2 | GIPARFSGSGSGTEFTLTISSLQSEDFAVYYC | 91 |
|  | L16 | GIPARFSGSGSGTEFTLTISSLQSEDFAVYYC | 91 |
|  | L6 | GIPARFSGSGSGTDFTLTISSLEPEDFAVYYC | 92 |
|  | L20 | GIPARFSGSGPGTDFTLTISSLEPEDFAVYYC | 93 |
|  | L25 | GIPARFSGSGSGTDFTLTISSLQPEDFAVYYC | 94 |
| VKIV | B3 | GVPDRFSGSGSGTDFTLTISSLQAEDVAVYYC | 95 |
| VKV | B2 | GIPPRFSGSGYGTDFTLTINNIESEDAAYYFC | 96 |
| VKVI | A26 | GVPSRFSGSGSGTDFTLTINSLEAEDAATYYC | 97 |
| VKVI | A10 | GVPSRFSGSGSGTDFTLTINSLEAEDAATYYC | 97 |
|  | A14 | GVPSRFSGSGSGTDFTFTISSLEAEDAATYYC | 98 |

Fig. 8a

| | | FR1 | | SEQ NO: | FR2 | | SEQ NO: |
|---|---|---|---|---|---|---|---|
| | | | 2 | | 3 | 4 | |
| | Locus | 12345678901234567890123 | | | 567890123456789 | | |
| VL1 | 1a | QSVLTQPPSVSEAPRQRVTISC | | 99 | WYQQLPGKAPKLLIY | | 100 |
| | 1e | QSVLTQPPSVSGAPGQRVTISC | | 101 | WYQQLPGTAPKLLIY | | 102 |
| | 1c | QSVLTQPPSASGTPGQRVTISC | | 103 | WYQQLPGTAPKLLIY | | 102 |
| | 1g | QSVLTQPPSASGTPGQRVTISC | | 103 | WYQQLPGTAPKLLIY | | 102 |
| | 1b | QSVLTQPPSVSAAPGQKVTISC | | 104 | WYQQLPGTAPKLLIY | | 102 |
| VL2 | 2c | QSALTQPPSASGSPGQSVTISC | | 105 | WYQQHPGKAPKLMIY | | 106 |
| | 2e | QSALTQPRSVSGSPGQSVTISC | | 107 | WYQQHPGKAPKLMIY | | 106 |
| | 2a2 | QSALTQPASVSGSPGQSITISC | | 108 | WYQQHPGKAPKLMIY | | 106 |
| | 2d | QSALTQPPSVSGSPGQSVTISC | | 109 | WYQQPPGTAPKLMIY | | 110 |
| | 2b2 | QSALTQPASVSGSPGQSITISC | | 108 | WYQQHPGKAPKLMIY | | 106 |
| VL3 | 3r | SYELTQPPSVSVSPGQTASITC | | 111 | WYQQKPGQSPVLVIY | | 112 |
| | 3j | SYELTQPLSVSVALGQTARITC | | 113 | WYQQKPGQAPVLVIY | | 114 |
| | 3p | SYELTQPPSVSVSPGQTARITC | | 115 | WYQQKSGQAPVLVIY | | 116 |
| | 3a | SYELTQPPSVSVSLGQMARITC | | 117 | WYQQKPGQFPVLVIY | | 118 |
| | 3l | SSELTQDPAVSVALGQTVRITC | | 119 | WYQQKPGQAPVLVIY | | 114 |
| | 3h | SYVLTQPPSVSVAPGKTARITC | | 120 | WYQQKPGQAPVLVIY | | 114 |
| | 3e | SYELTQLPSVSVSPGQTARITC | | 121 | WYQQKPGQAPELVIY | | 122 |
| | 3m | SYELMQPPSVSVSPGQTARITC | | 123 | WYQQKPGQAPVLVIY | | 114 |
| | 2-19 | SYELTQPSSVSVSPGQTARITC | | 124 | WFQQKPGQAPVLVIY | | 125 |
| VL4 | 4c | LPVLTQPPSASALLGASIKLTC | | 126 | WYQQRPGRSPQYIMK | | 127 |
| | 4a | QPVLTQSSSASASLGSSVKLTC | | 128 | WHQQQPGKAPRYLMK | | 129 |
| | 4b | QLVLTQSPSASASLGASVKLTC | | 130 | WHQQQPEKGPRYLMK | | 131 |
| VL5 | 5e | QPVLTQPPSSSASPGESARLTC | | 132 | WYQQKPGSPPRYLLY | | 133 |
| | 5c | QAVLTQPASLSASPGASASLTC | | 134 | WYQQKPGSPPQYLLR | | 135 |
| | 5b | QPVLTQPSSHSASSGASVRLTC | | 136 | WYQQKPGNPPRYLLY | | 137 |
| VL6 | 6a | NFMLTQPHSVSESPGKTVTISC | | 138 | WYQQRPGSSPTTVIY | | 139 |
| VL7 | 7a | QTVVTQEPSLTVSPGGTVTLTC | | 140 | WFQQKPGQAPRALIY | | 141 |
| | 7b | QAVVTQEPSLTVSPGGTVTLTC | | 142 | WFQQKPGQAPRTLIY | | 143 |
| VL8 | 8a | QTVVTQEPSFSVSPGGTVTLTC | | 144 | WYQQTPGQAPRTLIY | | 145 |
| VL9 | 9a | QPVLTQPPSASASLGASVTLTC | | 146 | WYQQRPGKGPRFVMR | | 147 |
| VL10 | 10a | QAGLTQPPSVSKGLRQTATLTC | | 148 | WLQQHQGHPPKLLSY | | 149 |

Fig. 8b

|  |  | FR3 |  |
|---|---|---|---|
|  |  | 5    6              7              8 | SEQ NO: |
|  | Locus | 789012345678ab9012345678901234 5678 |  |
| VL1 | 1a | GVSDRFSGSKSG--TSASLAISGLQSEDEADYYC | 150 |
|  | 1e | GVPDRFSGSKSG--TSASLAITGLQAEDEADYYC | 151 |
|  | 1c | GVPDRFSGSKSG--TSASLAISGLQSEDEADYYC | 152 |
|  | 1g | GVPDRFSGSKSG--TSASLAISGLRSEDEADYYC | 153 |
|  | 1b | GIPDRFSGSKSG--TSATLGITGLQTGDEADYYC | 154 |
| VL2 | 2c | GVPDRFSGSKSG--NTASLTVSGLQAEDEADYYC | 155 |
|  | 2e | GVPDRFSGSKSG--NTASLTISGLQAEDEADYYC | 156 |
|  | 2a2 | GVSNRFSGSKSG--NTASLTISGLQAEDEADYYC | 157 |
|  | 2d | GVPDRFSGSKSG--NTASLTISGLQAEDEADYYC | 156 |
|  | 2b2 | GVSNRFSGSKSG--NTASLTISGLQAEDEADYYC | 157 |
| VL3 | 3r | GIPERFSGSNSG--NTATLTISGTQAMDEADYYC | 158 |
|  | 3j | GIPERFSGSNSG--NTATLTISRAQAGDEADYYC | 159 |
|  | 3p | GIPERFSGSSSG--TMATLTISGAQVEDEADYYC | 160 |
|  | 3a | GIPERFSGSSSG--TIVTLTISGVQAEDEADYYC | 161 |
|  | 3l | GIPDRFSGSSSG--NTASLTITGAQAEDEADYYC | 162 |
|  | 3h | GIPERFSGSNSG--NTATLTISRVEAGDEADYYC | 163 |
|  | 3e | GIPERFSGSTSG--NTTTLTISRVLTEDEADYYC | 164 |
|  | 3m | GIPERFSGSSSG--TTVTLTISGVQAEDEADYYC | 165 |
|  | 2-19 | GIPERFSGSSSG--TTVTLTISGAQVEDEADYYC | 166 |
| VL4 | 4c | GIPDRFMGSSSG--ADRYLTFSNLQSDDEAEYHC | 167 |
|  | 4a | GVPDRFSGSSSG--ADRYLTISNLQLEDEADYYC | 168 |
|  | 4b | GIPDRFSGSSSG--AERYLTISSLQSEDEADYYC | 169 |
| VL5 | 5e | GVPSRFSGSKDASANTGILLISGLQSEDEADYYC | 170 |
|  | 5c | GVPSRFSGSKDASANAGILLISGLQSEDEADYYC | 171 |
|  | 5b | GVPSRFSGSNDASANAGILRISGLQPEDEADYYC | 172 |
| VL6 | 6a | GVPDRFSGSIDSSSNSASLTISGLKTEDEADYYC | 173 |
| VL7 | 7a | WTPARFSGSLLG--GKAALTLSGVQPEDEAEYYC | 174 |
|  | 7b | WTPARFSGSLLG--GKAALTLSGAQPEDEAEYYC | 175 |
| VL8 | 8a | GVPDRFSGSILG--NKAALTITGAQADDESDYYC | 176 |
| VL9 | 9a | GIPDRFSVLGSG--LNRYLTIKNIQEEDESDYHC | 177 |
| VL10 | 10a | GISERLSASRSG--NTASLTITGLQPEDEADYYC | 178 |

Fig. 9a

| | | FR1 | | | | FR2 | | |
|---|---|---|---|---|---|---|---|---|
| | | 1 | 2 | 3 | SEQ NO: | 3 | 4 | SEQ NO: |
| | Locus | 12345678901234567890123456789 0 | | | | 67890123456789 | | |
| VH1 | 1-02 | QVQLVQSGAEVKKPGASVKVSCKASGYTFT | | | 179 | WVRQAPGQGLEWMG | | 180 |
| | 1-03 | QVQLVQSGAEVKKPGASVKVSCKASGYTFT | | | 179 | WVRQAPGQRLEWMG | | 181 |
| | 1-08 | QVQLVQSGAEVKKPGASVKVSCKASGYTFT | | | 179 | WVRQATGQGLEWMG | | 182 |
| | 1-18 | QVQLVQSGAEVKKPGASVKVSCKASGYTFT | | | 179 | WVRQAPGQGLEWMG | | 180 |
| | 1-24 | QVQLVQSGAEVKKPGASVKVSCKVSGYTLT | | | 183 | WVRQAPGKGLEWMG | | 184 |
| | 1-45 | QMQLVQSGAEVKKTGSSVKVSCKASGYTFT | | | 185 | WVRQAPGQALEWMG | | 186 |
| | 1-46 | QVQLVQSGAEVKKPGASVKVSCKASGYTFT | | | 179 | WVRQAPGQGLEWMG | | 180 |
| | 1-58 | QMQLVQSGPEVKKPGTSVKVSCKASGFTFT | | | 187 | WVRQARGQRLEWIG | | 188 |
| | 1-69 | QVQLVQSGAEVKKPGSSVKVSCKASGGTFS | | | 189 | WVRQAPGQGLEWMG | | 180 |
| | 1-e | QVQLVQSGAEVKKPGSSVKVSCKASGGTFS | | | 189 | WVRQAPGQGLEWMG | | 180 |
| | 1-f | EVQLVQSGAEVKKPGATVKISCKVSGYTFT | | | 190 | WVQQAPGKGLEWMG | | 191 |
| VH2 | 2-05 | QITLKESGPTLVKPTQTLTLTCTFSGFSLS | | | 192 | WIRQPPGKALEWLA | | 193 |
| | 2-26 | QVTLKESGPVLVKPTETLTLTCTVSGFSLS | | | 194 | WIRQPPGKALEWLA | | 193 |
| | 2-70 | QVTLKESGPALVKPTQTLTLTCTFSGFSLS | | | 195 | WIRQPPGKALEWLA | | 193 |
| VH3 | 3-07 | EVQLVESGGGLVQPGGSLRLSCAASGFTFS | | | 196 | WVRQAPGKGLEWVA | | 197 |
| | 3-09 | EVQLVESGGGLVQPGRSLRLSCAASGFTFD | | | 198 | WVRQAPGKGLEWVS | | 199 |
| | 3-11 | QVQLVESGGGLVKPGGSLRLSCAASGFTFS | | | 200 | WIRQAPGKGLEWVS | | 201 |
| | 3-13 | EVQLVESGGGLVQPGGSLRLSCAASGFTFS | | | 196 | WVRQATGKGLEWVS | | 202 |
| | 3-15 | EVQLVESGGGLVKPGGSLRLSCAASGFTFS | | | 203 | WVRQAPGKGLEWVG | | 204 |
| | 3-20 | EVQLVESGGGVVRPGGSLRLSCAASGFTFD | | | 205 | WVRQAPGKGLEWVS | | 199 |
| | 3-21 | EVQLVESGGGLVKPGGSLRLSCAASGFTFS | | | 203 | WVRQAPGKGLEWVS | | 199 |
| | 3-23 | EVQLLESGGGLVQPGGSLRLSCAASGFTFS | | | 206 | WVRQAPGKGLEWVS | | 199 |
| | 3-30 | QVQLVESGGGVVQPGRSLRLSCAASGFTFS | | | 207 | WVRQAPGKGLEWVA | | 197 |
| | 3-30.3 | QVQLVESGGGVVQPGRSLRLSCAASGFTFS | | | 207 | WVRQAPGKGLEWVA | | 197 |
| | 3-30.5 | QVQLVESGGGVVQPGRSLRLSCAASGFTFS | | | 207 | WVRQAPGKGLEWVA | | 197 |
| | 3-33 | QVQLVESGGGVVQPGRSLRLSCAASGFTFS | | | 207 | WVRQAPGKGLEWVA | | 197 |
| | 3-43 | EVQLVESGGVVVQPGGSLRLSCAASGFTFD | | | 208 | WVRQAPGKGLEWVS | | 199 |
| | 3-48 | EVQLVESGGGLVQPGGSLRLSCAASGFTFS | | | 196 | WVRQAPGKGLEWVS | | 199 |
| | 3-49 | EVQLVESGGGLVQPGRSLRLSCTASGFTFG | | | 209 | WFRQAPGKGLEWVG | | 210 |
| | 3-53 | EVQLVETGGGLIQPGGSLRLSCAASGFTVS | | | 211 | WVRQAPGKGLEWVS | | 199 |
| | 3-64 | EVQLVESGGGLVQPGGSLRLSCAASGFTFS | | | 196 | WVRQAPGKGLEYVS | | 212 |
| | 3-66 | EVQLVESGGGLVQPGGSLRLSCAASGFTVS | | | 213 | WVRQAPGKGLEWVS | | 199 |
| | 3-72 | EVQLVESGGGLVQPGGSLRLSCAASGFTFS | | | 196 | WVRQAPGKGLEWVG | | 204 |
| | 3-73 | EVQLVESGGGLVQPGGSLKLSCAASGFTFS | | | 214 | WVRQASGKGLEWVG | | 215 |
| | 3-74 | EVQLVESGGGLVQPGGSLRLSCAASGFTFS | | | 196 | WVRQAPGKGLVWVS | | 216 |
| | 3-d | EVQLVESRGVLVQPGGSLRLSCAASGFTVS | | | 217 | WVRQAPGKGLEWVS | | 199 |
| VH4 | 4-04 | QVQLQESGPGLVKPSGTLSLTCAVSGGSIS | | | 218 | WVRQPPGKGLEWIG | | 219 |
| | 4-28 | QVQLQESGPGLVKPSDTLSLTCAVSGYSIS | | | 220 | WIRQPPGKGLEWIG | | 221 |
| | 4-30.1 | QVQLQESGPGLVKPSQTLSLTCTVSGGSIS | | | 222 | WIRQHPGKGLEWIG | | 223 |
| | 4-30.2 | QLQLQESGSGLVKPSQTLSLTCAVSGGSIS | | | 224 | WIRQPPGKGLEWIG | | 221 |
| | 4-30.4 | QVQLQESGPGLVKPSQTLSLTCTVSGGSIS | | | 222 | WIRQPPGKGLEWIG | | 221 |
| | 4-31 | QVQLQESGPGLVKPSQTLSLTCTVSGGSIS | | | 222 | WIRQHPGKGLEWIG | | 223 |
| | 4-34 | QVQLQQWGAGLLKPSETLSLTCAVYGGSFS | | | 225 | WIRQPPGKGLEWIG | | 221 |
| | 4-39 | QLQLQESGPGLVKPSETLSLTCTVSGGSIS | | | 226 | WIRQPPGKGLEWIG | | 221 |
| | 4-59 | QVQLQESGPGLVKPSETLSLTCTVSGGSIS | | | 227 | WVRQPPGKGLEWIG | | 221 |
| | 4-61 | QVQLQESGPGLVKPSETLSLTCTVSGGSYS | | | 228 | WIRQPPGKGLEWIG | | 221 |
| | 4-b | QVQLQESGPGLVKPSETLSLTCAVSGYSIS | | | 229 | WIRQPPGKGLEWIG | | 221 |
| VH5 | 5-51 | EVQLVQSGAEVKKPGESLKISCKGSGYSFT | | | 230 | WVRQMPGKGLEWMG | | 231 |
| | 5-a | EVQLVQSGAEVKKPGESLRISCKGSGYSFT | | | 232 | WVRQMPGKGLEWMG | | 231 |
| VH6 | 6-01 | QVQLQQSGPGLVKPSQTLSLTCAISGDSVS | | | 233 | WIRQSPSRGLEWLG | | 234 |
| VH7 | 7-4.1 | QVQLVQSGSELKKPGASVKVSCKASGYTFT | | | 235 | WVRQAPGQGLEWMG | | 180 |

Fig. 9b

|  |  | FR3 | | | | SEQ NO: |
|---|---|---|---|---|---|---|
|  |  | 6 | 7 | 8 | 9 | |
|  | Locus | 67890123456789012abc345678901234 | | | | |
| VH1 | 1-02 | RVTMTRDTSISTAYMELSRLRSDDTAVYYCAR | | | | 237 |
|  | 1-03 | RVTITRDTSASTAYMELSSLRSEDTAVYYCAR | | | | 238 |
|  | 1-08 | RVTMTRNTSISTAYMELSSLRSEDTAVYYCAR | | | | 239 |
|  | 1-18 | RVTMTTDTSTSTAYMELRSLRSDDTAVYYCAR | | | | 240 |
|  | 1-24 | RVTMTEDTSTDTAYMELSSLRSEDTAVYYCAT | | | | 241 |
|  | 1-45 | RVTITRDRSMSTAYMELSSLRSEDTAMYYCAR | | | | 242 |
|  | 1-46 | RVTMTRDTSTSTVYMELSSLRSEDTAVYYCAR | | | | 243 |
|  | 1-58 | RVTITRDMSTSTAYMELSSLRSEDTAVYYCAA | | | | 244 |
|  | 1-69 | RVTITADESTSTAYMELSSLRSEDTAVYYCAR | | | | 245 |
|  | 1-e | RVTITADKSTSTAYMELSSLRSEDTAVYYCAR | | | | 246 |
|  | 1-f | RVTITADTSTDTAYMELSSLRSEDTAVYYCAT | | | | 247 |
| VH2 | 2-05 | RLTITKDTSKNQVVLTMTNMDPVDTATYYCAHR | | | | 248 |
|  | 2-26 | RLTISKDTSKSQVVLTMTNMDPVDTATYYCARI | | | | 249 |
|  | 2-70 | RLTISKDTSKNQVVLTMTNMDPVDTATYYCARI | | | | 250 |
| VH3 | 3-07 | RFTISRDNAKNSLYLQMNSLRAEDTAVYYCAR | | | | 251 |
|  | 3-09 | RFTISRDNAKNSLYLQMNSLRAEDTALYYCAKD | | | | 252 |
|  | 3-11 | RFTISRDNAKNSLYLQMNSLRAEDTAVYYCAR | | | | 251 |
|  | 3-13 | RFTISRDNAKNSLYLQMNSLRAEDTAVYYCAR | | | | 251 |
|  | 3-15 | RFTISRDDSKNTLYLQMNSLKTEDTAVYYCTT | | | | 253 |
|  | 3-20 | RFTISRDNAKNSLYLQMNSLRAEDTALYHCAR | | | | 254 |
|  | 3-21 | RFTISRDNAKNSLYLQMNSLRAEDTAVYYCAR | | | | 251 |
|  | 3-23 | RFTISRDNSKNTLYLQMNSLRAEDTAVYYCAK | | | | 255 |
|  | 3-30 | RFTISRDNSKNTLYLQMNSLRAEDTAVYYCAK | | | | 255 |
|  | 3-30.3 | RFTISRDNSKNTLYLQMNSLRAEDTAVYYCAR | | | | 256 |
|  | 3-30.5 | RFTISRDNSKNTLYLQMNSLRAEDTAVYYCAK | | | | 255 |
|  | 3-33 | RFTISRDNSKNTLYLQMNSLRAEDTAVYYCAR | | | | 256 |
|  | 3-43 | RFTISRDNSKNSLYLQMNSLRTEDTALYYCAKD | | | | 257 |
|  | 3-48 | RFTISRDNAKNSLYLQMNSLRDEDTAVYYCAR | | | | 258 |
|  | 3-49 | RFTISRDGSKSIAYLQMNSLKTEDTAVYYCTR | | | | 259 |
|  | 3-53 | RFTISRDNSKNTLYLQMNSLRAEDTAVYYCAR | | | | 256 |
|  | 3-64 | RFTISRDNSKNTLYLQMGSLRAEDMAVYYCAR | | | | 260 |
|  | 3-66 | RFTISRDNSKNTLYLQMNSLRAEDTAVYYCAR | | | | 256 |
|  | 3-72 | RFTISRDDSKNSLYLQMNSLKTEDTAVYYCAR | | | | 261 |
|  | 3-73 | RFTISRDDSKNTAYLQMNSLKTEDTAVYYCTR | | | | 262 |
|  | 3-74 | RFTISRDNAKNTLYLQMNSLRAEDTAVYYCAR | | | | 263 |
|  | 3-d | RFTISRDNSKNTLHLQMNSLRAEDTAVYYCKK | | | | 264 |
| VH4 | 4-04 | RVTISVDKSKNQFSLKLSSVTAADTAVYYCAR | | | | 265 |
|  | 4-28 | RVTMSVDTSKNQFSLKLSSVTAVDTAVYYCAR | | | | 266 |
|  | 4-30.1 | RVTISVDTSKNQFSLKLSSVTAADTAVYYCAR | | | | 267 |
|  | 4-30.2 | RVTISVDRSKNQFSLKLSSVTAADTAVYYCAR | | | | 268 |
|  | 4-30.4 | RVTISVDTSKNQFSLKLSSVTAADTAVYYCAR | | | | 267 |
|  | 4-31 | RVTISVDTSKNQFSLKLSSVTAADTAVYYCAR | | | | 267 |
|  | 4-34 | RVTISVDTSKNQFSLKLSSVTAADTAVYYCAR | | | | 267 |
|  | 4-39 | RVTISVDTSKNQFSLKLSSVTAADTAVYYCAR | | | | 267 |
|  | 4-59 | RVTISVDTSKNQFSLKLSSVTAADTAVYYCAR | | | | 267 |
|  | 4-61 | RVTISVDTSKNQFSLKLSSVTAADTAVYYCAR | | | | 267 |
|  | 4-b | RVTISVD'TSKNQFSLKLSSVTAADTAVYYCAR | | | | 267 |
| VH5 | 5-51 | QVTISADKSISTAYLQWSSLKASDTAMYYCAR | | | | 269 |
|  | 5-a | HVTISADKSISTAYLQWSSLKASDTAMYYCAR | | | | 270 |
| VH6 | 6-01 | RITINPDTSKNQFSLQLNSVTPEDTAVYYCAR | | | | 271 |
| VH7 | 7-4.1 | RFVFSLDTSVSTAYLQICSLKAEDTAVYYCAR | | | | 272 |

SEQUENCE LISTING

<160> NUMBER OF SEQ ID NOS: 272

<210> SEQ ID NO 1
<211> LENGTH: 11
<212> TYPE: PRT
<213> ORGANISM: Artificial Sequence
<220> FEATURE:
<223> OTHER INFORMATION: Synthetic peptide

<400> SEQUENCE: 1

Lys Ala Ser Gln Asn Val Gly Thr Asn Val Gly
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

Ser Ala Ser Phe Arg Tyr Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Gln Gln Tyr Tyr Thr Tyr Pro Tyr Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Ser Tyr Thr Leu Ala
1               5

<210> SEQ ID NO 5
<211> LENGTH: 16
<212> TYPE: PRT
<213> ORGANISM: Artificial Sequence
<220> FEATURE:

```
<223> OTHER INFORMATION: Synthetic peptide

<400> SEQUENCE: 5

Ala Ile Asp Ser Ser Ser Tyr Thr Tyr Ser Pro Asp Thr Val Arg Gly
1               5                   10                  15

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Asp Ser Asn Trp Asp Ala Leu Asp Tyr
1               5

<210> SEQ ID NO 7
<211> LENGTH: 107
<212> TYPE: PRT
<213> ORGANISM: Artificial Sequence
<220> FEATURE:
<223> OTHER INFORMATION: Synthetic peptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
                20                  25                  30

Val Gly Trp Tyr Gln Gln Lys Pro Gly Lys Ala Pro Lys Ala Leu Ile
            35                  40                  45

Tyr Ser Ala Ser Phe Arg Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Tyr Pro Tyr
                85                  90                  95

Thr Phe Gly Gly Gly Thr Lys Val Glu Ile Lys
            100                 105

<210> SEQ ID NO 8
<211> LENGTH: 117
<212> TYPE: PRT
<213> ORGANISM: Artificial Sequence
<220> FEATURE:
<223> OTHER INFORMATION: Synthetic peptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Thr Leu Ala Trp Val Arg Gln Ala Pro Gly Lys Gly Leu Glu Trp Val
            35                  40                  45

Ala Ala Ile Asp Ser Ser Ser Tyr Thr Tyr Ser Pro Asp Thr Val Arg
        50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asp Ser Asn Trp Asp Ala Leu Asp Tyr Trp Gly Gln Gly Thr Thr
```

```
                    100                 105                 110

Val Thr Val Ser Ser
            115

<210> SEQ ID NO 9
<211> LENGTH: 214
<212> TYPE: PRT
<213> ORGANISM: Artificial Sequence
<220> FEATURE:
<223> OTHER INFORMATION: Synthetic peptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Gly Trp Tyr Gln Gln Lys Pro Gly Lys Ala Pro Lys Ala Leu Ile
        35                  40                  45

Tyr Ser Ala Ser Phe Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 10
<211> LENGTH: 447
<212> TYPE: PRT
<213> ORGANISM: Artificial Sequence
<220> FEATURE:
<223> OTHER INFORMATION: Synthetic peptide

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Leu Ala Trp Val Arg Gln Ala Pro Gly Lys Gly Leu Glu Trp Val
        35                  40                  45

Ala Ala Ile Asp Ser Ser Ser Tyr Thr Tyr Ser Pro Asp Thr Val Arg
    50                  55                  60

Gly Arg Phe Thr Ile Ser Arg Asp Asn Ala Lys Asn Ser Leu Tyr Leu
```

```
                65                  70                  75                  80
            Gln Met Asn Ser Leu Arg Ala Glu Asp Thr Ala Val Tyr Tyr Cys Ala
                            85                  90                  95

Arg Asp Ser Asn Trp Asp Ala Leu Asp Tyr Trp Gly Gln Gly Thr Thr
                            100                 105                 110

Val Thr Val Ser Ser Ala Ser Thr Lys Gly Pro Ser Val Phe Pro Leu
                            115                 120                 125

Ala Pro Ser Ser Lys Ser Thr Ser Gly Gly Thr Ala Ala Leu Gly Cys
                            130                 135                 140

Leu Val Lys Asp Tyr Phe Pro Glu Pro Val Thr Val Ser Trp Asn Ser
            145                 150                 155                 160

Gly Ala Leu Thr Ser Gly Val His Thr Phe Pro Ala Val Leu Gln Ser
                            165                 170                 175

Ser Gly Leu Tyr Ser Leu Ser Ser Val Val Thr Val Pro Ser Ser Ser
                            180                 185                 190

Leu Gly Thr Gln Thr Tyr Ile Cys Asn Val Asn His Lys Pro Ser Asn
                            195                 200                 205

Thr Lys Val Asp Lys Lys Val Glu Pro Lys Ser Cys Asp Lys Thr His
                            210                 215                 220

Thr Cys Pro Pro Cys Pro Ala Pro Glu Leu Leu Gly Gly Pro Ser Val
            225                 230                 235                 240

Phe Leu Phe Pro Pro Lys Pro Lys Asp Thr Leu Met Ile Ser Arg Thr
                            245                 250                 255

Pro Glu Val Thr Cys Val Val Val Asp Val Ser His Glu Asp Pro Glu
                            260                 265                 270

Val Lys Phe Asn Trp Tyr Val Asp Gly Val Glu Val His Asn Ala Lys
                            275                 280                 285

Thr Lys Pro Arg Glu Glu Gln Tyr Asn Ser Thr Tyr Arg Val Val Ser
                            290                 295                 300

Val Leu Thr Val Leu His Gln Asp Trp Leu Asn Gly Lys Glu Tyr Lys
            305                 310                 315                 320

Cys Lys Val Ser Asn Lys Ala Leu Pro Ala Pro Ile Glu Lys Thr Ile
                            325                 330                 335

Ser Lys Ala Lys Gly Gln Pro Arg Glu Pro Gln Val Tyr Thr Leu Pro
                            340                 345                 350

Pro Ser Arg Asp Glu Leu Thr Lys Asn Gln Val Ser Leu Thr Cys Leu
                            355                 360                 365

Val Lys Gly Phe Tyr Pro Ser Asp Ile Ala Val Glu Trp Glu Ser Asn
                            370                 375                 380

Gly Gln Pro Glu Asn Asn Tyr Lys Thr Thr Pro Pro Val Leu Asp Ser
            385                 390                 395                 400

Asp Gly Ser Phe Phe Leu Tyr Ser Lys Leu Thr Val Asp Lys Ser Arg
                            405                 410                 415

Trp Gln Gln Gly Asn Val Phe Ser Cys Ser Val Met His Glu Ala Leu
                            420                 425                 430

His Asn His Tyr Thr Gln Lys Ser Leu Ser Leu Ser Pro Gly Lys
                            435                 440                 445

<210> SEQ ID NO 11
<211> LENGTH: 239
<212> TYPE: PRT
<213> ORGANISM: Artificial Sequence
<220> FEATURE:
<223> OTHER INFORMATION: Synthetic peptide

<400> SEQUENCE: 11
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Gly Trp Tyr Gln Gln Lys Pro Gly Lys Ala Pro Lys Ala Leu Ile
            35                  40                  45

Tyr Ser Ala Ser Phe Arg Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Thr Tyr Tyr Pro Tyr
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Glu Val Gln Leu Val Glu
            115                 120                 125

Ser Gly Gly Gly Leu Val Gln Pro Gly Gly Ser Leu Arg Leu Ser Cys
130                 135                 140

Ala Ala Ser Gly Phe Thr Phe Ser Ser Tyr Thr Leu Ala Trp Val Arg
145                 150                 155                 160

Gln Ala Pro Gly Lys Gly Leu Glu Trp Val Ala Ala Ile Asp Ser Ser
            165                 170                 175

Ser Tyr Thr Tyr Ser Pro Asp Thr Val Arg Gly Arg Phe Thr Ile Ser
            180                 185                 190

Arg Asp Asn Ala Lys Asn Ser Leu Tyr Leu Gln Met Asn Ser Leu Arg
            195                 200                 205

Ala Glu Asp Thr Ala Val Tyr Tyr Cys Ala Arg Asp Ser Asn Trp Asp
            210                 215                 220

Ala Leu Asp Tyr Trp Gly Gln Gly Thr Thr Val Thr Val Ser Ser
225                 230                 235

<210> SEQ ID NO 12
<211> LENGTH: 239
<212> TYPE: PRT
<213> ORGANISM: Artificial Sequence
<220> FEATURE:
<223> OTHER INFORMATION: Synthetic peptide

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Leu Ala Trp Val Arg Gln Ala Pro Gly Lys Gly Leu Glu Trp Val
            35                  40                  45

Ala Ala Ile Asp Ser Ser Ser Tyr Thr Tyr Ser Pro Asp Thr Val Arg
            50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asp Ser Asn Trp Asp Ala Leu Asp Tyr Trp Gly Gln Gly Thr Thr
            100                 105                 110

Val Thr Val Ser Ser Gly Gly Gly Gly Ser Gly Gly Gly Gly Ser Gly
            115                 120                 125

```
Gly Gly Gly Ser Asp Ile Gln Met Thr Gln Ser Pro Ser Ser Leu Ser
            130                 135                 140

Ala Ser Val Gly Asp Arg Val Thr Ile Thr Cys Lys Ala Ser Gln Asn
145                 150                 155                 160

Val Gly Thr Asn Val Gly Trp Tyr Gln Gln Lys Pro Gly Lys Ala Pro
                165                 170                 175

Lys Ala Leu Ile Tyr Ser Ala Ser Phe Arg Tyr Ser Gly Val Pro Ser
            180                 185                 190

Arg Phe Ser Gly Ser Gly Ser Gly Thr Asp Phe Thr Leu Thr Ile Ser
            195                 200                 205

Ser Leu Gln Pro Glu Asp Phe Ala Thr Tyr Tyr Cys Gln Gln Tyr Tyr
            210                 215                 220

Thr Tyr Pro Tyr Thr Phe Gly Gly Thr Lys Val Glu Ile Lys
225                 230                 235
```

```
<210> SEQ ID NO 13
<211> LENGTH: 5
<212> TYPE: PRT
<213> ORGANISM: Artificial Sequence
<220> FEATURE:
<223> OTHER INFORMATION: Synthetic peptide

<400> SEQUENCE: 13

Lys Ala Pro Lys Ala
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Phe Gly Gly Gly Thr Lys Val Glu Ile Lys
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide

<400> SEQUENCE: 15

Phe Gly Gln Gly Thr Lys Val Glu Ile Lys
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic peptide

<400> SEQUENCE: 16

Phe Gly Gln Gly Thr Lys Leu Glu Ile Lys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic peptide
```

```
<400> SEQUENCE: 17

Phe Gly Pro Gly Thr Lys Val Asp Ile Lys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18

Phe Gly Gln Gly Thr Arg Leu Glu Ile Lys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide

<400> SEQUENCE: 19

Phe Gly Thr Gly Thr Lys Val Thr Val Leu
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Phe Gly Gly Gly Thr Lys Leu Thr Val Leu
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic peptide

<400> SEQUENCE: 21

Phe Gly Gly Gly Thr Gln Leu Thr Val Leu
1               5                   10

<210> SEQ ID NO 22
<211> LENGTH: 30
<212> TYPE: PRT
<213> ORGANISM: Artificial Sequence
<220> FEATURE:
<223> OTHER INFORMATION: Synthetic peptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 23
<211> LENGTH: 14
<212> TYPE: PRT
<213> ORGANISM: Artificial Sequence
<220> FEATURE:
```

-continued

<223> OTHER INFORMATION: Synthetic peptide

<400> SEQUENCE: 23

Trp Val Arg Gln Ala Pro Gly Lys Gly Leu Glu Trp Val Ala
1               5                   10

<210> SEQ ID NO 24
<211> LENGTH: 32
<212> TYPE: PRT
<213> ORGANISM: Artificial Sequence
<220> FEATURE:
<223> OTHER INFORMATION: Synthetic peptide

<400> SEQUENCE: 24

Arg Phe Thr Ile Ser Arg Asp Asn Ala Lys Asn Ser Leu Tyr Leu Gln
1               5                   10                  15
Met Asn Ser Leu Arg Ala Glu Asp Thr Ala Val Tyr Tyr Cys Ala Arg
            20                  25                  30

<210> SEQ ID NO 25
<211> LENGTH: 11
<212> TYPE: PRT
<213> ORGANISM: Artificial Sequence
<220> FEATURE:
<223> OTHER INFORMATION: Synthetic peptide

<400> SEQUENCE: 25

Trp Gly Gln Gly Thr Leu Val Thr Val Ser Ser
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide

<400> SEQUENCE: 26

Trp Gly Arg Gly Thr Leu Val Thr Val Ser Ser
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic peptide

<400> SEQUENCE: 27

Trp Gly Gln Gly Thr Met Val Thr Val Ser Ser
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic peptide

<400> SEQUENCE: 28

Trp Gly Gln Gly Thr Thr Val Thr Val Ser Ser
1               5                   10

<210> SEQ ID NO 29
<211> LENGTH: 65
<212> TYPE: PRT
<213> ORGANISM: Artificial Sequence

```
<220> FEATURE:
<223> OTHER INFORMATION: Synthetic peptide

<400> SEQUENCE: 29

Asp Val Arg Leu Val Glu Ser Gly Gly Gly Leu Val Lys Pro Gly Gly
1               5                   10                  15

Ser Leu Lys Leu Ser Cys Ala Ala Tyr Gly Phe Thr Phe Ser Ser Tyr
            20                  25                  30

Thr Leu Ala Trp Val Arg Gln Thr Pro Glu Lys Arg Leu Glu Trp Val
        35                  40                  45

Ala Ala Ile Asp Ser Ser Ser Tyr Thr Tyr Ser Pro Asp Thr Val Arg
    50                  55                  60

Gly
65

<210> SEQ ID NO 30
<211> LENGTH: 65
<212> TYPE: PRT
<213> ORGANISM: Artificial Sequence
<220> FEATURE:
<223> OTHER INFORMATION: Synthetic peptide

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Leu Ala Trp Val Arg Gln Ala Pro Gly Lys Gly Leu Glu Trp Val
        35                  40                  45

Ala Ala Ile Asp Ser Ser Ser Tyr Thr Tyr Ser Pro Asp Thr Val Arg
    50                  55                  60

Gly
65

<210> SEQ ID NO 31
<211> LENGTH: 53
<212> TYPE: PRT
<213> ORGANISM: Artificial Sequence
<220> FEATURE:
<223> OTHER INFORMATION: Synthetic peptide

<400> SEQUENCE: 31

Arg Phe Thr Ile Ser Arg Asp Asn Ala Lys Asn Thr Leu Tyr Leu Gln
1               5                   10                  15

Met Ser Ser Leu Lys Ser Glu Asp Thr Ala Met Tyr Tyr Cys Thr Arg
            20                  25                  30

Asp Ser Asn Trp Ala Asp Ala Leu Asp Tyr Trp Gly Gln Gly Thr Ser
        35                  40                  45

Val Ile Val Ser Ser
    50

<210> SEQ ID NO 32
<211> LENGTH: 52
<212> TYPE: PRT
<213> ORGANISM: Artificial Sequence
<220> FEATURE:
<223> OTHER INFORMATION: Synthetic peptide

<400> SEQUENCE: 32

Arg Phe Thr Ile Ser Arg Asp Asn Ala Lys Asn Ser Leu Tyr Leu Gln
1               5                   10                  15
```

Met Asn Ser Leu Arg Ala Glu Asp Thr Ala Val Tyr Tyr Cys Ala Arg
            20                  25                  30

Asp Ser Asn Trp Asp Ala Leu Asp Tyr Trp Gly Gln Gly Thr Thr Val
        35                  40                  45

Thr Val Ser Ser
    50

<210> SEQ ID NO 33
<211> LENGTH: 56
<212> TYPE: PRT
<213> ORGANISM: Artificial Sequence
<220> FEATURE:
<223> OTHER INFORMATION: Synthetic peptide

<400> SEQUENCE: 33

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Gly Trp Tyr Gln Gln Lys Pro Gly Gln Ser Pro Lys Ala Leu Ile
        35                  40                  45

Tyr Ser Ala Ser Phe Arg Tyr Ser
    50                  55

<210> SEQ ID NO 34
<211> LENGTH: 56
<212> TYPE: PRT
<213> ORGANISM: Artificial Sequence
<220> FEATURE:
<223> OTHER INFORMATION: Synthetic peptide

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Gly Trp Tyr Gln Gln Lys Pro Gly Lys Ala Pro Lys Leu Leu Ile
        35                  40                  45

Tyr Ser Ala Ser Phe Arg Tyr Ser
    50                  55

<210> SEQ ID NO 35
<211> LENGTH: 51
<212> TYPE: PRT
<213> ORGANISM: Artificial Sequence
<220> FEATURE:
<223> OTHER INFORMATION: Synthetic peptide

<400> SEQUENCE: 35

Gly Val Pro Asp Arg Phe Thr Gly Ser Gly Ser Gly Thr Asp Phe Ser
1               5                   10                  15

Leu Thr Ile Ser Asn Val Lys Ser Glu Asp Leu Ala Glu Tyr Phe Cys
            20                  25                  30

Gln Gln Tyr Tyr Thr Tyr Pro Tyr Thr Phe Gly Gly Gly Thr Lys Leu
        35                  40                  45

Glu Ile Lys
    50

<210> SEQ ID NO 36
<211> LENGTH: 51
<212> TYPE: PRT
<213> ORGANISM: Artificial Sequence

```
<220> FEATURE:
<223> OTHER INFORMATION: Synthetic peptide

<400> SEQUENCE: 36

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30

Gln Gln Tyr Tyr Thr Tyr Pro Tyr Thr Phe Gly Gly Gly Thr Lys Val
            35                  40                  45

Glu Ile Lys
    50

<210> SEQ ID NO 37
<211> LENGTH: 5
<212> TYPE: PRT
<213> ORGANISM: Artificial Sequence
<220> FEATURE:
<223> OTHER INFORMATION: Synthetic peptide

<400> SEQUENCE: 37

Gln Ser Pro Lys Ala
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic peptide

<400> SEQUENCE: 38

Lys Ala Pro Lys Leu
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic peptide

<400> SEQUENCE: 39

Gln Ser Pro Lys Leu
1               5

<210> SEQ ID NO 40
<211> LENGTH: 23
<212> TYPE: PRT
<213> ORGANISM: Artificial Sequence
<220> FEATURE:
<223> OTHER INFORMATION: Synthetic peptide

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 41
<211> LENGTH: 15
<212> TYPE: PRT
<213> ORGANISM: Artificial Sequence
<220> FEATURE:
<223> OTHER INFORMATION: Synthetic peptide
```

```
<400> SEQUENCE: 41

Trp Tyr Gln Gln Lys Pro Gly Lys Ala Pro Lys Leu Leu Ile Tyr
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic peptide

<400> SEQUENCE: 42

Trp Tyr Gln Gln Lys Pro Gly Lys Val Pro Lys Leu Leu Ile Tyr
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Synthetic peptide

<400> SEQUENCE: 43

Trp Tyr Gln Gln Lys Pro Gly Lys Ala Pro Lys Arg Leu Ile Tyr
1               5                   10                  15

<210> SEQ ID NO 44
<211> LENGTH: 23
<212> TYPE: PRT
<213> ORGANISM: Artificial Sequence
<220> FEATURE:
<223> OTHER INFORMATION: Synthetic peptide

<400> SEQUENCE: 44

Asn Ile Gln Met Thr Gln Ser Pro Ser Ala Met Ser Ala Ser Val Gly
1               5                   10                  15

Asp Arg Val Thr Ile Thr Cys
            20

<210> SEQ ID NO 45
<211> LENGTH: 15
<212> TYPE: PRT
<213> ORGANISM: Artificial Sequence
<220> FEATURE:
<223> OTHER INFORMATION: Synthetic peptide

<400> SEQUENCE: 45

Trp Phe Gln Gln Lys Pro Gly Lys Val Pro Lys His Leu Ile Tyr
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthetic peptide

<400> SEQUENCE: 46

Trp Phe Gln Gln Lys Pro Gly Lys Ala Pro Lys Ser Leu Ile Tyr
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic peptide
```

```
<400> SEQUENCE: 47

Trp Tyr Gln Gln Lys Pro Glu Lys Ala Pro Lys Ser Leu Ile Tyr
1               5                   10                  15

<210> SEQ ID NO 48
<211> LENGTH: 23
<212> TYPE: PRT
<213> ORGANISM: Artificial Sequence
<220> FEATURE:
<223> OTHER INFORMATION: Synthetic peptide

<400> SEQUENCE: 48

Ala Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 49
<211> LENGTH: 23
<212> TYPE: PRT
<213> ORGANISM: Artificial Sequence
<220> FEATURE:
<223> OTHER INFORMATION: Synthetic peptide

<400> SEQUENCE: 49

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 50
<211> LENGTH: 23
<212> TYPE: PRT
<213> ORGANISM: Artificial Sequence
<220> FEATURE:
<223> OTHER INFORMATION: Synthetic peptide

<400> SEQUENCE: 50

Asp Ile Gln Leu Thr Gln Ser Pro Ser Phe Leu Ser Ala Ser Val Gly
1               5                   10                  15

Asp Arg Val Thr Ile Thr Cys
            20

<210> SEQ ID NO 51
<211> LENGTH: 23
<212> TYPE: PRT
<213> ORGANISM: Artificial Sequence
<220> FEATURE:
<223> OTHER INFORMATION: Synthetic peptide

<400> SEQUENCE: 51

Ala Ile Arg Met Thr Gln Ser Pro Phe Ser Leu Ser Ala Ser Val Gly
1               5                   10                  15

Asp Arg Val Thr Ile Thr Cys
            20

<210> SEQ ID NO 52
<211> LENGTH: 15
<212> TYPE: PRT
<213> ORGANISM: Artificial Sequence
<220> FEATURE:
<223> OTHER INFORMATION: Synthetic peptide

<400> SEQUENCE: 52
```

```
Trp Tyr Gln Gln Lys Pro Ala Lys Ala Pro Lys Leu Phe Ile Tyr
1               5                   10                  15
```

<210> SEQ ID NO 53
<211> LENGTH: 23
<212> TYPE: PRT
<213> ORGANISM: Artificial Sequence
<220> FEATURE:
<223> OTHER INFORMATION: Synthetic peptide

<400> SEQUENCE: 53

```
Ala Ile Arg Met Thr Gln Ser Pro Ser Phe Ser Ala Ser Thr Gly
1               5                   10                  15

Asp Arg Val Thr Ile Thr Cys
            20
```

<210> SEQ ID NO 54
<211> LENGTH: 23
<212> TYPE: PRT
<213> ORGANISM: Artificial Sequence
<220> FEATURE:
<223> OTHER INFORMATION: Synthetic peptide

<400> SEQUENCE: 54

```
Val Ile Trp Met Thr Gln Ser Pro Ser Leu Leu Ser Ala Ser Thr Gly
1               5                   10                  15

Asp Arg Val Thr Ile Ser Cys
            20
```

<210> SEQ ID NO 55
<211> LENGTH: 15
<212> TYPE: PRT
<213> ORGANISM: Artificial Sequence
<220> FEATURE:
<223> OTHER INFORMATION: Synthetic peptide

<400> SEQUENCE: 55

```
Trp Tyr Gln Gln Lys Pro Gly Lys Ala Pro Glu Leu Leu Ile Tyr
1               5                   10                  15
```

<210> SEQ ID NO 56
<211> LENGTH: 23
<212> TYPE: PRT
<213> ORGANISM: Artificial Sequence
<220> FEATURE:
<223> OTHER INFORMATION: Synthetic peptide

<400> SEQUENCE: 56

```
Ala Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 57
<211> LENGTH: 22
<212> TYPE: PRT
<213> ORGANISM: Artificial Sequence
<220> FEATURE:
<223> OTHER INFORMATION: Synthetic peptide

<400> SEQUENCE: 57

```
Asp Ile Gln Met Thr Gln Ser Pro Ser Thr Leu Ser Ala Ser Val Asp
1               5                   10                  15

Arg Val Thr Ile Thr Cys
            20
```

-continued

<210> SEQ ID NO 58
<211> LENGTH: 23
<212> TYPE: PRT
<213> ORGANISM: Artificial Sequence
<220> FEATURE:
<223> OTHER INFORMATION: Synthetic peptide

<400> SEQUENCE: 58

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 59
<211> LENGTH: 15
<212> TYPE: PRT
<213> ORGANISM: Artificial Sequence
<220> FEATURE:
<223> OTHER INFORMATION: Synthetic peptide

<400> SEQUENCE: 59

Trp Tyr Leu Gln Lys Pro Gly Gln Ser Pro Gln Leu Leu Ile Tyr
1               5                   10                  15

<210> SEQ ID NO 60
<211> LENGTH: 23
<212> TYPE: PRT
<213> ORGANISM: Artificial Sequence
<220> FEATURE:
<223> OTHER INFORMATION: Synthetic peptide

<400> SEQUENCE: 60

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 61
<211> LENGTH: 15
<212> TYPE: PRT
<213> ORGANISM: Artificial Sequence
<220> FEATURE:
<223> OTHER INFORMATION: Synthetic peptide

<400> SEQUENCE: 61

Trp Phe Gln Gln Arg Pro Gly Gln Ser Pro Arg Arg Leu Ile Tyr
1               5                   10                  15

<210> SEQ ID NO 62
<211> LENGTH: 23
<212> TYPE: PRT
<213> ORGANISM: Artificial Sequence
<220> FEATURE:
<223> OTHER INFORMATION: Synthetic peptide

<400> SEQUENCE: 62

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 63
<211> LENGTH: 15
<212> TYPE: PRT
<213> ORGANISM: Artificial Sequence
<220> FEATURE:

```
<223> OTHER INFORMATION: Synthetic peptide

<400> SEQUENCE: 63

Trp Tyr Leu Gln Lys Pro Gly Gln Pro Pro Gln Leu Leu Ile Tyr
1               5                   10                  15

<210> SEQ ID NO 64
<211> LENGTH: 23
<212> TYPE: PRT
<213> ORGANISM: Artificial Sequence
<220> FEATURE:
<223> OTHER INFORMATION: Synthetic peptide

<400> SEQUENCE: 64

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 65
<211> LENGTH: 23
<212> TYPE: PRT
<213> ORGANISM: Artificial Sequence
<220> FEATURE:
<223> OTHER INFORMATION: Synthetic peptide

<400> SEQUENCE: 65

Asp Ile Val Met Thr Gln Thr Pro Leu Ser Ser Pro Val Thr Leu Gly
1               5                   10                  15

Gln Pro Ala Ser Ile Ser Cys
            20

<210> SEQ ID NO 66
<211> LENGTH: 15
<212> TYPE: PRT
<213> ORGANISM: Artificial Sequence
<220> FEATURE:
<223> OTHER INFORMATION: Synthetic peptide

<400> SEQUENCE: 66

Trp Leu Gln Gln Arg Pro Gly Gln Pro Pro Arg Leu Leu Ile Tyr
1               5                   10                  15

<210> SEQ ID NO 67
<211> LENGTH: 23
<212> TYPE: PRT
<213> ORGANISM: Artificial Sequence
<220> FEATURE:
<223> OTHER INFORMATION: Synthetic peptide

<400> SEQUENCE: 67

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 68
<211> LENGTH: 15
<212> TYPE: PRT
<213> ORGANISM: Artificial Sequence
<220> FEATURE:
<223> OTHER INFORMATION: Synthetic peptide

<400> SEQUENCE: 68

Trp Tyr Gln Gln Lys Pro Gly Gln Ala Pro Arg Leu Leu Ile Tyr
1               5                   10                  15
```

```
<210> SEQ ID NO 69
<211> LENGTH: 23
<212> TYPE: PRT
<213> ORGANISM: Artificial Sequence
<220> FEATURE:
<223> OTHER INFORMATION: Synthetic peptide

<400> SEQUENCE: 69

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 70
<211> LENGTH: 15
<212> TYPE: PRT
<213> ORGANISM: Artificial Sequence
<220> FEATURE:
<223> OTHER INFORMATION: Synthetic peptide

<400> SEQUENCE: 70

Trp Tyr Gln Gln Lys Pro Gly Leu Ala Pro Arg Leu Leu Ile Tyr
1               5                   10                  15

<210> SEQ ID NO 71
<211> LENGTH: 23
<212> TYPE: PRT
<213> ORGANISM: Artificial Sequence
<220> FEATURE:
<223> OTHER INFORMATION: Synthetic peptide

<400> SEQUENCE: 71

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 72
<211> LENGTH: 23
<212> TYPE: PRT
<213> ORGANISM: Artificial Sequence
<220> FEATURE:
<223> OTHER INFORMATION: Synthetic peptide

<400> SEQUENCE: 72

Glu Ile Val Met Thr Gln Ser Pro Ala Thr Leu Ser Leu Ser Pro Gly
1               5                   10                  15

Glu Arg Ala Thr Leu Ser Cys
            20

<210> SEQ ID NO 73
<211> LENGTH: 23
<212> TYPE: PRT
<213> ORGANISM: Artificial Sequence
<220> FEATURE:
<223> OTHER INFORMATION: Synthetic peptide

<400> SEQUENCE: 73

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 74
```

```
<211> LENGTH: 15
<212> TYPE: PRT
<213> ORGANISM: Artificial Sequence
<220> FEATURE:
<223> OTHER INFORMATION: Synthetic peptide

<400> SEQUENCE: 74

Trp Tyr Gln Gln Lys Pro Gly Gln Pro Pro Lys Leu Leu Ile Tyr
1               5                   10                  15

<210> SEQ ID NO 75
<211> LENGTH: 23
<212> TYPE: PRT
<213> ORGANISM: Artificial Sequence
<220> FEATURE:
<223> OTHER INFORMATION: Synthetic peptide

<400> SEQUENCE: 75

Glu Thr Thr Leu Thr Gln Ser Pro Ala Phe Met Ser Ala Thr Pro Gly
1               5                   10                  15

Asp Lys Val Asn Ile Ser Cys
            20

<210> SEQ ID NO 76
<211> LENGTH: 15
<212> TYPE: PRT
<213> ORGANISM: Artificial Sequence
<220> FEATURE:
<223> OTHER INFORMATION: Synthetic peptide

<400> SEQUENCE: 76

Trp Tyr Gln Gln Lys Pro Gly Glu Ala Ala Ile Phe Ile Ile Gln
1               5                   10                  15

<210> SEQ ID NO 77
<211> LENGTH: 23
<212> TYPE: PRT
<213> ORGANISM: Artificial Sequence
<220> FEATURE:
<223> OTHER INFORMATION: Synthetic peptide

<400> SEQUENCE: 77

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 78
<211> LENGTH: 15
<212> TYPE: PRT
<213> ORGANISM: Artificial Sequence
<220> FEATURE:
<223> OTHER INFORMATION: Synthetic peptide

<400> SEQUENCE: 78

Trp Tyr Gln Gln Lys Pro Asp Gln Ser Pro Lys Leu Leu Ile Lys
1               5                   10                  15

<210> SEQ ID NO 79
<211> LENGTH: 23
<212> TYPE: PRT
<213> ORGANISM: Artificial Sequence
<220> FEATURE:
<223> OTHER INFORMATION: Synthetic peptide

<400> SEQUENCE: 79

Asp Val Val Met Thr Gln Ser Pro Ala Phe Leu Ser Val Thr Pro Gly
```

```
                1               5                  10                  15

Glu Lys Val Thr Ile Thr Cys
                20

<210> SEQ ID NO 80
<211> LENGTH: 15
<212> TYPE: PRT
<213> ORGANISM: Artificial Sequence
<220> FEATURE:
<223> OTHER INFORMATION: Synthetic peptide

<400> SEQUENCE: 80

Trp Tyr Gln Gln Lys Pro Asp Gln Ala Pro Lys Leu Leu Ile Lys
1               5                  10                  15

<210> SEQ ID NO 81
<211> LENGTH: 32
<212> TYPE: PRT
<213> ORGANISM: Artificial Sequence
<220> FEATURE:
<223> OTHER INFORMATION: Synthetic peptide

<400> SEQUENCE: 81

Gly Val Pro Ser Arg Phe Ser Gly Ser Gly Ser Gly Thr Asp Phe Thr
1               5                  10                  15

Leu Thr Ile Ser Ser Leu Gln Pro Glu Asp Phe Ala Thr Tyr Tyr Cys
                20                  25                  30

<210> SEQ ID NO 82
<211> LENGTH: 32
<212> TYPE: PRT
<213> ORGANISM: Artificial Sequence
<220> FEATURE:
<223> OTHER INFORMATION: Synthetic peptide

<400> SEQUENCE: 82

Gly Val Pro Ser Arg Phe Ser Gly Ser Gly Ser Gly Thr Asp Phe Thr
1               5                  10                  15

Phe Thr Ile Ser Ser Leu Gln Pro Glu Asp Ile Ala Thr Tyr Tyr Cys
                20                  25                  30

<210> SEQ ID NO 83
<211> LENGTH: 32
<212> TYPE: PRT
<213> ORGANISM: Artificial Sequence
<220> FEATURE:
<223> OTHER INFORMATION: Synthetic peptide

<400> SEQUENCE: 83

Gly Val Pro Ser Arg Phe Ser Gly Ser Gly Ser Gly Thr Asp Phe Thr
1               5                  10                  15

Leu Thr Ile Ser Ser Leu Gln Pro Glu Asp Val Ala Thr Tyr Tyr Cys
                20                  25                  30

<210> SEQ ID NO 84
<211> LENGTH: 32
<212> TYPE: PRT
<213> ORGANISM: Artificial Sequence
<220> FEATURE:
<223> OTHER INFORMATION: Synthetic peptide

<400> SEQUENCE: 84

Gly Val Pro Ser Arg Phe Ser Gly Ser Gly Ser Gly Thr Glu Phe Thr
1               5                  10                  15

Leu Thr Ile Ser Ser Leu Gln Pro Glu Asp Phe Ala Thr Tyr Tyr Cys
```

<210> SEQ ID NO 85
<211> LENGTH: 32
<212> TYPE: PRT
<213> ORGANISM: Artificial Sequence
<220> FEATURE:
<223> OTHER INFORMATION: Synthetic peptide

<400> SEQUENCE: 85

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 86
<211> LENGTH: 32
<212> TYPE: PRT
<213> ORGANISM: Artificial Sequence
<220> FEATURE:
<223> OTHER INFORMATION: Synthetic peptide

<400> SEQUENCE: 86

Gly Val Pro Ser Arg Phe Ser Gly Ser Gly Ser Gly Thr Asp Phe Thr
1               5                   10                  15

Leu Thr Ile Ser Cys Leu Gln Ser Glu Asp Phe Ala Thr Tyr Tyr Cys
            20                  25                  30

<210> SEQ ID NO 87
<211> LENGTH: 32
<212> TYPE: PRT
<213> ORGANISM: Artificial Sequence
<220> FEATURE:
<223> OTHER INFORMATION: Synthetic peptide

<400> SEQUENCE: 87

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 88
<211> LENGTH: 32
<212> TYPE: PRT
<213> ORGANISM: Artificial Sequence
<220> FEATURE:
<223> OTHER INFORMATION: Synthetic peptide

<400> SEQUENCE: 88

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 89
<211> LENGTH: 32
<212> TYPE: PRT
<213> ORGANISM: Artificial Sequence
<220> FEATURE:
<223> OTHER INFORMATION: Synthetic peptide

<400> SEQUENCE: 89

Gly Val Pro Asp Arg Phe Ser Gly Ser Gly Ala Gly Thr Asp Phe Thr
1               5                   10                  15

Leu Lys Ile Ser Arg Val Glu Ala Glu Asp Val Gly Val Tyr Tyr Cys

```
                20                  25                  30

<210> SEQ ID NO 90
<211> LENGTH: 32
<212> TYPE: PRT
<213> ORGANISM: Artificial Sequence
<220> FEATURE:
<223> OTHER INFORMATION: Synthetic peptide

<400> SEQUENCE: 90

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 91
<211> LENGTH: 32
<212> TYPE: PRT
<213> ORGANISM: Artificial Sequence
<220> FEATURE:
<223> OTHER INFORMATION: Synthetic peptide

<400> SEQUENCE: 91

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 92
<211> LENGTH: 32
<212> TYPE: PRT
<213> ORGANISM: Artificial Sequence
<220> FEATURE:
<223> OTHER INFORMATION: Synthetic peptide

<400> SEQUENCE: 92

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 93
<211> LENGTH: 32
<212> TYPE: PRT
<213> ORGANISM: Artificial Sequence
<220> FEATURE:
<223> OTHER INFORMATION: Synthetic peptide

<400> SEQUENCE: 93

Gly Ile Pro Ala Arg Phe Ser Gly Ser Gly Pro Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 94
<211> LENGTH: 32
<212> TYPE: PRT
<213> ORGANISM: Artificial Sequence
<220> FEATURE:
<223> OTHER INFORMATION: Synthetic peptide

<400> SEQUENCE: 94

Gly Ile Pro Ala Arg Phe Ser Gly Ser Gly Ser Gly Thr Asp Phe Thr
1               5                   10                  15

Leu Thr Ile Ser Ser Leu Gln Pro Glu Asp Phe Ala Val Tyr Tyr Cys
```

<210> SEQ ID NO 95
<211> LENGTH: 32
<212> TYPE: PRT
<213> ORGANISM: Artificial Sequence
<220> FEATURE:
<223> OTHER INFORMATION: Synthetic peptide

<400> SEQUENCE: 95

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 96
<211> LENGTH: 32
<212> TYPE: PRT
<213> ORGANISM: Artificial Sequence
<220> FEATURE:
<223> OTHER INFORMATION: Synthetic peptide

<400> SEQUENCE: 96

Gly Ile Pro Pro Arg Phe Ser Gly Ser Gly Tyr Gly Thr Asp Phe Thr
1               5                   10                  15

Leu Thr Ile Asn Asn Ile Glu Ser Glu Asp Ala Ala Tyr Tyr Phe Cys
            20                  25                  30

<210> SEQ ID NO 97
<211> LENGTH: 32
<212> TYPE: PRT
<213> ORGANISM: Artificial Sequence
<220> FEATURE:
<223> OTHER INFORMATION: Synthetic peptide

<400> SEQUENCE: 97

Gly Val Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Thr Tyr Tyr Cys
            20                  25                  30

<210> SEQ ID NO 98
<211> LENGTH: 32
<212> TYPE: PRT
<213> ORGANISM: Artificial Sequence
<220> FEATURE:
<223> OTHER INFORMATION: Synthetic peptide

<400> SEQUENCE: 98

Gly Val Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys
            20                  25                  30

<210> SEQ ID NO 99
<211> LENGTH: 22
<212> TYPE: PRT
<213> ORGANISM: Artificial Sequence
<220> FEATURE:
<223> OTHER INFORMATION: Synthetic peptide

<400> SEQUENCE: 99

Gln Ser Val Leu Thr Gln Pro Pro Ser Val Ser Glu Ala Pro Arg Gln
1               5                   10                  15

Arg Val Thr Ile Ser Cys

20

<210> SEQ ID NO 100
<211> LENGTH: 15
<212> TYPE: PRT
<213> ORGANISM: Artificial Sequence
<220> FEATURE:
<223> OTHER INFORMATION: Synthetic peptide

<400> SEQUENCE: 100

Trp Tyr Gln Gln Leu Pro Gly Lys Ala Pro Lys Leu Leu Ile Tyr
1               5                   10                  15

<210> SEQ ID NO 101
<211> LENGTH: 22
<212> TYPE: PRT
<213> ORGANISM: Artificial Sequence
<220> FEATURE:
<223> OTHER INFORMATION: Synthetic peptide

<400> SEQUENCE: 101

Gln Ser Val Leu Thr Gln Pro Pro Ser Val Ser Gly Ala Pro Gly Gln
1               5                   10                  15

Arg Val Thr Ile Ser Cys
            20

<210> SEQ ID NO 102
<211> LENGTH: 15
<212> TYPE: PRT
<213> ORGANISM: Artificial Sequence
<220> FEATURE:
<223> OTHER INFORMATION: Synthetic peptide

<400> SEQUENCE: 102

Trp Tyr Gln Gln Leu Pro Gly Thr Ala Pro Lys Leu Leu Ile Tyr
1               5                   10                  15

<210> SEQ ID NO 103
<211> LENGTH: 22
<212> TYPE: PRT
<213> ORGANISM: Artificial Sequence
<220> FEATURE:
<223> OTHER INFORMATION: Synthetic peptide

<400> SEQUENCE: 103

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 104
<211> LENGTH: 22
<212> TYPE: PRT
<213> ORGANISM: Artificial Sequence
<220> FEATURE:
<223> OTHER INFORMATION: Synthetic peptide

<400> SEQUENCE: 104

Gln Ser Val Leu Thr Gln Pro Pro Ser Val Ser Ala Ala Pro Gly Gln
1               5                   10                  15

Lys Val Thr Ile Ser Cys
            20

<210> SEQ ID NO 105
<211> LENGTH: 22
<212> TYPE: PRT

<213> ORGANISM: Artificial Sequence
<220> FEATURE:
<223> OTHER INFORMATION: Synthetic peptide

<400> SEQUENCE: 105

Gln Ser Ala Leu Thr Gln Pro Pro Ser Ala Ser Gly Ser Pro Gly Gln
1               5                   10                  15

Ser Val Thr Ile Ser Cys
            20

<210> SEQ ID NO 106
<211> LENGTH: 15
<212> TYPE: PRT
<213> ORGANISM: Artificial Sequence
<220> FEATURE:
<223> OTHER INFORMATION: Synthetic peptide

<400> SEQUENCE: 106

Trp Tyr Gln Gln His Pro Gly Lys Ala Pro Lys Leu Met Ile Tyr
1               5                   10                  15

<210> SEQ ID NO 107
<211> LENGTH: 22
<212> TYPE: PRT
<213> ORGANISM: Artificial Sequence
<220> FEATURE:
<223> OTHER INFORMATION: Synthetic peptide

<400> SEQUENCE: 107

Gln Ser Ala Leu Thr Gln Pro Arg Ser Val Ser Gly Ser Pro Gly Gln
1               5                   10                  15

Ser Val Thr Ile Ser Cys
            20

<210> SEQ ID NO 108
<211> LENGTH: 22
<212> TYPE: PRT
<213> ORGANISM: Artificial Sequence
<220> FEATURE:
<223> OTHER INFORMATION: Synthetic peptide

<400> SEQUENCE: 108

Gln Ser Ala Leu Thr Gln Pro Ala Ser Val Ser Gly Ser Pro Gly Gln
1               5                   10                  15

Ser Ile Thr Ile Ser Cys
            20

<210> SEQ ID NO 109
<211> LENGTH: 22
<212> TYPE: PRT
<213> ORGANISM: Artificial Sequence
<220> FEATURE:
<223> OTHER INFORMATION: Synthetic peptide

<400> SEQUENCE: 109

Gln Ser Ala Leu Thr Gln Pro Pro Ser Val Ser Gly Ser Pro Gly Gln
1               5                   10                  15

Ser Val Thr Ile Ser Cys
            20

<210> SEQ ID NO 110
<211> LENGTH: 15
<212> TYPE: PRT
<213> ORGANISM: Artificial Sequence
<220> FEATURE:
<223> OTHER INFORMATION: Synthetic peptide

```
<400> SEQUENCE: 110

Trp Tyr Gln Gln Pro Pro Gly Thr Ala Pro Lys Leu Met Ile Tyr
1               5                   10                  15

<210> SEQ ID NO 111
<211> LENGTH: 22
<212> TYPE: PRT
<213> ORGANISM: Artificial Sequence
<220> FEATURE:
<223> OTHER INFORMATION: Synthetic peptide

<400> SEQUENCE: 111

Ser Tyr Glu Leu Thr Gln Pro Pro Ser Val Ser Val Ser Pro Gly Gln
1               5                   10                  15

Thr Ala Ser Ile Thr Cys
            20

<210> SEQ ID NO 112
<211> LENGTH: 15
<212> TYPE: PRT
<213> ORGANISM: Artificial Sequence
<220> FEATURE:
<223> OTHER INFORMATION: Synthetic peptide

<400> SEQUENCE: 112

Trp Tyr Gln Gln Lys Pro Gly Gln Ser Pro Val Leu Val Ile Tyr
1               5                   10                  15

<210> SEQ ID NO 113
<211> LENGTH: 22
<212> TYPE: PRT
<213> ORGANISM: Artificial Sequence
<220> FEATURE:
<223> OTHER INFORMATION: Synthetic peptide

<400> SEQUENCE: 113

Ser Tyr Glu Leu Thr Gln Pro Leu Ser Val Ser Val Ala Leu Gly Gln
1               5                   10                  15

Thr Ala Arg Ile Thr Cys
            20

<210> SEQ ID NO 114
<211> LENGTH: 15
<212> TYPE: PRT
<213> ORGANISM: Artificial Sequence
<220> FEATURE:
<223> OTHER INFORMATION: Synthetic peptide

<400> SEQUENCE: 114

Trp Tyr Gln Gln Lys Pro Gly Gln Ala Pro Val Leu Val Ile Tyr
1               5                   10                  15

<210> SEQ ID NO 115
<211> LENGTH: 22
<212> TYPE: PRT
<213> ORGANISM: Artificial Sequence
<220> FEATURE:
<223> OTHER INFORMATION: Synthetic peptide

<400> SEQUENCE: 115

Ser Tyr Glu Leu Thr Gln Pro Pro Ser Val Ser Val Ser Pro Gly Gln
1               5                   10                  15

Thr Ala Arg Ile Thr Cys
            20
```

```
<210> SEQ ID NO 116
<211> LENGTH: 15
<212> TYPE: PRT
<213> ORGANISM: Artificial Sequence
<220> FEATURE:
<223> OTHER INFORMATION: Synthetic peptide

<400> SEQUENCE: 116

Trp Tyr Gln Gln Lys Ser Gly Gln Ala Pro Val Leu Val Ile Tyr
1               5                   10                  15

<210> SEQ ID NO 117
<211> LENGTH: 22
<212> TYPE: PRT
<213> ORGANISM: Artificial Sequence
<220> FEATURE:
<223> OTHER INFORMATION: Synthetic peptide

<400> SEQUENCE: 117

Ser Tyr Glu Leu Thr Gln Pro Pro Ser Val Ser Val Ser Leu Gly Gln
1               5                   10                  15

Met Ala Arg Ile Thr Cys
            20

<210> SEQ ID NO 118
<211> LENGTH: 15
<212> TYPE: PRT
<213> ORGANISM: Artificial Sequence
<220> FEATURE:
<223> OTHER INFORMATION: Synthetic peptide

<400> SEQUENCE: 118

Trp Tyr Gln Gln Lys Pro Gly Gln Phe Pro Val Leu Val Ile Tyr
1               5                   10                  15

<210> SEQ ID NO 119
<211> LENGTH: 22
<212> TYPE: PRT
<213> ORGANISM: Artificial Sequence
<220> FEATURE:
<223> OTHER INFORMATION: Synthetic peptide

<400> SEQUENCE: 119

Ser Ser Glu Leu Thr Gln Asp Pro Ala Val Ser Val Ala Leu Gly Gln
1               5                   10                  15

Thr Val Arg Ile Thr Cys
            20

<210> SEQ ID NO 120
<211> LENGTH: 22
<212> TYPE: PRT
<213> ORGANISM: Artificial Sequence
<220> FEATURE:
<223> OTHER INFORMATION: Synthetic peptide

<400> SEQUENCE: 120

Ser Tyr Val Leu Thr Gln Pro Pro Ser Val Ser Val Ala Pro Gly Lys
1               5                   10                  15

Thr Ala Arg Ile Thr Cys
            20

<210> SEQ ID NO 121
<211> LENGTH: 22
<212> TYPE: PRT
<213> ORGANISM: Artificial Sequence
<220> FEATURE:
```

<223> OTHER INFORMATION: Synthetic peptide

<400> SEQUENCE: 121

Ser Tyr Glu Leu Thr Gln Leu Pro Ser Val Ser Val Ser Pro Gly Gln
1               5                   10                  15

Thr Ala Arg Ile Thr Cys
            20

<210> SEQ ID NO 122
<211> LENGTH: 15
<212> TYPE: PRT
<213> ORGANISM: Artificial Sequence
<220> FEATURE:
<223> OTHER INFORMATION: Synthetic peptide

<400> SEQUENCE: 122

Trp Tyr Gln Gln Lys Pro Gly Gln Ala Pro Glu Leu Val Ile Tyr
1               5                   10                  15

<210> SEQ ID NO 123
<211> LENGTH: 22
<212> TYPE: PRT
<213> ORGANISM: Artificial Sequence
<220> FEATURE:
<223> OTHER INFORMATION: Synthetic peptide

<400> SEQUENCE: 123

Ser Tyr Glu Leu Met Gln Pro Pro Ser Val Ser Val Ser Pro Gly Gln
1               5                   10                  15

Thr Ala Arg Ile Thr Cys
            20

<210> SEQ ID NO 124
<211> LENGTH: 22
<212> TYPE: PRT
<213> ORGANISM: Artificial Sequence
<220> FEATURE:
<223> OTHER INFORMATION: Synthetic peptide

<400> SEQUENCE: 124

Ser Tyr Glu Leu Thr Gln Pro Ser Ser Val Ser Val Ser Pro Gly Gln
1               5                   10                  15

Thr Ala Arg Ile Thr Cys
            20

<210> SEQ ID NO 125
<211> LENGTH: 15
<212> TYPE: PRT
<213> ORGANISM: Artificial Sequence
<220> FEATURE:
<223> OTHER INFORMATION: Synthetic peptide

<400> SEQUENCE: 125

Trp Phe Gln Gln Lys Pro Gly Gln Ala Pro Val Leu Val Ile Tyr
1               5                   10                  15

<210> SEQ ID NO 126
<211> LENGTH: 22
<212> TYPE: PRT
<213> ORGANISM: Artificial Sequence
<220> FEATURE:
<223> OTHER INFORMATION: Synthetic peptide

<400> SEQUENCE: 126

Leu Pro Val Leu Thr Gln Pro Pro Ser Ala Ser Ala Leu Leu Gly Ala
1               5                   10                  15

```
Ser Ile Lys Leu Thr Cys
            20

<210> SEQ ID NO 127
<211> LENGTH: 15
<212> TYPE: PRT
<213> ORGANISM: Artificial Sequence
<220> FEATURE:
<223> OTHER INFORMATION: Synthetic peptide

<400> SEQUENCE: 127

Trp Tyr Gln Gln Arg Pro Gly Arg Ser Pro Gln Tyr Ile Met Lys
1               5                   10                  15

<210> SEQ ID NO 128
<211> LENGTH: 22
<212> TYPE: PRT
<213> ORGANISM: Artificial Sequence
<220> FEATURE:
<223> OTHER INFORMATION: Synthetic peptide

<400> SEQUENCE: 128

Gln Pro Val Leu Thr Gln Ser Ser Ser Ala Ser Ala Ser Leu Gly Ser
1               5                   10                  15

Ser Val Lys Leu Thr Cys
            20

<210> SEQ ID NO 129
<211> LENGTH: 15
<212> TYPE: PRT
<213> ORGANISM: Artificial Sequence
<220> FEATURE:
<223> OTHER INFORMATION: Synthetic peptide

<400> SEQUENCE: 129

Trp His Gln Gln Gln Pro Gly Lys Ala Pro Arg Tyr Leu Met Lys
1               5                   10                  15

<210> SEQ ID NO 130
<211> LENGTH: 22
<212> TYPE: PRT
<213> ORGANISM: Artificial Sequence
<220> FEATURE:
<223> OTHER INFORMATION: Synthetic peptide

<400> SEQUENCE: 130

Gln Leu Val Leu Thr Gln Ser Pro Ser Ala Ser Ala Ser Leu Gly Ala
1               5                   10                  15

Ser Val Lys Leu Thr Cys
            20

<210> SEQ ID NO 131
<211> LENGTH: 15
<212> TYPE: PRT
<213> ORGANISM: Artificial Sequence
<220> FEATURE:
<223> OTHER INFORMATION: Synthetic peptide

<400> SEQUENCE: 131

Trp His Gln Gln Gln Pro Glu Lys Gly Pro Arg Tyr Leu Met Lys
1               5                   10                  15

<210> SEQ ID NO 132
<211> LENGTH: 22
<212> TYPE: PRT
<213> ORGANISM: Artificial Sequence
```

```
<220> FEATURE:
<223> OTHER INFORMATION: Synthetic peptide

<400> SEQUENCE: 132

Gln Pro Val Leu Thr Gln Pro Pro Ser Ser Ala Ser Pro Gly Glu
1               5                   10                  15

Ser Ala Arg Leu Thr Cys
            20

<210> SEQ ID NO 133
<211> LENGTH: 15
<212> TYPE: PRT
<213> ORGANISM: Artificial Sequence
<220> FEATURE:
<223> OTHER INFORMATION: Synthetic peptide

<400> SEQUENCE: 133

Trp Tyr Gln Gln Lys Pro Gly Ser Pro Pro Arg Tyr Leu Leu Tyr
1               5                   10                  15

<210> SEQ ID NO 134
<211> LENGTH: 22
<212> TYPE: PRT
<213> ORGANISM: Artificial Sequence
<220> FEATURE:
<223> OTHER INFORMATION: Synthetic peptide

<400> SEQUENCE: 134

Gln Ala Val Leu Thr Gln Pro Ala Ser Leu Ser Ala Ser Pro Gly Ala
1               5                   10                  15

Ser Ala Ser Leu Thr Cys
            20

<210> SEQ ID NO 135
<211> LENGTH: 15
<212> TYPE: PRT
<213> ORGANISM: Artificial Sequence
<220> FEATURE:
<223> OTHER INFORMATION: Synthetic peptide

<400> SEQUENCE: 135

Trp Tyr Gln Gln Lys Pro Gly Ser Pro Pro Gln Tyr Leu Leu Arg
1               5                   10                  15

<210> SEQ ID NO 136
<211> LENGTH: 22
<212> TYPE: PRT
<213> ORGANISM: Artificial Sequence
<220> FEATURE:
<223> OTHER INFORMATION: Synthetic peptide

<400> SEQUENCE: 136

Gln Pro Val Leu Thr Gln Pro Ser Ser His Ser Ala Ser Ser Gly Ala
1               5                   10                  15

Ser Val Arg Leu Thr Cys
            20

<210> SEQ ID NO 137
<211> LENGTH: 15
<212> TYPE: PRT
<213> ORGANISM: Artificial Sequence
<220> FEATURE:
<223> OTHER INFORMATION: Synthetic peptide

<400> SEQUENCE: 137

Trp Tyr Gln Gln Lys Pro Gly Asn Pro Pro Arg Tyr Leu Leu Tyr
```

<210> SEQ ID NO 138
<211> LENGTH: 22
<212> TYPE: PRT
<213> ORGANISM: Artificial Sequence
<220> FEATURE:
<223> OTHER INFORMATION: Synthetic peptide

<400> SEQUENCE: 138

Asn Phe Met Leu Thr Gln Pro His Ser Val Ser Glu Ser Pro Gly Lys
1               5                   10                  15

Thr Val Thr Ile Ser Cys
            20

<210> SEQ ID NO 139
<211> LENGTH: 15
<212> TYPE: PRT
<213> ORGANISM: Artificial Sequence
<220> FEATURE:
<223> OTHER INFORMATION: Synthetic peptide

<400> SEQUENCE: 139

Trp Tyr Gln Gln Arg Pro Gly Ser Ser Pro Thr Thr Val Ile Tyr
1               5                   10                  15

<210> SEQ ID NO 140
<211> LENGTH: 22
<212> TYPE: PRT
<213> ORGANISM: Artificial Sequence
<220> FEATURE:
<223> OTHER INFORMATION: Synthetic peptide

<400> SEQUENCE: 140

Gln Thr Val Val Thr Gln Glu Pro Ser Leu Thr Val Ser Pro Gly Gly
1               5                   10                  15

Thr Val Thr Leu Thr Cys
            20

<210> SEQ ID NO 141
<211> LENGTH: 15
<212> TYPE: PRT
<213> ORGANISM: Artificial Sequence
<220> FEATURE:
<223> OTHER INFORMATION: Synthetic peptide

<400> SEQUENCE: 141

Trp Phe Gln Gln Lys Pro Gly Gln Ala Pro Arg Ala Leu Ile Tyr
1               5                   10                  15

<210> SEQ ID NO 142
<211> LENGTH: 22
<212> TYPE: PRT
<213> ORGANISM: Artificial Sequence
<220> FEATURE:
<223> OTHER INFORMATION: Synthetic peptide

<400> SEQUENCE: 142

Gln Ala Val Val Thr Gln Glu Pro Ser Leu Thr Val Ser Pro Gly Gly
1               5                   10                  15

Thr Val Thr Leu Thr Cys
            20

<210> SEQ ID NO 143
<211> LENGTH: 15
<212> TYPE: PRT

```
<213> ORGANISM: Artificial Sequence
<220> FEATURE:
<223> OTHER INFORMATION: Synthetic peptide

<400> SEQUENCE: 143

Trp Phe Gln Gln Lys Pro Gly Gln Ala Pro Arg Thr Leu Ile Tyr
1               5                   10                  15

<210> SEQ ID NO 144
<211> LENGTH: 22
<212> TYPE: PRT
<213> ORGANISM: Artificial Sequence
<220> FEATURE:
<223> OTHER INFORMATION: Synthetic peptide

<400> SEQUENCE: 144

Gln Thr Val Val Thr Gln Glu Pro Ser Phe Ser Val Ser Pro Gly Gly
1               5                   10                  15

Thr Val Thr Leu Thr Cys
            20

<210> SEQ ID NO 145
<211> LENGTH: 15
<212> TYPE: PRT
<213> ORGANISM: Artificial Sequence
<220> FEATURE:
<223> OTHER INFORMATION: Synthetic peptide

<400> SEQUENCE: 145

Trp Tyr Gln Gln Thr Pro Gly Gln Ala Pro Arg Thr Leu Ile Tyr
1               5                   10                  15

<210> SEQ ID NO 146
<211> LENGTH: 22
<212> TYPE: PRT
<213> ORGANISM: Artificial Sequence
<220> FEATURE:
<223> OTHER INFORMATION: Synthetic peptide

<400> SEQUENCE: 146

Gln Pro Val Leu Thr Gln Pro Pro Ser Ala Ser Ala Ser Leu Gly Ala
1               5                   10                  15

Ser Val Thr Leu Thr Cys
            20

<210> SEQ ID NO 147
<211> LENGTH: 15
<212> TYPE: PRT
<213> ORGANISM: Artificial Sequence
<220> FEATURE:
<223> OTHER INFORMATION: Synthetic peptide

<400> SEQUENCE: 147

Trp Tyr Gln Gln Arg Pro Gly Lys Gly Pro Arg Phe Val Met Arg
1               5                   10                  15

<210> SEQ ID NO 148
<211> LENGTH: 22
<212> TYPE: PRT
<213> ORGANISM: Artificial Sequence
<220> FEATURE:
<223> OTHER INFORMATION: Synthetic peptide

<400> SEQUENCE: 148

Gln Ala Gly Leu Thr Gln Pro Pro Ser Val Ser Lys Gly Leu Arg Gln
1               5                   10                  15
```

```
Thr Ala Thr Leu Thr Cys
            20

<210> SEQ ID NO 149
<211> LENGTH: 15
<212> TYPE: PRT
<213> ORGANISM: Artificial Sequence
<220> FEATURE:
<223> OTHER INFORMATION: Synthetic peptide

<400> SEQUENCE: 149

Trp Leu Gln Gln His Gln Gly His Pro Pro Lys Leu Leu Ser Tyr
1               5                   10                  15

<210> SEQ ID NO 150
<211> LENGTH: 32
<212> TYPE: PRT
<213> ORGANISM: Artificial Sequence
<220> FEATURE:
<223> OTHER INFORMATION: Synthetic peptide

<400> SEQUENCE: 150

Gly Val Ser Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 151
<211> LENGTH: 32
<212> TYPE: PRT
<213> ORGANISM: Artificial Sequence
<220> FEATURE:
<223> OTHER INFORMATION: Synthetic peptide

<400> SEQUENCE: 151

Gly Val Pro Asp Arg Phe Ser Gly Ser Lys Ser Gly Thr Ser Ala Ser
1               5                   10                  15

Leu Ala Ile Thr Gly Leu Gln Ala Glu Asp Glu Ala Asp Tyr Tyr Cys
            20                  25                  30

<210> SEQ ID NO 152
<211> LENGTH: 32
<212> TYPE: PRT
<213> ORGANISM: Artificial Sequence
<220> FEATURE:
<223> OTHER INFORMATION: Synthetic peptide

<400> SEQUENCE: 152

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 153
<211> LENGTH: 32
<212> TYPE: PRT
<213> ORGANISM: Artificial Sequence
<220> FEATURE:
<223> OTHER INFORMATION: Synthetic peptide

<400> SEQUENCE: 153

Gly Val Pro Asp Arg Phe Ser Gly Ser Lys Ser Gly Thr Ser Ala Ser
1               5                   10                  15

Leu Ala Ile Ser Gly Leu Arg Ser Glu Asp Glu Ala Asp Tyr Tyr Cys
            20                  25                  30
```

<210> SEQ ID NO 154
<211> LENGTH: 32
<212> TYPE: PRT
<213> ORGANISM: Artificial Sequence
<220> FEATURE:
<223> OTHER INFORMATION: Synthetic peptide

<400> SEQUENCE: 154

Gly Ile Pro Asp Arg Phe Ser Gly Ser Lys Ser Gly Thr Ser Ala Thr
1               5                   10                  15

Leu Gly Ile Thr Gly Leu Gln Thr Gly Asp Glu Ala Asp Tyr Tyr Cys
            20                  25                  30

<210> SEQ ID NO 155
<211> LENGTH: 32
<212> TYPE: PRT
<213> ORGANISM: Artificial Sequence
<220> FEATURE:
<223> OTHER INFORMATION: Synthetic peptide

<400> SEQUENCE: 155

Gly Val Pro Asp Arg Phe Ser Gly Ser Lys Ser Gly Asn Thr Ala Ser
1               5                   10                  15

Leu Thr Val Ser Gly Leu Gln Ala Glu Asp Glu Ala Asp Tyr Tyr Cys
            20                  25                  30

<210> SEQ ID NO 156
<211> LENGTH: 32
<212> TYPE: PRT
<213> ORGANISM: Artificial Sequence
<220> FEATURE:
<223> OTHER INFORMATION: Synthetic peptide

<400> SEQUENCE: 156

Gly Val Pro Asp Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 157
<211> LENGTH: 32
<212> TYPE: PRT
<213> ORGANISM: Artificial Sequence
<220> FEATURE:
<223> OTHER INFORMATION: Synthetic peptide

<400> SEQUENCE: 157

Gly Val Ser Asn Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 158
<211> LENGTH: 32
<212> TYPE: PRT
<213> ORGANISM: Artificial Sequence
<220> FEATURE:
<223> OTHER INFORMATION: Synthetic peptide

<400> SEQUENCE: 158

Gly Ile Pro Glu Arg Phe Ser Gly Ser Asn Ser Gly Asn Thr Ala Thr
1               5                   10                  15

Leu Thr Ile Ser Gly Thr Gln Ala Met Asp Glu Ala Asp Tyr Tyr Cys
            20                  25                  30

<210> SEQ ID NO 159
<211> LENGTH: 32
<212> TYPE: PRT
<213> ORGANISM: Artificial Sequence
<220> FEATURE:
<223> OTHER INFORMATION: Synthetic peptide

<400> SEQUENCE: 159

Gly Ile Pro Glu Arg Phe Ser Gly Ser Asn Ser Gly Asn Thr Ala Thr
1               5                   10                  15

Leu Thr Ile Ser Arg Ala Gln Ala Gly Asp Glu Ala Asp Tyr Tyr Cys
            20                  25                  30

<210> SEQ ID NO 160
<211> LENGTH: 32
<212> TYPE: PRT
<213> ORGANISM: Artificial Sequence
<220> FEATURE:
<223> OTHER INFORMATION: Synthetic peptide

<400> SEQUENCE: 160

Gly Ile Pro Glu Arg Phe Ser Gly Ser Ser Ser Gly Thr Met Ala Thr
1               5                   10                  15

Leu Thr Ile Ser Gly Ala Gln Val Glu Asp Glu Ala Asp Tyr Tyr Cys
            20                  25                  30

<210> SEQ ID NO 161
<211> LENGTH: 32
<212> TYPE: PRT
<213> ORGANISM: Artificial Sequence
<220> FEATURE:
<223> OTHER INFORMATION: Synthetic peptide

<400> SEQUENCE: 161

Gly Ile Pro Glu Arg Phe Ser Gly Ser Ser Ser Gly Thr Ile Val Thr
1               5                   10                  15

Leu Thr Ile Ser Gly Val Gln Ala Glu Asp Glu Ala Asp Tyr Tyr Cys
            20                  25                  30

<210> SEQ ID NO 162
<211> LENGTH: 32
<212> TYPE: PRT
<213> ORGANISM: Artificial Sequence
<220> FEATURE:
<223> OTHER INFORMATION: Synthetic peptide

<400> SEQUENCE: 162

Gly Ile Pro Asp Arg Phe Ser Gly Ser Ser Ser Gly Asn Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 163
<211> LENGTH: 32
<212> TYPE: PRT
<213> ORGANISM: Artificial Sequence
<220> FEATURE:
<223> OTHER INFORMATION: Synthetic peptide

<400> SEQUENCE: 163

Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Tyr Tyr Cys
            20                  25                  30

<210> SEQ ID NO 164
<211> LENGTH: 32
<212> TYPE: PRT
<213> ORGANISM: Artificial Sequence
<220> FEATURE:
<223> OTHER INFORMATION: Synthetic peptide

<400> SEQUENCE: 164

Gly Ile Pro Glu Arg Phe Ser Gly Ser Thr Ser Gly Asn Thr Thr Thr
1               5                   10                  15

Leu Thr Ile Ser Arg Val Leu Thr Glu Asp Glu Ala Asp Tyr Tyr Cys
            20                  25                  30

<210> SEQ ID NO 165
<211> LENGTH: 32
<212> TYPE: PRT
<213> ORGANISM: Artificial Sequence
<220> FEATURE:
<223> OTHER INFORMATION: Synthetic peptide

<400> SEQUENCE: 165

Gly Ile Pro Glu Arg Phe Ser Gly Ser Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 166
<211> LENGTH: 32
<212> TYPE: PRT
<213> ORGANISM: Artificial Sequence
<220> FEATURE:
<223> OTHER INFORMATION: Synthetic peptide

<400> SEQUENCE: 166

Gly Ile Pro Glu Arg Phe Ser Gly Ser Ser Gly Thr Thr Val Thr
1               5                   10                  15

Leu Thr Ile Ser Gly Ala Gln Val Glu Asp Glu Ala Asp Tyr Tyr Cys
            20                  25                  30

<210> SEQ ID NO 167
<211> LENGTH: 32
<212> TYPE: PRT
<213> ORGANISM: Artificial Sequence
<220> FEATURE:
<223> OTHER INFORMATION: Synthetic peptide

<400> SEQUENCE: 167

Gly Ile Pro Asp Arg Phe Met Gly Ser Ser Gly Ala Asp Arg Tyr
1               5                   10                  15

Leu Thr Phe Ser Asn Leu Gln Ser Asp Asp Ala Glu Tyr His Cys
            20                  25                  30

<210> SEQ ID NO 168
<211> LENGTH: 32
<212> TYPE: PRT
<213> ORGANISM: Artificial Sequence
<220> FEATURE:
<223> OTHER INFORMATION: Synthetic peptide

<400> SEQUENCE: 168

Gly Val Pro Asp Arg Phe Ser Gly Ser Ser Gly Ala Asp Arg Tyr
1               5                   10                  15

Leu Thr Ile Ser Asn Leu Gln Leu Glu Asp Ala Asp Tyr Tyr Cys
            20                  25                  30

<210> SEQ ID NO 169
<211> LENGTH: 32
<212> TYPE: PRT
<213> ORGANISM: Artificial Sequence
<220> FEATURE:
<223> OTHER INFORMATION: Synthetic peptide

<400> SEQUENCE: 169

Gly Ile Pro Asp Arg Phe Ser Gly Ser Ser Gly Ala Glu Arg Tyr
1               5                   10                  15

Leu Thr Ile Ser Ser Leu Gln Ser Glu Asp Glu Ala Asp Tyr Tyr Cys
            20                  25                  30

<210> SEQ ID NO 170
<211> LENGTH: 34
<212> TYPE: PRT
<213> ORGANISM: Artificial Sequence
<220> FEATURE:
<223> OTHER INFORMATION: Synthetic peptide

<400> SEQUENCE: 170

Gly Val Pro Ser Arg Phe Ser Gly Ser Lys Asp Ala Ser Ala Asn Thr
1               5                   10                  15

Gly Ile Leu Leu Ile Ser Gly Leu Gln Ser Glu Asp Glu Ala Asp Tyr
            20                  25                  30

Tyr Cys

<210> SEQ ID NO 171
<211> LENGTH: 34
<212> TYPE: PRT
<213> ORGANISM: Artificial Sequence
<220> FEATURE:
<223> OTHER INFORMATION: Synthetic peptide

<400> SEQUENCE: 171

Gly Val Pro Ser Arg Phe Ser Gly Ser Lys Asp Ala Ser Ala Asn Ala
1               5                   10                  15

Gly Ile Leu Leu Ile Ser Gly Leu Gln Ser Glu Asp Glu Ala Asp Tyr
            20                  25                  30

Tyr Cys

<210> SEQ ID NO 172
<211> LENGTH: 34
<212> TYPE: PRT
<213> ORGANISM: Artificial Sequence
<220> FEATURE:
<223> OTHER INFORMATION: Synthetic peptide

<400> SEQUENCE: 172

Gly Val Pro Ser Arg Phe Ser Gly Ser Asn Asp Ala Ser Ala Asn Ala
1               5                   10                  15

Gly Ile Leu Arg Ile Ser Gly Leu Gln Pro Glu Asp Glu Ala Asp Tyr
            20                  25                  30

Tyr Cys

<210> SEQ ID NO 173
<211> LENGTH: 34
<212> TYPE: PRT
<213> ORGANISM: Artificial Sequence
<220> FEATURE:
<223> OTHER INFORMATION: Synthetic peptide

<400> SEQUENCE: 173

```
Gly Val Pro Asp Arg Phe Ser Gly Ser Ile Asp Ser Ser Asn Ser
1               5                   10                  15

Ala Ser Leu Thr Ile Ser Gly Leu Lys Thr Glu Asp Glu Ala Asp Tyr
            20                  25                  30

Tyr Cys
```

<210> SEQ ID NO 174
<211> LENGTH: 32
<212> TYPE: PRT
<213> ORGANISM: Artificial Sequence
<220> FEATURE:
<223> OTHER INFORMATION: Synthetic peptide

<400> SEQUENCE: 174

```
Trp Thr Pro Ala Arg Phe Ser Gly Ser Leu Leu Gly Gly Lys Ala Ala
1               5                   10                  15

Leu Thr Leu Ser Gly Val Gln Pro Glu Asp Glu Ala Glu Tyr Tyr Cys
            20                  25                  30
```

<210> SEQ ID NO 175
<211> LENGTH: 32
<212> TYPE: PRT
<213> ORGANISM: Artificial Sequence
<220> FEATURE:
<223> OTHER INFORMATION: Synthetic peptide

<400> SEQUENCE: 175

```
Trp Thr Pro Ala Arg Phe Ser Gly Ser Leu Leu Gly Gly Lys Ala Ala
1               5                   10                  15

Leu Thr Leu Ser Gly Ala Gln Pro Glu Asp Glu Ala Glu Tyr Tyr Cys
            20                  25                  30
```

<210> SEQ ID NO 176
<211> LENGTH: 32
<212> TYPE: PRT
<213> ORGANISM: Artificial Sequence
<220> FEATURE:
<223> OTHER INFORMATION: Synthetic peptide

<400> SEQUENCE: 176

```
Gly Val Pro Asp Arg Phe Ser Gly Ser Ile Leu Gly Asn Lys Ala Ala
1               5                   10                  15

Leu Thr Ile Thr Gly Ala Gln Ala Asp Asp Glu Ser Asp Tyr Tyr Cys
            20                  25                  30
```

<210> SEQ ID NO 177
<211> LENGTH: 32
<212> TYPE: PRT
<213> ORGANISM: Artificial Sequence
<220> FEATURE:
<223> OTHER INFORMATION: Synthetic peptide

<400> SEQUENCE: 177

```
Gly Ile Pro Asp Arg Phe Ser Val Leu Gly Ser Gly Leu Asn Arg Tyr
1               5                   10                  15

Leu Thr Ile Lys Asn Ile Gln Glu Glu Asp Glu Ser Asp Tyr His Cys
            20                  25                  30
```

<210> SEQ ID NO 178
<211> LENGTH: 32
<212> TYPE: PRT
<213> ORGANISM: Artificial Sequence
<220> FEATURE:
<223> OTHER INFORMATION: Synthetic peptide

```
<400> SEQUENCE: 178

Gly Ile Ser Glu Arg Leu Ser Ala Ser Arg Gly Asn Thr Ala Ser
1               5                   10                  15

Leu Thr Ile Thr Gly Leu Gln Pro Glu Asp Glu Ala Asp Tyr Tyr Cys
            20                  25                  30

<210> SEQ ID NO 179
<211> LENGTH: 30
<212> TYPE: PRT
<213> ORGANISM: Artificial Sequence
<220> FEATURE:
<223> OTHER INFORMATION: Synthetic peptide

<400> SEQUENCE: 179

Gln Val Gln Leu Val Gln Ser Gly Ala Glu Val Lys Lys Phe Gly Ala
1               5                   10                  15

Ser Val Lys Val Ser Cys Lys Ala Ser Gly Tyr Thr Phe Thr
            20                  25                  30

<210> SEQ ID NO 180
<211> LENGTH: 14
<212> TYPE: PRT
<213> ORGANISM: Artificial Sequence
<220> FEATURE:
<223> OTHER INFORMATION: Synthetic peptide

<400> SEQUENCE: 180

Trp Val Arg Gln Ala Pro Gly Gln Gly Leu Glu Trp Met Gly
1               5                   10

<210> SEQ ID NO 181
<211> LENGTH: 14
<212> TYPE: PRT
<213> ORGANISM: Artificial Sequence
<220> FEATURE:
<223> OTHER INFORMATION: Synthetic peptide

<400> SEQUENCE: 181

Trp Val Arg Gln Ala Pro Gly Gln Arg Leu Glu Trp Met Gly
1               5                   10

<210> SEQ ID NO 182
<211> LENGTH: 14
<212> TYPE: PRT
<213> ORGANISM: Artificial Sequence
<220> FEATURE:
<223> OTHER INFORMATION: Synthetic peptide

<400> SEQUENCE: 182

Trp Val Arg Gln Ala Thr Gly Gln Gly Leu Glu Trp Met Gly
1               5                   10

<210> SEQ ID NO 183
<211> LENGTH: 30
<212> TYPE: PRT
<213> ORGANISM: Artificial Sequence
<220> FEATURE:
<223> OTHER INFORMATION: Synthetic peptide

<400> SEQUENCE: 183

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr
            20                  25                  30
```

```
<210> SEQ ID NO 184
<211> LENGTH: 14
<212> TYPE: PRT
<213> ORGANISM: Artificial Sequence
<220> FEATURE:
<223> OTHER INFORMATION: Synthetic peptide

<400> SEQUENCE: 184

Trp Val Arg Gln Ala Pro Gly Lys Gly Leu Glu Trp Met Gly
1               5                   10

<210> SEQ ID NO 185
<211> LENGTH: 30
<212> TYPE: PRT
<213> ORGANISM: Artificial Sequence
<220> FEATURE:
<223> OTHER INFORMATION: Synthetic peptide

<400> SEQUENCE: 185

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr
            20                  25                  30

<210> SEQ ID NO 186
<211> LENGTH: 14
<212> TYPE: PRT
<213> ORGANISM: Artificial Sequence
<220> FEATURE:
<223> OTHER INFORMATION: Synthetic peptide

<400> SEQUENCE: 186

Trp Val Arg Gln Ala Pro Gly Gln Ala Leu Glu Trp Met Gly
1               5                   10

<210> SEQ ID NO 187
<211> LENGTH: 30
<212> TYPE: PRT
<213> ORGANISM: Artificial Sequence
<220> FEATURE:
<223> OTHER INFORMATION: Synthetic peptide

<400> SEQUENCE: 187

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr
            20                  25                  30

<210> SEQ ID NO 188
<211> LENGTH: 14
<212> TYPE: PRT
<213> ORGANISM: Artificial Sequence
<220> FEATURE:
<223> OTHER INFORMATION: Synthetic peptide

<400> SEQUENCE: 188

Trp Val Arg Gln Ala Arg Gly Gln Arg Leu Glu Trp Ile Gly
1               5                   10

<210> SEQ ID NO 189
<211> LENGTH: 30
<212> TYPE: PRT
<213> ORGANISM: Artificial Sequence
<220> FEATURE:
<223> OTHER INFORMATION: Synthetic peptide

<400> SEQUENCE: 189
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 190
<211> LENGTH: 30
<212> TYPE: PRT
<213> ORGANISM: Artificial Sequence
<220> FEATURE:
<223> OTHER INFORMATION: Synthetic peptide

<400> SEQUENCE: 190

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr
            20                  25                  30

<210> SEQ ID NO 191
<211> LENGTH: 14
<212> TYPE: PRT
<213> ORGANISM: Artificial Sequence
<220> FEATURE:
<223> OTHER INFORMATION: Synthetic peptide

<400> SEQUENCE: 191

Trp Val Gln Gln Ala Pro Gly Lys Gly Leu Glu Trp Met Gly
1               5                   10

<210> SEQ ID NO 192
<211> LENGTH: 30
<212> TYPE: PRT
<213> ORGANISM: Artificial Sequence
<220> FEATURE:
<223> OTHER INFORMATION: Synthetic peptide

<400> SEQUENCE: 192

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 193
<211> LENGTH: 14
<212> TYPE: PRT
<213> ORGANISM: Artificial Sequence
<220> FEATURE:
<223> OTHER INFORMATION: Synthetic peptide

<400> SEQUENCE: 193

Trp Ile Arg Gln Pro Pro Gly Lys Ala Leu Glu Trp Leu Ala
1               5                   10

<210> SEQ ID NO 194
<211> LENGTH: 30
<212> TYPE: PRT
<213> ORGANISM: Artificial Sequence
<220> FEATURE:
<223> OTHER INFORMATION: Synthetic peptide

<400> SEQUENCE: 194

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser
            20                  25                  30

```
<210> SEQ ID NO 195
<211> LENGTH: 30
<212> TYPE: PRT
<213> ORGANISM: Artificial Sequence
<220> FEATURE:
<223> OTHER INFORMATION: Synthetic peptide

<400> SEQUENCE: 195

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 196
<211> LENGTH: 30
<212> TYPE: PRT
<213> ORGANISM: Artificial Sequence
<220> FEATURE:
<223> OTHER INFORMATION: Synthetic peptide

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 197
<211> LENGTH: 14
<212> TYPE: PRT
<213> ORGANISM: Artificial Sequence
<220> FEATURE:
<223> OTHER INFORMATION: Synthetic peptide

<400> SEQUENCE: 197

Trp Val Arg Gln Ala Pro Gly Lys Gly Leu Glu Trp Val Ala
1               5                   10

<210> SEQ ID NO 198
<211> LENGTH: 30
<212> TYPE: PRT
<213> ORGANISM: Artificial Sequence
<220> FEATURE:
<223> OTHER INFORMATION: Synthetic peptide

<400> SEQUENCE: 198

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp
            20                  25                  30

<210> SEQ ID NO 199
<211> LENGTH: 14
<212> TYPE: PRT
<213> ORGANISM: Artificial Sequence
<220> FEATURE:
<223> OTHER INFORMATION: Synthetic peptide

<400> SEQUENCE: 199

Trp Val Arg Gln Ala Pro Gly Lys Gly Leu Glu Trp Val Ser
1               5                   10

<210> SEQ ID NO 200
<211> LENGTH: 30
<212> TYPE: PRT
<213> ORGANISM: Artificial Sequence
<220> FEATURE:
```

```
<223> OTHER INFORMATION: Synthetic peptide

<400> SEQUENCE: 200

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 201
<211> LENGTH: 14
<212> TYPE: PRT
<213> ORGANISM: Artificial Sequence
<220> FEATURE:
<223> OTHER INFORMATION: Synthetic peptide

<400> SEQUENCE: 201

Trp Ile Arg Gln Ala Pro Gly Lys Gly Leu Glu Trp Val Ser
1               5                   10

<210> SEQ ID NO 202
<211> LENGTH: 14
<212> TYPE: PRT
<213> ORGANISM: Artificial Sequence
<220> FEATURE:
<223> OTHER INFORMATION: Synthetic peptide

<400> SEQUENCE: 202

Trp Val Arg Gln Ala Thr Gly Lys Gly Leu Glu Trp Val Ser
1               5                   10

<210> SEQ ID NO 203
<211> LENGTH: 30
<212> TYPE: PRT
<213> ORGANISM: Artificial Sequence
<220> FEATURE:
<223> OTHER INFORMATION: Synthetic peptide

<400> SEQUENCE: 203

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 204
<211> LENGTH: 14
<212> TYPE: PRT
<213> ORGANISM: Artificial Sequence
<220> FEATURE:
<223> OTHER INFORMATION: Synthetic peptide

<400> SEQUENCE: 204

Trp Val Arg Gln Ala Pro Gly Lys Gly Leu Glu Trp Val Gly
1               5                   10

<210> SEQ ID NO 205
<211> LENGTH: 30
<212> TYPE: PRT
<213> ORGANISM: Artificial Sequence
<220> FEATURE:
<223> OTHER INFORMATION: Synthetic peptide

<400> SEQUENCE: 205

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp
            20                  25                  30
```

```
<210> SEQ ID NO 206
<211> LENGTH: 30
<212> TYPE: PRT
<213> ORGANISM: Artificial Sequence
<220> FEATURE:
<223> OTHER INFORMATION: Synthetic peptide

<400> SEQUENCE: 206

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 207
<211> LENGTH: 30
<212> TYPE: PRT
<213> ORGANISM: Artificial Sequence
<220> FEATURE:
<223> OTHER INFORMATION: Synthetic peptide

<400> SEQUENCE: 207

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 208
<211> LENGTH: 30
<212> TYPE: PRT
<213> ORGANISM: Artificial Sequence
<220> FEATURE:
<223> OTHER INFORMATION: Synthetic peptide

<400> SEQUENCE: 208

Glu Val Gln Leu Val Glu Ser Gly Gly Val Val Val Gln Pro Gly Gly
1               5                   10                  15

Ser Leu Arg Leu Ser Cys Ala Ala Ser Gly Phe Thr Phe Asp
            20                  25                  30

<210> SEQ ID NO 209
<211> LENGTH: 30
<212> TYPE: PRT
<213> ORGANISM: Artificial Sequence
<220> FEATURE:
<223> OTHER INFORMATION: Synthetic peptide

<400> SEQUENCE: 209

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly
            20                  25                  30

<210> SEQ ID NO 210
<211> LENGTH: 14
<212> TYPE: PRT
<213> ORGANISM: Artificial Sequence
<220> FEATURE:
<223> OTHER INFORMATION: Synthetic peptide

<400> SEQUENCE: 210

Trp Phe Arg Gln Ala Pro Gly Lys Gly Leu Glu Trp Val Gly
1               5                   10

<210> SEQ ID NO 211
```

-continued

```
<211> LENGTH: 30
<212> TYPE: PRT
<213> ORGANISM: Artificial Sequence
<220> FEATURE:
<223> OTHER INFORMATION: Synthetic peptide

<400> SEQUENCE: 211

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser
            20                  25                  30

<210> SEQ ID NO 212
<211> LENGTH: 14
<212> TYPE: PRT
<213> ORGANISM: Artificial Sequence
<220> FEATURE:
<223> OTHER INFORMATION: Synthetic peptide

<400> SEQUENCE: 212

Trp Val Arg Gln Ala Pro Gly Lys Gly Leu Glu Tyr Val Ser
1               5                   10

<210> SEQ ID NO 213
<211> LENGTH: 30
<212> TYPE: PRT
<213> ORGANISM: Artificial Sequence
<220> FEATURE:
<223> OTHER INFORMATION: Synthetic peptide

<400> SEQUENCE: 213

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser
            20                  25                  30

<210> SEQ ID NO 214
<211> LENGTH: 30
<212> TYPE: PRT
<213> ORGANISM: Artificial Sequence
<220> FEATURE:
<223> OTHER INFORMATION: Synthetic peptide

<400> SEQUENCE: 214

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser
            20                  25                  30

<210> SEQ ID NO 215
<211> LENGTH: 14
<212> TYPE: PRT
<213> ORGANISM: Artificial Sequence
<220> FEATURE:
<223> OTHER INFORMATION: Synthetic peptide

<400> SEQUENCE: 215

Trp Val Arg Gln Ala Ser Gly Lys Gly Leu Glu Trp Val Gly
1               5                   10

<210> SEQ ID NO 216
<211> LENGTH: 14
<212> TYPE: PRT
<213> ORGANISM: Artificial Sequence
<220> FEATURE:
<223> OTHER INFORMATION: Synthetic peptide
```

```
-continued

<400> SEQUENCE: 216

Trp Val Arg Gln Ala Pro Gly Lys Gly Leu Val Trp Val Ser
1               5                   10

<210> SEQ ID NO 217
<211> LENGTH: 30
<212> TYPE: PRT
<213> ORGANISM: Artificial Sequence
<220> FEATURE:
<223> OTHER INFORMATION: Synthetic peptide

<400> SEQUENCE: 217

Glu Val Gln Leu Val Glu Ser Arg Gly Val Leu Val Gln Pro Gly Gly
1               5                   10                  15

Ser Leu Arg Leu Ser Cys Ala Ala Ser Gly Phe Thr Val Ser
            20                  25                  30

<210> SEQ ID NO 218
<211> LENGTH: 30
<212> TYPE: PRT
<213> ORGANISM: Artificial Sequence
<220> FEATURE:
<223> OTHER INFORMATION: Synthetic peptide

<400> SEQUENCE: 218

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser
            20                  25                  30

<210> SEQ ID NO 219
<211> LENGTH: 14
<212> TYPE: PRT
<213> ORGANISM: Artificial Sequence
<220> FEATURE:
<223> OTHER INFORMATION: Synthetic peptide

<400> SEQUENCE: 219

Trp Val Arg Gln Pro Pro Gly Lys Gly Leu Glu Trp Ile Gly
1               5                   10

<210> SEQ ID NO 220
<211> LENGTH: 30
<212> TYPE: PRT
<213> ORGANISM: Artificial Sequence
<220> FEATURE:
<223> OTHER INFORMATION: Synthetic peptide

<400> SEQUENCE: 220

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser
            20                  25                  30

<210> SEQ ID NO 221
<211> LENGTH: 14
<212> TYPE: PRT
<213> ORGANISM: Artificial Sequence
<220> FEATURE:
<223> OTHER INFORMATION: Synthetic peptide

<400> SEQUENCE: 221

Trp Ile Arg Gln Pro Pro Gly Lys Gly Leu Glu Trp Ile Gly
1               5                   10
```

```
<210> SEQ ID NO 222
<211> LENGTH: 30
<212> TYPE: PRT
<213> ORGANISM: Artificial Sequence
<220> FEATURE:
<223> OTHER INFORMATION: Synthetic peptide

<400> SEQUENCE: 222

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser
            20                  25                  30

<210> SEQ ID NO 223
<211> LENGTH: 14
<212> TYPE: PRT
<213> ORGANISM: Artificial Sequence
<220> FEATURE:
<223> OTHER INFORMATION: Synthetic peptide

<400> SEQUENCE: 223

Trp Ile Arg Gln His Pro Gly Lys Gly Leu Glu Trp Ile Gly
1               5                   10

<210> SEQ ID NO 224
<211> LENGTH: 30
<212> TYPE: PRT
<213> ORGANISM: Artificial Sequence
<220> FEATURE:
<223> OTHER INFORMATION: Synthetic peptide

<400> SEQUENCE: 224

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser
            20                  25                  30

<210> SEQ ID NO 225
<211> LENGTH: 30
<212> TYPE: PRT
<213> ORGANISM: Artificial Sequence
<220> FEATURE:
<223> OTHER INFORMATION: Synthetic peptide

<400> SEQUENCE: 225

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser
            20                  25                  30

<210> SEQ ID NO 226
<211> LENGTH: 30
<212> TYPE: PRT
<213> ORGANISM: Artificial Sequence
<220> FEATURE:
<223> OTHER INFORMATION: Synthetic peptide

<400> SEQUENCE: 226

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 227
<211> LENGTH: 30
<212> TYPE: PRT
```

<213> ORGANISM: Artificial Sequence
<220> FEATURE:
<223> OTHER INFORMATION: Synthetic peptide

<400> SEQUENCE: 227

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 228
<211> LENGTH: 30
<212> TYPE: PRT
<213> ORGANISM: Artificial Sequence
<220> FEATURE:
<223> OTHER INFORMATION: Synthetic peptide

<400> SEQUENCE: 228

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Tyr Ser
            20                  25                  30

<210> SEQ ID NO 229
<211> LENGTH: 30
<212> TYPE: PRT
<213> ORGANISM: Artificial Sequence
<220> FEATURE:
<223> OTHER INFORMATION: Synthetic peptide

<400> SEQUENCE: 229

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser
            20                  25                  30

<210> SEQ ID NO 230
<211> LENGTH: 30
<212> TYPE: PRT
<213> ORGANISM: Artificial Sequence
<220> FEATURE:
<223> OTHER INFORMATION: Synthetic peptide

<400> SEQUENCE: 230

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30

<210> SEQ ID NO 231
<211> LENGTH: 14
<212> TYPE: PRT
<213> ORGANISM: Artificial Sequence
<220> FEATURE:
<223> OTHER INFORMATION: Synthetic peptide

<400> SEQUENCE: 231

Trp Val Arg Gln Met Pro Gly Lys Gly Leu Glu Trp Met Gly
1               5                   10

<210> SEQ ID NO 232
<211> LENGTH: 30
<212> TYPE: PRT
<213> ORGANISM: Artificial Sequence
<220> FEATURE:
<223> OTHER INFORMATION: Synthetic peptide

<400> SEQUENCE: 232

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr
            20                  25                  30

<210> SEQ ID NO 233
<211> LENGTH: 30
<212> TYPE: PRT
<213> ORGANISM: Artificial Sequence
<220> FEATURE:
<223> OTHER INFORMATION: Synthetic peptide

<400> SEQUENCE: 233

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser
            20                  25                  30

<210> SEQ ID NO 234
<211> LENGTH: 14
<212> TYPE: PRT
<213> ORGANISM: Artificial Sequence
<220> FEATURE:
<223> OTHER INFORMATION: Synthetic peptide

<400> SEQUENCE: 234

Trp Ile Arg Gln Ser Pro Ser Arg Gly Leu Glu Trp Leu Gly
1               5                   10

<210> SEQ ID NO 235
<211> LENGTH: 30
<212> TYPE: PRT
<213> ORGANISM: Artificial Sequence
<220> FEATURE:
<223> OTHER INFORMATION: Synthetic peptide

<400> SEQUENCE: 235

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 236

<400> SEQUENCE: 236

000

<210> SEQ ID NO 237
<211> LENGTH: 32
<212> TYPE: PRT
<213> ORGANISM: Artificial Sequence
<220> FEATURE:
<223> OTHER INFORMATION: Synthetic peptide

<400> SEQUENCE: 237

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 238
<211> LENGTH: 32

```
<212> TYPE: PRT
<213> ORGANISM: Artificial Sequence
<220> FEATURE:
<223> OTHER INFORMATION: Synthetic peptide

<400> SEQUENCE: 238

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 239
<211> LENGTH: 32
<212> TYPE: PRT
<213> ORGANISM: Artificial Sequence
<220> FEATURE:
<223> OTHER INFORMATION: Synthetic peptide

<400> SEQUENCE: 239

Arg Val Thr Met Thr Arg Asn Thr Ser Ile Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 240
<211> LENGTH: 32
<212> TYPE: PRT
<213> ORGANISM: Artificial Sequence
<220> FEATURE:
<223> OTHER INFORMATION: Synthetic peptide

<400> SEQUENCE: 240

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 241
<211> LENGTH: 32
<212> TYPE: PRT
<213> ORGANISM: Artificial Sequence
<220> FEATURE:
<223> OTHER INFORMATION: Synthetic peptide

<400> SEQUENCE: 241

Arg Val Thr Met Thr Glu Asp Thr Ser Thr Asp Thr Ala Tyr Met Glu
1               5                   10                  15

Leu Ser Ser Leu Arg Ser Glu Asp Thr Ala Val Tyr Tyr Cys Ala Thr
            20                  25                  30

<210> SEQ ID NO 242
<211> LENGTH: 32
<212> TYPE: PRT
<213> ORGANISM: Artificial Sequence
<220> FEATURE:
<223> OTHER INFORMATION: Synthetic peptide

<400> SEQUENCE: 242

Arg Val Thr Ile Thr Arg Asp Arg Ser Met Ser Thr Ala Tyr Met Glu
1               5                   10                  15

Leu Ser Ser Leu Arg Ser Glu Asp Thr Ala Met Tyr Tyr Cys Ala Arg
            20                  25                  30

<210> SEQ ID NO 243
<211> LENGTH: 32
```

<212> TYPE: PRT
<213> ORGANISM: Artificial Sequence
<220> FEATURE:
<223> OTHER INFORMATION: Synthetic peptide

<400> SEQUENCE: 243

Arg Val Thr Met Thr Arg Asp Thr Ser Thr Ser Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 244
<211> LENGTH: 32
<212> TYPE: PRT
<213> ORGANISM: Artificial Sequence
<220> FEATURE:
<223> OTHER INFORMATION: Synthetic peptide

<400> SEQUENCE: 244

Arg Val Thr Ile Thr Arg Asp Met Ser Thr Ser Thr Ala Tyr Met Glu
1               5                   10                  15

Leu Ser Ser Leu Arg Ser Glu Asp Thr Ala Val Tyr Tyr Cys Ala Ala
            20                  25                  30

<210> SEQ ID NO 245
<211> LENGTH: 32
<212> TYPE: PRT
<213> ORGANISM: Artificial Sequence
<220> FEATURE:
<223> OTHER INFORMATION: Synthetic peptide

<400> SEQUENCE: 245

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 246
<211> LENGTH: 32
<212> TYPE: PRT
<213> ORGANISM: Artificial Sequence
<220> FEATURE:
<223> OTHER INFORMATION: Synthetic peptide

<400> SEQUENCE: 246

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 247
<211> LENGTH: 32
<212> TYPE: PRT
<213> ORGANISM: Artificial Sequence
<220> FEATURE:
<223> OTHER INFORMATION: Synthetic peptide

<400> SEQUENCE: 247

Arg Val Thr Ile Thr Ala Asp Thr Ser Thr Ser Asp Thr Ala Tyr Met Glu
1               5                   10                  15

Leu Ser Ser Leu Arg Ser Glu Asp Thr Ala Val Tyr Tyr Cys Ala Thr
            20                  25                  30

<210> SEQ ID NO 248
<211> LENGTH: 33

```
<212> TYPE: PRT
<213> ORGANISM: Artificial Sequence
<220> FEATURE:
<223> OTHER INFORMATION: Synthetic peptide

<400> SEQUENCE: 248

Arg Leu Thr Ile Thr Lys Asp Thr Ser Lys Asn Gln Val Val Leu Thr
1               5                   10                  15

Met Thr Asn Met Asp Pro Val Asp Thr Ala Thr Tyr Tyr Cys Ala His
            20                  25                  30

Arg

<210> SEQ ID NO 249
<211> LENGTH: 33
<212> TYPE: PRT
<213> ORGANISM: Artificial Sequence
<220> FEATURE:
<223> OTHER INFORMATION: Synthetic peptide

<400> SEQUENCE: 249

Arg Leu Thr Ile Ser Lys Asp Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

Ile

<210> SEQ ID NO 250
<211> LENGTH: 33
<212> TYPE: PRT
<213> ORGANISM: Artificial Sequence
<220> FEATURE:
<223> OTHER INFORMATION: Synthetic peptide

<400> SEQUENCE: 250

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

Ile

<210> SEQ ID NO 251
<211> LENGTH: 32
<212> TYPE: PRT
<213> ORGANISM: Artificial Sequence
<220> FEATURE:
<223> OTHER INFORMATION: Synthetic peptide

<400> SEQUENCE: 251

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 252
<211> LENGTH: 33
<212> TYPE: PRT
<213> ORGANISM: Artificial Sequence
<220> FEATURE:
<223> OTHER INFORMATION: Synthetic peptide

<400> SEQUENCE: 252

Arg Phe Thr Ile Ser Arg Asp Asn Ala Lys Asn Ser Leu Tyr Leu Gln
1               5                   10                  15
```

```
Met Asn Ser Leu Arg Ala Glu Asp Thr Ala Leu Tyr Tyr Cys Ala Lys
            20                  25                  30
Asp
```

<210> SEQ ID NO 253
<211> LENGTH: 32
<212> TYPE: PRT
<213> ORGANISM: Artificial Sequence
<220> FEATURE:
<223> OTHER INFORMATION: Synthetic peptide

<400> SEQUENCE: 253

```
Arg Phe Thr Ile Ser Arg Asp Asp Ser Lys Asn Thr Leu Tyr Leu Gln
1               5                   10                  15

Met Asn Ser Leu Lys Thr Glu Asp Thr Ala Val Tyr Tyr Cys Thr Thr
            20                  25                  30
```

<210> SEQ ID NO 254
<211> LENGTH: 32
<212> TYPE: PRT
<213> ORGANISM: Artificial Sequence
<220> FEATURE:
<223> OTHER INFORMATION: Synthetic peptide

<400> SEQUENCE: 254

```
Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Leu Tyr His Cys Ala Arg
            20                  25                  30
```

<210> SEQ ID NO 255
<211> LENGTH: 32
<212> TYPE: PRT
<213> ORGANISM: Artificial Sequence
<220> FEATURE:
<223> OTHER INFORMATION: Synthetic peptide

<400> SEQUENCE: 255

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30
```

<210> SEQ ID NO 256
<211> LENGTH: 32
<212> TYPE: PRT
<213> ORGANISM: Artificial Sequence
<220> FEATURE:
<223> OTHER INFORMATION: Synthetic peptide

<400> SEQUENCE: 256

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30
```

<210> SEQ ID NO 257
<211> LENGTH: 33
<212> TYPE: PRT
<213> ORGANISM: Artificial Sequence
<220> FEATURE:
<223> OTHER INFORMATION: Synthetic peptide

<400> SEQUENCE: 257

```
Arg Phe Thr Ile Ser Arg Asp Asn Ser Lys Asn Ser Leu Tyr Leu Gln
```

Met Asn Ser Leu Arg Thr Glu Asp Thr Ala Leu Tyr Tyr Cys Ala Lys
            20                  25                  30

Asp

<210> SEQ ID NO 258
<211> LENGTH: 32
<212> TYPE: PRT
<213> ORGANISM: Artificial Sequence
<220> FEATURE:
<223> OTHER INFORMATION: Synthetic peptide

<400> SEQUENCE: 258

Arg Phe Thr Ile Ser Arg Asp Asn Ala Lys Asn Ser Leu Tyr Leu Gln
1               5                   10                  15

Met Asn Ser Leu Arg Gln Glu Asp Thr Ala Val Tyr Tyr Cys Ala Arg
            20                  25                  30

<210> SEQ ID NO 259
<211> LENGTH: 32
<212> TYPE: PRT
<213> ORGANISM: Artificial Sequence
<220> FEATURE:
<223> OTHER INFORMATION: Synthetic peptide

<400> SEQUENCE: 259

Arg Phe Thr Ile Ser Arg Asp Gly Ser Lys Ser Ile Ala Tyr Leu Gln
1               5                   10                  15

Met Asn Ser Leu Lys Thr Glu Asp Thr Ala Val Tyr Tyr Cys Thr Arg
            20                  25                  30

<210> SEQ ID NO 260
<211> LENGTH: 32
<212> TYPE: PRT
<213> ORGANISM: Artificial Sequence
<220> FEATURE:
<223> OTHER INFORMATION: Synthetic peptide

<400> SEQUENCE: 260

Arg Phe Thr Ile Ser Arg Asp Asn Ser Lys Asn Thr Leu Tyr Leu Gln
1               5                   10                  15

Met Gly Ser Leu Arg Ala Glu Asp Met Ala Val Tyr Tyr Cys Ala Arg
            20                  25                  30

<210> SEQ ID NO 261
<211> LENGTH: 32
<212> TYPE: PRT
<213> ORGANISM: Artificial Sequence
<220> FEATURE:
<223> OTHER INFORMATION: Synthetic peptide

<400> SEQUENCE: 261

Arg Phe Thr Ile Ser Arg Asp Asp Ser Lys Asn Ser Leu Tyr Leu Gln
1               5                   10                  15

Met Asn Ser Leu Lys Thr Glu Asp Thr Ala Val Tyr Tyr Cys Ala Arg
            20                  25                  30

<210> SEQ ID NO 262
<211> LENGTH: 32
<212> TYPE: PRT
<213> ORGANISM: Artificial Sequence
<220> FEATURE:
<223> OTHER INFORMATION: Synthetic peptide

<400> SEQUENCE: 262

Arg Phe Thr Ile Ser Arg Asp Asp Ser Lys Asn Thr Ala Tyr Leu Gln
1               5                   10                  15

Met Asn Ser Leu Lys Thr Glu Asp Thr Ala Val Tyr Tyr Cys Thr Arg
            20                  25                  30

<210> SEQ ID NO 263
<211> LENGTH: 32
<212> TYPE: PRT
<213> ORGANISM: Artificial Sequence
<220> FEATURE:
<223> OTHER INFORMATION: Synthetic peptide

<400> SEQUENCE: 263

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 264
<211> LENGTH: 32
<212> TYPE: PRT
<213> ORGANISM: Artificial Sequence
<220> FEATURE:
<223> OTHER INFORMATION: Synthetic peptide

<400> SEQUENCE: 264

Arg Phe Thr Ile Ser Arg Asp Asn Ser Lys Asn Thr Leu His Leu Gln
1               5                   10                  15

Met Asn Ser Leu Arg Ala Glu Asp Thr Ala Val Tyr Tyr Cys Lys Lys
            20                  25                  30

<210> SEQ ID NO 265
<211> LENGTH: 32
<212> TYPE: PRT
<213> ORGANISM: Artificial Sequence
<220> FEATURE:
<223> OTHER INFORMATION: Synthetic peptide

<400> SEQUENCE: 265

Arg Val Thr Ile Ser Val Asp Lys Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 266
<211> LENGTH: 32
<212> TYPE: PRT
<213> ORGANISM: Artificial Sequence
<220> FEATURE:
<223> OTHER INFORMATION: Synthetic peptide

<400> SEQUENCE: 266

Arg Val Thr Met Ser Val Asp Thr Ser Lys Asn Gln Phe Ser Leu Lys
1               5                   10                  15

Leu Ser Ser Val Thr Ala Val Asp Thr Ala Val Tyr Tyr Cys Ala Arg
            20                  25                  30

<210> SEQ ID NO 267
<211> LENGTH: 32
<212> TYPE: PRT
<213> ORGANISM: Artificial Sequence
<220> FEATURE:
<223> OTHER INFORMATION: Synthetic peptide

<400> SEQUENCE: 267

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 268
<211> LENGTH: 32
<212> TYPE: PRT
<213> ORGANISM: Artificial Sequence
<220> FEATURE:
<223> OTHER INFORMATION: Synthetic peptide

<400> SEQUENCE: 268

Arg Val Thr Ile Ser Val Asp Arg Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 269
<211> LENGTH: 32
<212> TYPE: PRT
<213> ORGANISM: Artificial Sequence
<220> FEATURE:
<223> OTHER INFORMATION: Synthetic peptide

<400> SEQUENCE: 269

Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30

<210> SEQ ID NO 270
<211> LENGTH: 32
<212> TYPE: PRT
<213> ORGANISM: Artificial Sequence
<220> FEATURE:
<223> OTHER INFORMATION: Synthetic peptide

<400> SEQUENCE: 270

His Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30

<210> SEQ ID NO 271
<211> LENGTH: 32
<212> TYPE: PRT
<213> ORGANISM: Artificial Sequence
<220> FEATURE:
<223> OTHER INFORMATION: Synthetic peptide

<400> SEQUENCE: 271

Arg Ile Thr Ile Asn Pro Asp Thr Ser Lys Asn Gln Phe Ser Leu Gln
1               5                   10                  15

Leu Asn Ser Val Thr Pro Glu Asp Thr Ala Val Tyr Tyr Cys Ala Arg
            20                  25                  30

<210> SEQ ID NO 272
<211> LENGTH: 32
<212> TYPE: PRT
<213> ORGANISM: Artificial Sequence
<220> FEATURE:
<223> OTHER INFORMATION: Synthetic peptide

<400> SEQUENCE: 272
```

-continued

```
Arg Phe Val Phe Ser Leu Asp Thr Ser Val Ser Thr Ala Tyr Leu Gln
1               5                   10                  15

Ile Cys Ser Leu Lys Ala Glu Asp Thr Ala Val Tyr Tyr Cys Ala Arg
            20                  25                  30
```

US 7,964,707 B2

ANTI-IL2 ANTIBODIES

This application is a national phase application under 35 U.S.C. §371 of International Application No. PCT/EP2006/005194 filed May 31, 2006, which claims priority to European Patent Application No. 05011845.4 filed Jun. 1, 2005. The entire text of each of the above-referenced disclosures is specifically incorporated herein by reference without disclaimer.

The invention relates to antibodies and fragments thereof which specifically bind the human cytokine IL2. The invention further relates to polynucleotides encoding, pharmaceutical compositions comprising and medical uses involving such antibodies and fragments thereof.

Human IL2 is a protein of 133 amino acids (15.4 kDa) which does not bear significant sequence homology to any other factors. IL2 is synthesized as a precursor protein of 153 amino acids with the first 20 amino-terminal amino acids functioning as a hydrophobic secretory signal sequence. The protein contains a single disulfide bond (joining positions Cys58/105) essential for biological activity.

The biological activities of IL2 are mediated by a membrane receptor that is expressed almost exclusively on activated, but not on resting, T-cells. The complete IL2 receptor consists of three type I trans-membrane protein subunits: alpha, beta and gamma; a lower affinity functional receptor can be constituted by the beta and gamma receptor proteins only. Resting B-cells and resting mononuclear leukocytes rarely express this receptor. The expression of the IL2 receptor, in particular of the alpha subunit, is modulated by multiple factors, for example IL5, IL6 and L2R/p55 inducing factor.

Mouse and human IL2 both cause proliferation of T-cells of the homologous species at high efficiency. Human IL2 is functional also on mouse cells, but not vice versa. IL2 is a growth factor for all subpopulations of T-lymphocytes. It is an antigen-unspecific proliferation factor for T-cells that induces cell cycle progression in resting cells and thus allows clonal expansion of activated T-lymphocytes. IL2 also promotes the proliferation and differentiation of activated B-cells. As with the proliferation of T-cells, this activity also requires the presence of additional factors, for example IL4.

Due to its effects on T-cells and B-cells IL2 is a central regulator of immune responses. The central importance of IL2 in the initiation and amplification of the adaptive immune responses is well illustrated by the clinical efficacy of drugs that are most commonly used to suppress undesirable immune responses such as transplant rejection. The immunosuppressive drugs cyclosporin A and FK506 (tacrolimus) inhibit IL2 production by disrupting signaling through the T-cell receptor, whereas rapamycin (sirolimus) inhibits signaling through the IL2 receptor. Cyclosporin A and rapamycin act synergistically to limit immune responses by preventing the IL2-driven clonal expansion of T cells. However, all these compounds target intracellular signaling pathways which do not exclusively interfere with IL2 but also with other factors. This implies that clinical application of these drugs imposes a considerable risk of undesirable side effects due to their limited target specificity.

Multiple examples of antibody inhibitors of IL2 activity are also known in the art, for example the commercial antibody daclizumab (Zenapax®, Protein Design Lab, Inc.). However, known antibody inhibitors of IL2 activity exert their biological effect by binding to the IL2 receptor rather than to the antigen itself. Given the important clinical applications of inhibitors of IL2 activity, it is an aim of the present invention to provide alternative specific inhibitors of IL2 activity.

Accordingly, one aspect of the invention provides a humanized monoclonal antibody or fragment thereof which specifically binds to human interleukin-2 (IL2), wherein said humanized monoclonal antibody neutralizes the activity of human IL2 by binding to said human IL2 prior to, during, and/or subsequent to the binding of said human IL2 to the human IL2-receptor, and wherein the light chain variable region of said humanized monoclonal antibody comprises in its second framework region the contiguous amino acid sequence KAPKA (SEQ ID NO:13), preferably at amino acid positions 42-46.

As used herein, the terms "humanized monoclonal antibody," or "humanized antibody," or "humanized immunoglobulin," or grammatically related variants thereof are used interchangeably to refer to a molecule comprising an antigen binding site derived from one or more non-human immunoglobulins, said molecule additionally comprising at least a portion, e.g. at least one of the framework regions of the light or heavy chain variable domain derived from one or more human immunoglobulins or germline sequences thereof. A "humanized antibody" as used herein includes a humanized light chain variable domain immunoglobulin and a humanized heavy chain variable domain immunoglobulin. The humanized antibody may include a constant region partially or wholly derived from (including synthetic analogs) one or more human gene sequence. A humanized antibody is expected to bind to the same target antigen as a donor antibody which supplied the CDRs. Typically, all segments or portions of the humanized antibody or immunoglobulin, with the exception of the CDRs, are substantially identical or substantially homologous to corresponding segments or portions of naturally occurring or consensus human immunoglobulin sequences.

The light chain variable region (VL) of said humanized monoclonal antibody comprises in its second framework region the contiguous amino acid sequence KAPKA, preferable at amino acid positions 42-46. This preferred sequence numbering, i.e., positions 42-46, refers to the numbering set out in the "VBase" database (© MRC Centre for Protein Engineering) available under in the internet address worldwide-web at mrc-cpe.cam.ac.uk. For clarity, sequence alignments of framework regions of human germline VL (as V-kappa and V-lambda sequences) and VH regions are included in the present application as there appear in Vbase (see FIGS. 7, 8 and 9, respectively; in particular FIGS. 8a and 9a for the numbering of the second light chain framework regions in human germline V-kappa and V-lambda sequences).

While the preferred numbering (i.e. amino acid positions 42-46) of the amino acid sequence KAPKA (i.e. Lys-Ala-Pro-Lys-Ala) is provided here for ease of correlation with the reference cited above, it should be understood that the identities of the amino acids within this partial sequence rather than the sequence numbering in and of itself is determinative for the activity of the humanized monoclonal antibody of the invention. As one of skill in the art knows, there exist multiple conventions for numbering human germline antibody sequences, the above cited reference (VBase) being only one of these. Therefore, the partial amino acid sequence KAPKA comprised within the second framework region of certain human germline light chain variable regions may be assigned another numbering according to a numbering convention other than that specified in the above citation. In such a case, the partial amino acid sequence KAPKA would bear a numbering other than preferred amino acid positions 42-46, while the sequence corresponding to the preferred amino acid positions 42-46 under this other numbering convention would likely be an amino acid sequence other than KAPKA. In such a case, as one of skill in the art will understand, the partial amino acid sequence with the "correct" sequence (KAPKA) but deviant numbering (something other than the preferred amino acid positions 42-46) should be regarded as an essential feature of the invention rather than another partial amino acid sequence, the numbering of which is "correct" (preferred amino acid positions 42-46), but the identity of which is not KAPKA.

It has been surprisingly observed that antibodies or fragments thereof lacking the consensus sequence KAPKA in the second light chain framework region, in particular lacking the terminal alanine residue in this stretch, are capable of specifically binding IL2, but not capable of neutralizing its activity. This is especially the case when the CDR regions comprised in the light and heavy variable chains of the humanized monoclonal antibody are as set out in SEQ ID Nos. 1-3 (for light chain variable region CDRs 1-3, respectively), and SEQ ID Nos. 4-6 (for heavy chain variable region CDRs 1-3, respectively). Without being bound by theory, the inventors attribute this loss of neutralizing activity upon omission of the consensus sequence KAPKA, in particular upon substitution of the terminal alanine residue in this stretch with another amino acid other than alanine, to a destabilization and/or to conformational rearrangements having an adverse effect upon neutralization, but not on binding activity.

The term "specifically binds" or grammatically related expressions such as "specific binding", "binding specifically", "specific binder" etc. as used herein refer to the ability of the humanized monoclonal antibody or fragment thereof to discriminate between human IL2 and any number of other potential antigens different from human IL2 to such an extent that, from a pool of a plurality of different antigens as potential binding partners, only human IL2 is bound, or is significantly bound. Within the meaning of the invention, human IL2 is "significantly" bound when, from among a pool of a plurality of equally accessible different antigens as potential binding partners, human IL2 is bound at least 10-fold, preferably 50-fold, most preferably 100-fold or greater more frequently (in a kinetic sense) than other antigens different than human IL2. As one of ordinary skill in the art understands, such kinetic measurements can be performed i.a. on a Biacore apparatus.

The humanized antibody or fragment thereof according to the invention is monoclonal. As used herein, the term "monoclonal" is to be understood as having the meaning typically ascribed to it in the art, namely an antibody which recognizes a single epitope on the antigen bound. This is in contrast to polyclonal antibody, which represents a collection of distinct antibodies binding to the same antigen, albeit at different epitopes on this antigen. For this reason a single molecule of antigen may simultaneously be bound by multiple molecules of polyclonal antibody specific for this antigen, but only by a single molecule of a particular monoclonal antibody specific for this antigen; following binding by a single molecule of monoclonal antibody, the bound epitope is blocked and therefore no longer available for binding by another molecule of identical monoclonal antibody. The monoclonal nature of the antibody makes it particularly well suited for use as a therapeutic agent, since such antibody will exist as a single, homogeneous molecular species which can be well-characterized and reproducibly made and purified. These factors result in a product whose biological activity can be predicted with a high level of precision, a very important consideration if such a molecule is going to gain regulatory approval for therapeutic administration in mammals, in particular humans.

As used herein, "neutralization," "neutralizer," "neutralizing" and grammatically related variants thereof refers to partial or complete attenuation of the biological effect(s) of IL2. Such partial or complete attenuation of the biological effect(s) of IL2 results from modification, interruption and/or abrogation of IL2-mediated signal transduction, as manifested, for example, in intracellular signalling, cellular proliferation, release of soluble substances, up- or down-regulation of intracellular gene activation, for example that resulting in expression of surface receptors for ligands other than IL2. As one of skill in the art understands, there exist multiple modes of determining whether an agent, for example an antibody in question or fragment thereof is to be classified as a neutralizer. Generally, this may be accomplished by a standard in vitro test performed generally as follows: In a first proliferation experiment, a cell line, the degree of proliferation of which is known to depend on the activity of IL2, is incubated in a series of samples with varying concentrations of IL2, following which incubation the degree of proliferation of the cell line is measured. From this measurement, the concentration of IL2 which allowed half-maximal proliferation of the cells is determined. A second proliferation experiment is then performed employing in each of a series of samples the same number of cells as used in the first proliferation experiment, the above-determined concentration of IL2 and, this time, varying concentrations of an antibody or fragment thereof suspected of being a neutralizer of IL2. Cell proliferation is again measured to determine the concentration of antibody or fragment thereof sufficient to effect half-maximal growth inhibition. If the resulting graph of growth inhibition vs. antibody (or fragment thereof) concentration is sigmoidal in shape, then some degree of antibody-dependent growth inhibition has been effected, i.e. the activity of IL2 has been neutralized to some extent. In such a case, the antibody or fragment thereof is to be considered a "neutralizer" in the sense of the present invention. One example of a cell line, the degree of proliferation of which is known to depend on the activity of IL2, is the CTLL-2 cell line, commercially available from LGC Promochem. Another example of a suitable cell line is NK92 (DSMZ).

Surprisingly, the humanized monoclonal antibody of the invention neutralizes the activity of human IL2 by binding to said human IL2 prior to, during, and/or subsequent to the binding of said human IL2 to the human IL2-receptor. This mode of neutralization is highly unexpected. Conventionally, antibody-mediated neutralization of the biological activity of a ligand, said biological activity depending on binding of said ligand to a receptor, is effected by preventing such a ligand-receptor complex from forming. According to this classical scenario for neutralization, a neutralizing antibody binds ligand or receptor at a location in the ligand-receptor interface. In this way, the presence of the antibody sterically and/or electrostatically prevents formation of the ligand-receptor complex: the ligand-receptor complex is not formed, and the biological activity normally attributed to binding by ligand to its receptor is not effected.

The mode of neutralization observed for a humanized monoclonal antibody according to the invention differs sharply from this classical scenario in that abrogation of biological activity normally attributable to IL2 does not depend on preventing complex formation between IL2 and its receptor. This means that the biological activity of IL2 is abrogated regardless of whether or not IL2 has already bound to the IL2 receptor, implying that the epitope recognized by a humanized monoclonal antibody of the invention is not located on the portion of IL2 which interacts with the IL2 receptor. As such, IL2 neutralization may be achieved with a humanized monoclonal antibody of the invention via several modes.

According to a first mode, the antibody binds to IL2 in solution prior to formation of the complex between IL2 and its receptor so that IL2-mediated signal transduction does not take place in the event that IL2 binds to its receptor.

According to a second mode, the antibody binds to IL2 at the same time as IL2 forms a complex with its receptor. Here again, simultaneous formation of a receptor-IL2-antibody ternary complex does not result in any, or at least any significant signal transduction.

According to a third mode, IL2 has already formed a complex with its receptor, and the antibody binds to IL2 while IL2 exists in complex with its receptor on the surface of an IL2 receptor-bearing cell. In this third scenario, any IL2-mediated signal transduction already taking place prior to binding of IL2 by antibody is abrogated once the antibody is bound.

Such non-classical neutralization, i.e. neutralization as effected by a humanized monoclonal antibody of the invention, is quite surprising, and has several therapeutic advantages.

First, since a humanized monoclonal antibody of the invention recognizes an epitope of IL2 which does not directly participate in contact with the IL2 receptor, no competition arises between the therapeutic antibody on the one hand and the IL2 receptor on the other. This has the effect that lower concentrations of therapeutic antibody may be administered to a patient than would otherwise be possible if a binding competition for the same epitope were to exist between antibody and IL2 receptor. This effectively increases the therapeutic efficacy of a humanized monoclonal antibody of the invention, since the administered concentration may be reduced (relative to that needed given a classical mode of neutralization) with no loss of biological effect.

Administration of a lower amount of therapeutic agent is highly desirable not only from the standpoint of patient tolerability, but also from an economic standpoint, as the cost burden of a given therapy is reduced or, conversely, a larger number of patients may benefit from a given amount of therapeutic antibody.

Second, as alluded to above, the ability of a humanized monoclonal antibody of the invention to bind to and neutralize the biological activity of IL2 already in complex with its receptor has the great advantage that an already-running IL2-mediated signal transduction may be shut off without IL2 first having to dissociate from its receptor binding partner. This has the ultimate effect that the desired neutralizing biological activity of a humanized monoclonal antibody of the invention is realized more quickly in vivo than possible for other "classical" antibody neutralizers which first must compete with the IL2 receptor for the binding epitope on IL2 before eliciting any therapeutic effect. This speed of action may be especially advantageous in acute scenarios such as immune rejection of organ transplants, a known field of anti-IL2 therapy.

A third advantage of such an atypical mode of neutralization as described above relates to the fact that IL2 receptors are located on the surface of T cells. T cells themselves produce IL2 and also respond to IL2 by proliferating, thereby potentiating their own proliferation. In certain acute inflammatory responses, such as tissue rejection following a transplant operation, it is desirable not only to reduce the magnitude of the inflammatory response attributable to the existing T cells, but also to reduce the number of T cells generating the immune response. A humanized monoclonal antibody of the invention is especially effective in achieving this aim. As explained above, the biological activity of IL2 already bound to its receptor on the surface of the T cell will be abrogated. However, following such abrogation, a humanized monoclonal antibody of the invention will typically remain bound to IL2 (itself bound to the IL2 receptor) for a certain time, thus targeting the T cell for destruction via antibody-dependent cellular cytotoxicity ("ADCC"). In ADCC, a target cell which is coated with immunoglobulin is killed by an effector cell with Fc receptors recognizing the Fc portion of the immunoglobulin coating the target cell. In most cases, the effector cells participating in ADCC are natural killer ("NK") cells which bear on their surface i.a. the Fc receptor Fc-gamma-RIII. In this way, only cells coated with immunoglobulin are killed, so the specificity of cell killing correlates directly with the binding specificity of the antibody. In the context of the present invention, then, T cells which have become decorated with a humanized monoclonal antibody of the invention via IL2 in complex with its receptor become target cells in the above sense which are then lysed by i.a. an NK cell. The effect is a rapid and effective attenuation of the immune response attributable to cells bearing IL2 receptors, such as T cells.

According to one embodiment of the invention, at least one of the first, third and/or fourth light chain framework region(s) comprised in the human monoclonal antibody or fragment thereof correspond(s) to a human germline sequence for that/those region(s).

According to a further embodiment of the invention, the light chain variable region of a humanized monoclonal antibody or fragment thereof of the invention comprises in its CDR1 region an amino acid sequence as set out in SEQ ID NO: 1. According to a further embodiment of the invention, the light chain variable region of a humanized monoclonal antibody or fragment thereof of the invention comprises in its CDR2 region an amino acid sequence as set out in SEQ ID NO: 2. According to a further embodiment of the invention, the light chain variable region of a humanized monoclonal antibody or fragment thereof of the invention comprises in its CDR3 region an amino acid sequence as set out in SEQ ID NO: 3.

According to a further embodiment of the invention, the light chain variable region of a humanized monoclonal antibody or fragment thereof of the invention further comprises in its CDR1 region an amino acid sequence as set out in SEQ ID NO: 1, in its CDR2 region an amino acid sequence as set out in SEQ ID NO: 2 and in its CDR3 region an amino acid sequence as set out in SEQ ID NO: 3.

According to a further embodiment of the invention, the heavy chain variable region comprises in its CDR1 region an amino acid sequence as set out in SEQ ID NO: 4. According to a further embodiment of the invention, the heavy chain variable region comprises in its CDR2 region an amino acid sequence as set out in SEQ ID NO: 5. According to a further embodiment of the invention, the heavy chain variable region comprises in its CDR3 region an amino acid sequence as set out in SEQ ID NO: 6.

According to a further embodiment of the invention, the heavy chain variable region comprises in its CDR1 region an amino acid sequence as set out in SEQ ID NO: 4, in its CDR2 region an amino acid sequence as set out in SEQ ID NO: 5 and in its CDR3 region an amino acid sequence as set out in SEQ ID NO: 6.

According to a further embodiment of the invention, the light chain variable region of a humanized monoclonal antibody or fragment thereof of the invention further comprises in its CDR1 region an amino acid sequence as set out in SEQ ID NO: 1, in its CDR2 region an amino acid sequence as set out in SEQ ID NO: 2 and in its CDR3 region an amino acid sequence as set out in SEQ ID NO: 3 and the heavy chain variable region comprises in its CDR1 region an amino acid sequence as set out in SEQ ID NO: 4, in its CDR2 region an amino acid sequence as set out in SEQ ID NO: 5 and in its CDR3 region an amino acid sequence as set out in SEQ ID NO: 6. These CDR regions have been found to be especially advantageous in binding to and neutralizing the biological effect of IL2 in the manner described above.

According to a further embodiment of the invention, the amino acid sequence of the first light chain framework region, the remaining amino acid sequences of the second light chain framework region, and the amino acid sequence of the third light chain framework region correspond to any of those of the human germline subgroup VK1 at loci O12, O2, O18, O8, A30, L1, L15, L4, L18, L5, L19, L8, L23, L9, L11 or L12; or the human germline subgroup VL1 at locus 1a; or any of those of the human germline subgroup VL2 at loci 2, 2e, 2a2 or 2b2. In this embodiment, the "remaining amino acid sequences of the second light chain framework region" refer to those amino acids in the second light chain framework region other than the sequence KAPKA. Using the numbering of the VBase database, then, "remaining amino acid sequences of the second light chain framework region" denotes amino acids at positions 35-41 and 47-49 inclusive of the second light chain framework region, regardless of whether this light chain framework region is a V-kappa or a V-lambda framework region (see FIGS. 7a and 8a for numbering of human germline sequences relating to the V-kappa and v-lambda framework region, respectively). Preferred in his embodiment is the further incorporation in the fourth light chain framework region of a sequence corresponding to that found in the human germline sequence JK4, in particular FGGGTKVEIK (SEQ ID NO:14). Other amino acid sequences suitable for use as the fourth light chain framework region include but are not limited to FGQGTKVEIK (SEQ ID NO:15), FGQGTKLEIK (SEQ ID NO:16), FGPGTKVDIK (SEQ ID NO:17), FGQGTRLEIK (SEQ ID NO:18), FGTGTKVTVL (SEQ ID NO:19), FGGGTKLTVL (SEQ ID NO:20) and FGGGTQLTVL (SEQ ID NO:21).

According to a further embodiment, at least one of the first, second and/or third heavy chain framework region(s) comprised in the human monoclonal antibody or fragment thereof correspond(s) to a human germline sequence for that/those region(s).

According to a further embodiment, the amino acid sequence of the first heavy chain framework region, the amino acid sequence of the second heavy chain framework region and the amino acid sequence of the third heavy chain framework region correspond to any of those of the human germline subgroup VH3, in particular at locus 3-07, where the amino acid sequence of the first heavy chain framework region is EVQLVESGGGLVQPGGSLRLSCAASGFTFS (SEQ ID NO:22), the amino acid sequence of the second heavy chain framework region is WVRQAPGKGLEWVA (SEQ ID NO:23) and the amino acid sequence of the third heavy chain framework region is RFTISRDNAKNSLYLQMNSLRAEDTAVYYCAR (SEQ ID NO:24). The amino acid sequence of the fourth heavy chain framework region may advantageously be chose, e.g. in combination with the three framework sequences cited above within germline locus 3-07, from one of the following sequence; WGQGTLVTVSS (SEQ ID NO:25), WGRGTLVTVSS (SEQ ID NO:26), WGQGTMVTVSS (SEQ ID NO:27), WGQGTLVTVSS, WGQGTLVTVSS and WGQGTTVTVSS (SEQ ID NO:28).

In a preferred embodiment, the humanized monoclonal antibody or fragment thereof comprises a light chain variable region comprising an amino acid sequence as set out in SEQ ID NO. 7 and a heavy chain variable region comprising an amino acid sequence as set out in SEQ ID NO. 8. Especially preferred is a humanized monoclonal antibody which comprises a light chain comprising an amino acid sequence as set out in SEQ ID NO. 9 and a heavy chain comprising an amino acid sequence as set out in SEQ ID NO. 10. In the following, the humanized anti-IL2 IgG1 antibody comprising SEQ ID NOs. 9 and 10 and/or SEQ ID NOs. 7 and 8 will be referred to as "Anti-IL2".

The humanized monoclonal antibody may be in the form of an IgG antibody, in particular an IgG1 or IgG4 antibody. As is well known in the art, an IgG comprises not only the variable antibody regions responsible for the highly discriminative antigen recognition and binding, but also the constant regions of the heavy and light antibody polypeptide chains normally present in endogenously produced antibodies and, in some cases, even decoration at one or more sites with carbohydrates, such glycosylation normally being on the Fc portion of IgGs. These Fc portions are known to elicit various effector functions in vivo such as ADCC and complement-dependent cytotoxicity ("CDC"). The mechanism of ADCC is described hereinabove. In CDC, two identical immunoglobulins bind to two identical antigens (for example, here IL2 on a T cell) on the surface of a target cell such that their respective Fc portions come into close proximity to one another. This scenario attracts complement proteins, among them complement proteins, for example C1q, C3, C4 and C9, the latter of which creates a pore in the target cell. The target cell is killed by this perforation. At the same time, the target cell/s also become/s decorated at other locations on its/their surface/s. This decoration attracts effector cells, which then kill the target cell/s in a manner analogous to that described above in the context of the ADCC mechanism (see for example Gelderman et al. (2004), Trends Immunology 25, 158-64).

Advantageously, the IgG antibody is an IgG1 antibody or an IgG4 antibody, formats which are preferred since their mechanism of action in vivo is particularly well understood and characterized. This is especially the case for IgG1 antibodies.

According to a further embodiment of the invention, the fragment of the humanized monoclonal antibody may be an scFv, a single domain antibody, an Fv, a diabody, a tandem diabody, a Fab, a Fab' or a F(ab)$_2$. These formats may generally be divided into two subclasses, namely those which consist of a single polypeptide chain, and those which comprise at least two polypeptide chains. Members of the former subclass include an scFv (comprising one VH region and one VL region joined into a single polypeptide chain via a polypeptide linker); and a single domain antibody (comprising a single antibody variable domain which specifically binds human IL2). Members of the latter subclass include an Fv (comprising one VH region and one VL region as separate polypeptide chains which are non-covalently associated with one another); a diabody (comprising two non-covalently associated polypeptide chains, each of which comprises two antibody variable regions—normally one VH and one VL per polypeptide chain—and arranged such that, upon non-covalent association of a VH on one polypeptide chain with the VL on the respective other polypeptide chain and vice-versa, a bivalent antibody molecule results); a tandem diabody (bispecific single-chain Fv antibodies comprising four covalently linked immunoglobulin variable—VH and VL—regions of two different specificities, forming a homodimer that is twice as large as the diabody described above); a Fab (comprising as one polypeptide chain an entire antibody light chain, itself comprising a VL region and the entire light chain constant region and, as another polypeptide chain, a part of an antibody heavy chain comprising a complete VH region and part of the heavy chain constant region, said two polypeptide chains being intermolecularly connected via an interchain disulfide bond); a Fab' (as a Fab, above, except with additional reduced disulfide bonds comprised on the antibody heavy chain); and a F(ab)2 (comprising two Fab' molecules, each Fab' molecule being linked to the respective other Fab' molecule via interchain disulfide bonds). In general, antibody fragments of the type described hereinabove allow greater flexibility in tailoring, for example, the pharmacokinetic properties of an antibody desired for therapeutic administration to the particular exigencies at hand. For example, it may be desirable to reduce the size of the antibody administered in order to increase the degree of tissue penetration when treating tissues known to be poorly vascularized (for example, joints). Under certain circumstances, it may also be desirable to increase the rate at which the therapeutic antibody is eliminated from the body, said rate generally being acceleratable by decreasing the size of the antibody administered.

According to a further embodiment of the invention, the humanized monoclonal antibody may be present in monovalent monospecific or multivalent mono- or multispecific, in particular bivalent mono- or bispecific forms. In general, a multivalent monospecific, in particular bivalent monospecific antibody may bring with it the therapeutic advantage that the neutralization effected by such an antibody is potentiated by avidity effects, i.e. binding to multiple molecules of the same antigen, here human IL2, by the same antibody. Several monovalent monospecific forms of the antibody of the invention have been described above (for example, an scFv, an Fv or a single domain antibody). Multivalent multispecific, in particular bivalent bispecific forms of the humanized monoclonal anti-human IL2 antibody of the invention may include a full IgG in which one binding arm binds to human IL2 while the other binding arm of which binds to another antigen different from human IL2. A further multivalent multispecific, in particular bivalent bispecific form may advantageously be a humanized single chain bispecific antibody, i.e. a recombinant humanized antibody construct comprising two scFv entities as described above, connected into one contiguous polypeptide chain by a short polypeptide spacer between said two scFv entities as known in the art. Here, one scFv portion of the bispecific single chain antibody comprised within the bispecific single chain antibody will specifically bind human IL2 as set out above, while the respective other scFv portion of this bispecific single chain antibody will bind another antigen determined to be of therapeutic benefit.

According to a further embodiment the humanized monoclonal antibody or fragment thereof may be derivatized, for example with an organic polymer, for example with one or more molecules of polyethylene glycol ("PEG"). As is known in the art, such derivatization can be advantageous in modulating the pharmacodynamic properties of antibodies or fragments thereof.

An scFv is an especially preferred (monovalent monospecific) antibody fragment, especially an scFv comprising an amino acid sequence as set out in SEQ ID NO. 11 or SEQ ID NO. 12.

A further aspect of the invention provides a human monoclonal antibody or fragment thereof comprising an amino acid sequence having at least 70% homology, preferably at least 80, 90, or even better at least 95% homology, with an amino acid as set out in any of SEQ ID NOs: 1-12. Homology may be determined by standard sequence alignment programs such as Vector NTI (InforMax™, Maryland, USA). Such programs compare aligned sequences on an amino acid-by-amino acid basis, and can be set to various levels of stringency for the comparison (e.g. identical amino acid, conservative amino acid substitution, etc.). As the term is used herein, two amino acids in question are considered as being a "conservative substitution" of one another, if they belong to the same main group. By way of non-limiting example, two different amino acids belonging to the group of nonpolar amino acids would be considered a "conservative substitution" of one another, even if these two amino acids were not identical, whereas a nonpolar amino acid on the one hand and a basic amino acid on the other hand would not be considered a "conservative substitution" of one another. Panel 3.1 of "Molecular Biology of the Cell", $4^{th}$ Edition (2002), by Alberts, Johnson, Lewis, Raff, Roberts and Walter groups amino acids into four main groups: acidic, nonpolar, uncharged polar and basic. Such a grouping may be used for the purposes of determining, for the purposes of the present invention, whether a particular amino acid is a "conservative substitution" of another amino acid in question.

Another aspect of the invention provides a polynucleotide molecule. This polynucleotide molecule comprises a nucleotide sequence encoding an amino acid sequence as set out in any of SEQ ID NOs. 1-12 or a nucleotide sequence exhibiting at least 60%, preferably at least 65, 70, 75, 80, 85, 90, or 95% homology with said nucleotide sequence. Here, homology may be determined by comparing a polynucleotide molecule comprising a nucleotide sequence encoding an amino acid sequence of any of SEQ ID NOs: 1-12 with a polynucleotide molecule having a nucleotide sequence in question ("test sequence") by sequence alignment, and wherein a nucleotide in the test sequence is considered homologous if it is either identical to the corresponding nucleotide in the nucleotide sequence encoding a corresponding amino acid sequence of any of SEQ ID NOs: 1-12 or if one or more nucleotide deviation(s) in the test sequence from corresponding nucleotide(s) in the nucleotide sequence encoding an amino acid sequence of any of SEQ ID NOs: 1-12 results in a nucleotide triplet which, when translated, results in an amino acid which is either identical to (due to a degenerate triplet) or a conservative substitution of the corresponding amino acid in the corresponding amino acid sequence of any of SEQ ID NOs: 1-12. Here, the term "conservative substitution" is to be understood as described above.

A further aspect of the invention provides a pharmaceutical composition comprising a humanized monoclonal antibody or fragment thereof or a polynucleotide molecule having a nucleotide sequence encoding an amino acid sequence as set out in any of SEQ ID NOs. 1-12 or encoding an amino acid sequence comprising an amino acid sequence bearing at least 70% homology to any of SEQ ID NOs. 1-12, wherein "homology" is to be understood as explained hereinabove.

In accordance with this invention, the term "pharmaceutical composition" relates to a composition for administration to a mammalian patient, preferably a human patient. In a preferred embodiment, the pharmaceutical composition comprises a composition for parenteral injection or infusion. Such parenteral injection or infusion may take advantage of a resorption process in the form of e.g. an intracutaneous, a subcutaneous, an intramuscular and/or an intraperitoneal injection or infusion. Alternatively, such parenteral injection or infusion may circumvent resorption processes and be in the form of e.g. an intracardial, an intraarterial, an intraveneous, an intralumbal and/or an intrathecal injection or infusion. In another preferred embodiment, the pharmaceutical composition comprises a composition for administration via the skin. One example of administration via the skin is an epicutaneous administration, in which the pharmaceutical composition is applied as e.g. a solution, a suspension, an emulsion, a foam, an unguent, an ointment, a paste and/or a patch to the skin. Alternatively, administration of the pharmaceutical composition may be effected via one or more mucous membranes. For example, administration may be buccal, lingual or sublingual, i.e. via the mucous membrane(s) of the mouth and/or tongue, and may be applied as e.g. a tablet, a lozenge, a sugar coated pill (i.e. dragée) and/or as solution for gargling. Alternatively, administration may be enteral, i.e. via the mucous membrane(s) of the stomach and/or intestinal tract, and may be applied as e.g. a tablet, a sugar coated pill (i.e. dragée), a capsule, a solution, a suspension and/or an emulsion. Alternatively, administration may be rectal, and may be applied as e.g. a suppository, a rectal capsule and/or an ointment or unguent. Alternatively, administration may be intranasal, and may be applied as e.g. drops, an ointment or unguent and/or a spray. Alternatively, administration may be pulmonary, i.e. via the mucous membrane(s) of the bronchi and/or the alveolae, and may be applied as e.g. an aerosol and/or an inhalate. Alternatively, administration may be conjunctival, and may be applied as e.g. eye drops, an eye ointment and/or an eye rinse. Alternatively, administration may be effected via the mucous membrane(s) of the urogenital tract, e.g. may be intravaginal or intraurethral, and may be applied as e.g. a suppository, an ointment and/or a stylus. It should be understood that the above administration alternatives are not mutually exclusive, and that a combination of any number of them may constitute an effective therapeutic regimen.

The pharmaceutical composition of the present invention may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Preparations for e.g. parenteral administration include sterile aqueous or non-aqueous solutions, suspensions, emulsions and liposomes. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles suitable for general parenteral administration include sodium chloride solution, Ringer's dextrose, dextrose and sodium chloride, lactated Ringer's, or fixed oils. Vehicles suitable for intravenous or intraarterial administration include fluid and nutrient replenishers, electrolyte replenishers (such as those based on Ringer's dextrose), and the like. Preservatives and other additives may also be present such as, for example, antimicrobials, anti-oxidants, chelating agents, inert gases and the like. In addition, the pharmaceutical composition of the present invention might comprise proteinaceous carriers, like, e.g., serum albumin or immunoglobulin, preferably of human origin. It is envisaged that the pharmaceutical composition of the invention might comprise, in addition to the humanized monoclonal antibody or fragment thereof (as described in this invention), further biologically active agents, depending on the intended use of the pharmaceutical composition. Such agents might be drugs acting on the gastro-intestinal system, drugs acting as cytostatica, drugs preventing hyperurikemia, drugs inhibiting immunoreactions (e.g. corticosteroids), drugs modulating the inflammatory response, drugs acting on the circulatory system and/or agents such as cytokines known in the art.

A further aspect of the invention provides a use of a humanized monoclonal antibody or fragment thereof as set out hereinabove or of a polynucleotide molecule as set out hereinabove in the manufacture of a medicament, optionally comprising one or more additional anti-inflammatory agents, for the treatment of inflammatory diseases in mammals, preferably humans. Advantageously, such inflammatory diseases are chosen from the group consisting of rheumatoid arthritis (RA), asthma, multiple sclerosis (MS), chronic obstructive pulmonary disease (COPD), Acute Respiratory Distress Syndrome (ARDS), Idiopathic Pulmonary Fibrosis (IPF), Inflammatory Bowel Disease (IBD), uveitis, macular degeneration, colitis, psoriasis, Wallerian Degeneration, antiphospholipid syndrome (APS), acute coronary syndrome, restinosis, atherosclerosis, relapsing polychondritis (RP), acute or chronic hepatitis, failed orthopedic implants, glomerulonephritis, lupus, autoimmune disorders, acute pancreatitis or ankylosing spondylitis (AS).

A further aspect of the invention provides a use of a humanized monoclonal antibody or fragment thereof as set out hereinabove or of a polynucleotide molecule as set out hereinabove in the manufacture of a medicament, optionally comprising one or more additional anti-cancer agents, for the treatment of a tumorous disease or another condition with delayed cell apoptosis, increased cell survival or proliferation in mammals, preferably humans. Preferably, the tumorous disease is a cancer, said cancer preferably being a leukaemia, multiple myeloma, gastric carcinoma or skin carcinoma.

A further aspect of the invention provides a method of treating an inflammatory disease in which a humanized monoclonal antibody or fragment thereof as set out hereinabove or a polynucleotide molecule as set out hereinabove is administered (optionally together with one or more additional anti-inflammatory agents) to a mammalian, preferably to a human subject in a sufficient amount and for a sufficient time to prevent and/or ameliorate said inflammatory disease. Advantageously, such inflammatory diseases are chosen from the group consisting of rheumatoid arthritis (RA), asthma, multiple sclerosis (MS), chronic obstructive pulmonary disease (COPD), Acute Respiratory Distress Syndrome (ARDS), Idiopathic Pulmonary Fibrosis (IPF), Inflammatory Bowel Disease (IBD), uveitis, macular degeneration, colitis, psoriasis, Wallerian Degeneration, antiphospholipid syndrome (APS), acute coronary syndrome, restinosis, atherosclerosis, relapsing polychondritis (RP), acute or chronic hepatitis, failed orthopedic implants, glomerulonephritis, lupus, autoimmune disorders, acute pancreatitis or ankylosing spondylitis (AS).

A further aspect of the invention provides a method of treating a tumorous disease in which a humanized monoclonal antibody or fragment thereof as set out hereinabove or a polynucleotide molecule as set out hereinabove is administered (optionally together with one or more additional anti-cancer agents) to a mammalian, preferably to a human subject in a sufficient amount and for a sufficient time to prevent and/or ameliorate said tumorous disease or another condition with delayed cell apoptosis, increased cell survival or proliferation. Preferably, the tumorous disease is a cancer, said cancer preferably being a leukaemia, multiple myeloma, gastric carcinoma or skin carcinoma.

The invention will now be illustrated by way of the following non-limiting figures and examples. An overview of the figures is as follows:

FIG. 1 Retained antigen binding after humanization of VL region

Figure 2:
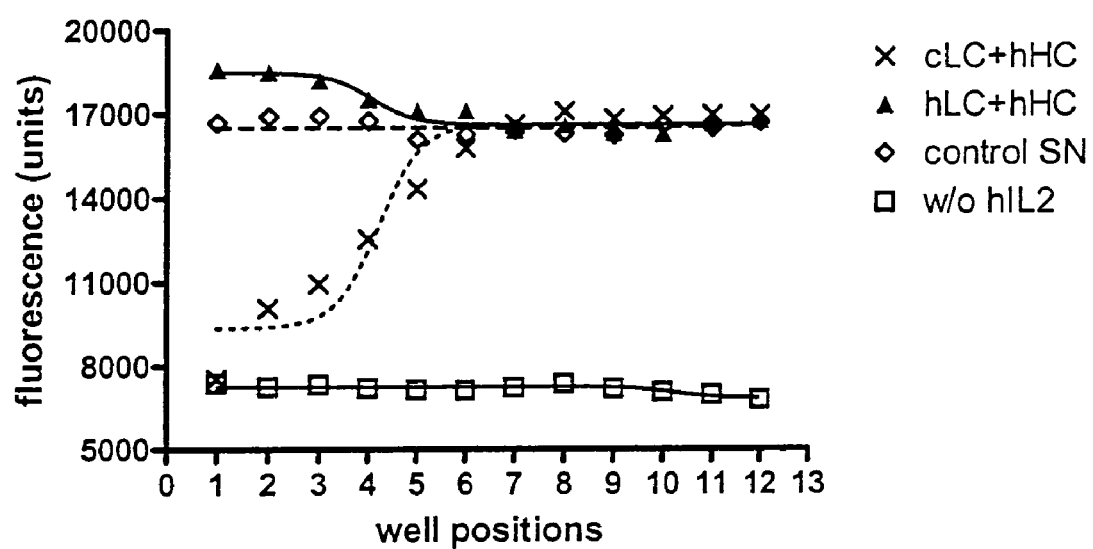

FIG. 2 Loss of neutralizing activity after humanization of VL region

Figure 3:
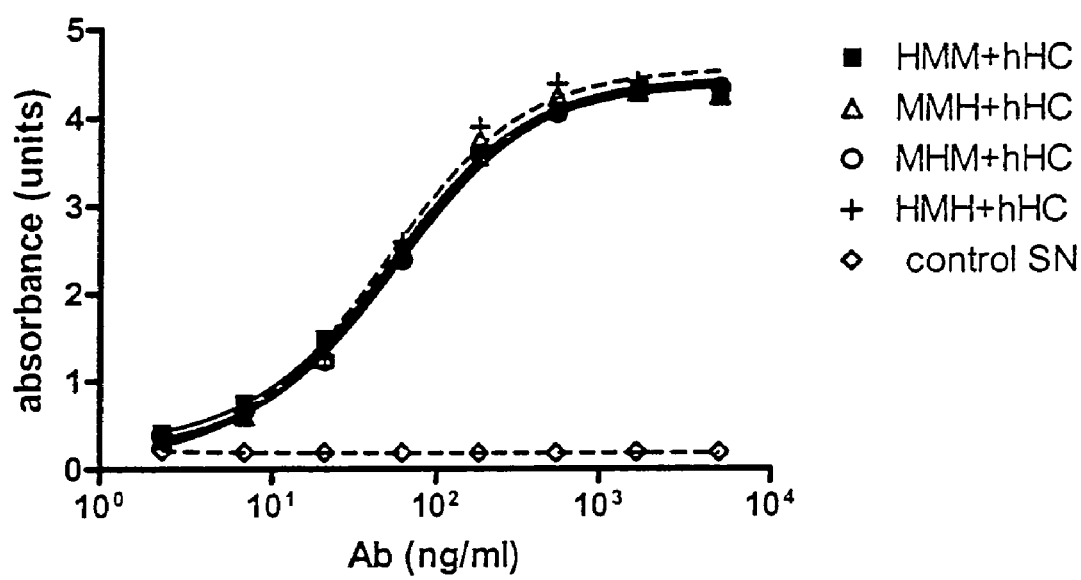
Figure 4:
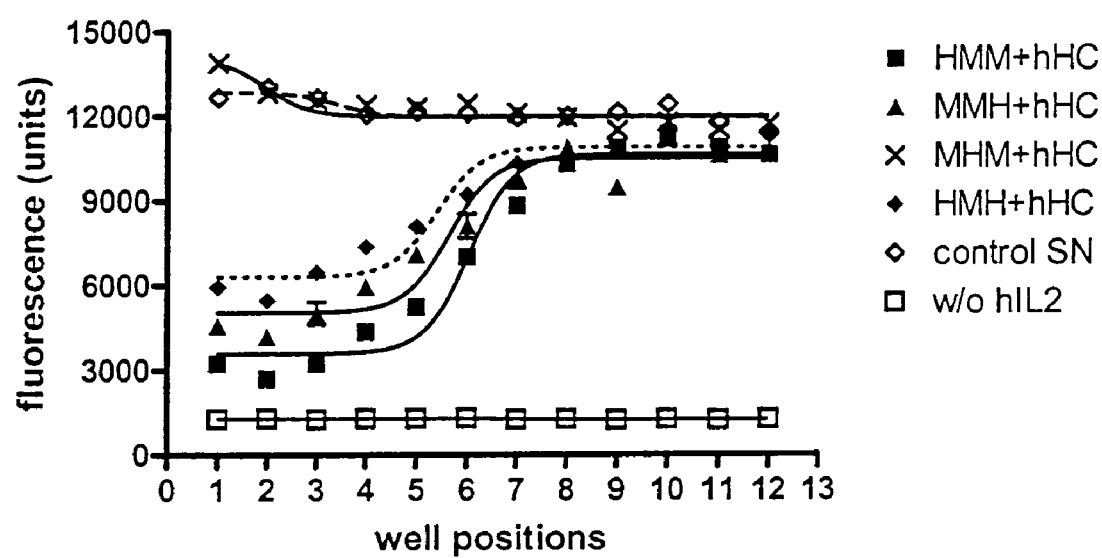
Figure 5:
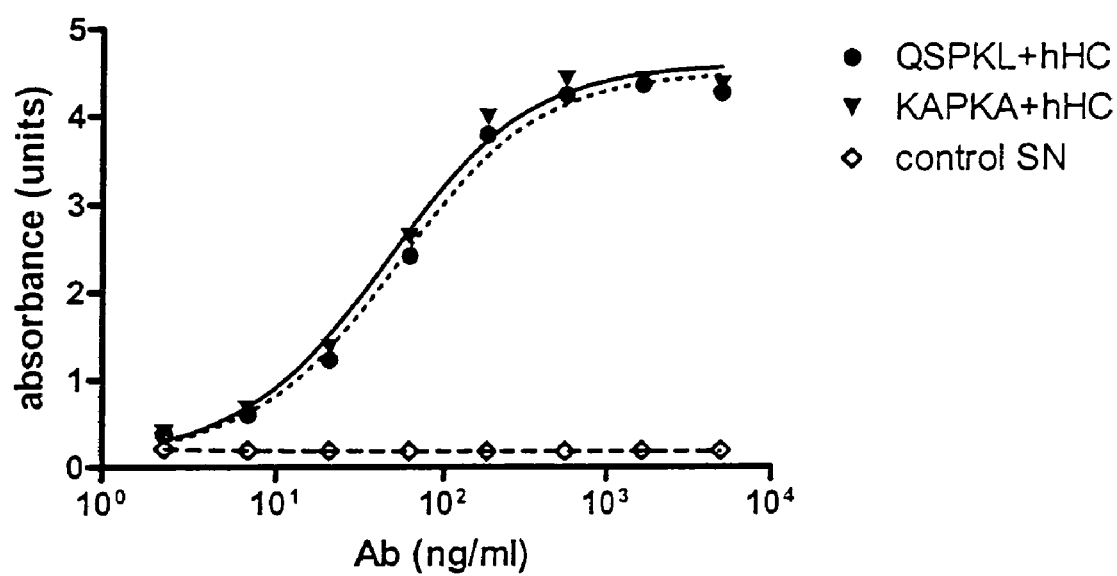
Figure 6:
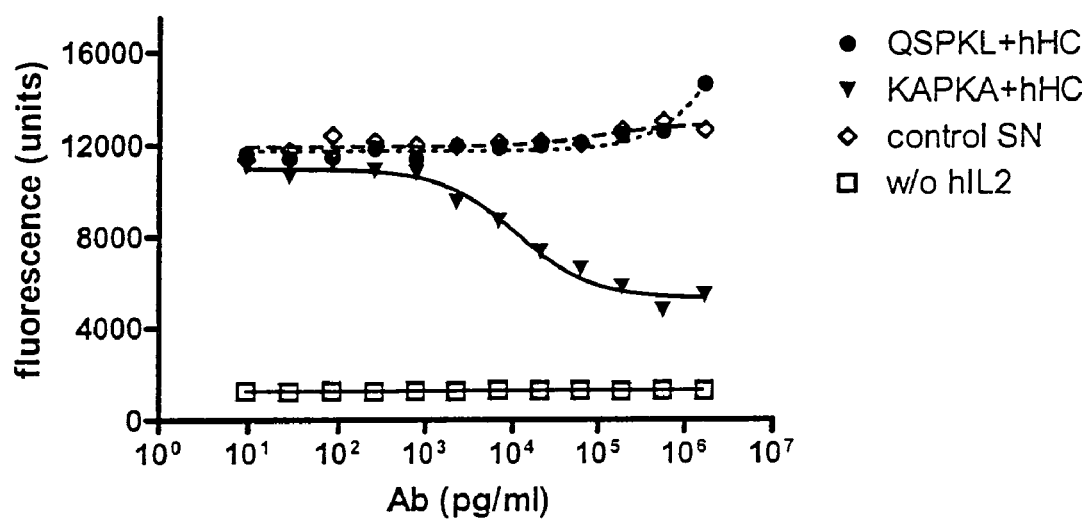

FIG. 3 Binding of IL2 is not affected by human/mouse framework exchanges within the VL region FIG. 4 Loss of neutralization activity following incorporation of a human second light chain framework FIG. 5 Amino acid changes at positions 42-46 of the VL region (within second light chain framework) do not affect antigen binding FIG. 6 Mutation of leucine to alanine at position 46 of the second light chain framework leads to a regaining of neutralization activity FIG. 7a Human germline amino acid sequences for first and second light chain framework regions (V-kappa). CDR regions have been omitted; the remaining numbering of the remaining framework regions is as published in the online "Vbase" database (see above for weblink).

FIG. 7*b* Human germline amino acid sequences for the third light chain framework region (V-kappa). CDR regions have been omitted; the remaining numbering of the remaining framework regions is as published in the online "Vbase" database (see above for weblink).

FIG. 8*a* Human germline amino acid sequences for first and second light chain framework regions (V-lamdba). CDR regions have been omitted; the remaining numbering of the remaining framework regions is as published in the online "Vbase" database (see above for weblink).

FIG. 8*b* Human germline amino acid sequences for the third light chain framework region (V-kappa). CDR regions have been omitted; the remaining numbering of the remaining framework regions is as published in the online "Vbase" database (see above for weblink).

FIG. 9*a* Human germline amino acid sequences for first and second heavy chain framework regions. CDR regions have been omitted; the remaining numbering of the remaining framework regions is as published in the online "Vbase" database (see above for weblink).

FIG. 9*b* Human germline amino acid sequences for the third heavy chain framework region. CDR regions have been omitted; the remaining numbering of the remaining framework regions is as published in the online "Vbase" database (see above for weblink).

FIG. 10 Specificity of binding of humanized anti-IL2 antibody "Anti-IL2" to the natural killer lymphoma cell line NKL FIG. 11 Anti-IL2 abrogates IL2-dependent IL2-dependent up-regulation of CD124 cell surface expression on CTLL-2 cells FIG. 12 Anti-IL2 specifically blocks IL2 signal transduction downstream of the IL2 receptor FIG. 13 The efficacy of Anti-IL2 and Daclizumab is differentially affected by CD25 expression level FIG. 14 Results showing the impact of Anti-Il2 and Daclizumab on IL2-dependent proliferation of primary human NK cells FIG. 15 Results showing the impact of Anti-Il2 and Daclizumab on IL2-dependent release of IFN-gamma by NK cells

EXAMPLE 1

Procurement of Human IL2 ("hIL2") Antigen

The purpose of the experimental approaches described below in Examples 1a, 1b and 1c was to provide recombinant IL2 antigen material derived from different sources: antigen expressed in prokaryotic cells, in eukaryotic cells and recombinant protein antigen commercially available as a certified therapeutic.

EXAMPLE 1a

Recombinant Expression from *E. coli*

The mature hIL2 (i.e., encoding amino acid residues APTSSS . . . IISTLT) was cloned as a single open reading frame ("ORF") into the prokaryotic expression vector pBAD (Invitrogen) using standard PCR and molecular biology technology. At the 5'-end three nucleotides encoding a methionine were added, on the 3'-end a nucleotide sequence was inserted before the stop codon that fuses a hexahistidine-tag to the C-terminus of the protein.

This construct was used to transform competent *E. coli* (strain BL21 (DE3), Stratagene) using the instructions provided by the manufacturer. Bacteria were grown in standard LB medium to a density of OD(600 nm)=0.5, then L-arabinose was added to a concentration of 0.2% w/v to trigger expression for 5 h. Harvest of *E. coli* was performed by centrifugation at 10,000 g for 15 min. Then the insoluble fraction (inclusion bodies) was prepared using the BugBuster reagent and protocol (Novagen) according to the manufacturer's instructions.

Inclusion bodies were solubilized in 6 M Guanidine-hydrochloride ("GuHCl"), and were then diluted to 0.1 mg/ml with a buffer containing 2 M GuHCl (pH=8.0)/1 mM Glutathione-ox/10 mM Glutathione-red and incubated for 16 h at 20° C. After incubation, pH was adjusted to 6.0 by slow addition of glacial acetic acid while stirring vigorously. Finally, three sequential chromatography approaches were applied to obtain a highly purified and homogenous protein preparation of hIL2his: immobilized metal affinity chromatography (IMAC), reversed phase HPLC, ion exchange chromatography. The functionality of the purified protein was verified in a cellular proliferation experiment (see below).

EXAMPLE 1b

Recombinant Expression from Mammalian Cells

The mature hIL2 (i.e., encoding amino acid residues APTSSS . . . IISTLT) was cloned into the eukaryotic expression vector pEFdhfr (Mack M. et al. (1995) PNAS 92, 7021-5) using standard PCR and molecular biology technology. At the 5'-end a nucleotide sequence encoding a leader peptide of human IgG was added to allow for efficient processing and secretion, on the 3'-end a nucleotide sequence was inserted before the stop-codon that fuses a hexahistidine-tag to the C-terminus of the protein.

293 cells (DSMZ, order code ACC305) were seeded at a density of 25-35% plate surface coverage and cultured for 24 h. Then the cells were transfected with the pEFdhfr-hIL2 expression vector using the "Transfast" reagent (Promega) according to the manufacturer's instructions. After an additional 60 h culture period, cellular supernatants were harvested and hIL2-his protein was purified using an IMAC approach, followed by ion-exchange chromatography. Functionality of the purified protein was verified in a cellular proliferation experiment.

EXAMPLE 1c

Purchase as Proleukin

Proleukin (formulated recombinant hIL2, expressed in *E. coli*) was purchased from Chiron.

With the above approaches three different supplies of fully functional recombinant hIL2 antigen were made available.

EXAMPLE 2

Generation of Humanized Monoclonal Anti-hIL2 Antibody

It was desired to generate a humanized monoclonal antibody ("mAb") with a particularly favorable mode of action and that specifically targets human hIL2 and neutralizes its bioactivity. In general, neutralizing mAbs targeting a secreted soluble protein, such as the cytokine hIL2, recognize an epitope that is at least partially overlapping with the epitope recognized by a component of the corresponding cytokine receptor. Thus, the mAb directly competes with the receptor for binding to the cytokine. This mechanism of action implies that neutralization can effectively be achieved. The mAb must be applied at a sufficiently high dose in order to out-compete the cytokine receptor.

EXAMPLE 2a

Starting Point-->Commercially Available Monoclonal Anti-hIL2 Antibody as Protein To gain an understanding of the extent to which different anti-hIL2 mAbs could neutralize as mentioned above, anti-hIL2 mAbs were produced by immunization of mice, followed by harvest of spleen cells and hybridoma fusion, all according to standard protocols. In addition, commercially available anti-hIL2 mAbs were purchased. The pool of available mAbs was used to compare features of the different antibodies in three assays: binding to soluble antigen as tested by ELISA, binding to cell surface-associated antigen as tested by FACS, and capacity for neutralization of hIL2 bioactivity as tested by a cellular proliferation assay.

The ELISA assay was performed as follows:

All incubations were performed at 20° C. Streptavidin-coated 96-well ELISA plates (Nunc) were used to attach PEG-biotinylated Proleukin, 0.1 µg in 100 µl PBS-TB (phosphate buffered saline, pH=7.4, 0.05% v/v Tween-20, 1% w/v BSA) per well for 30 minutes. Then the plate was washed 3 times with 200 µl per well PBS-T (phosphate buffered saline, pH=7.4, 0.05% v/v Tween-20). The different mAb samples were added, 100 µl per well and samples were incubated for 1 hour. Then the plate was washed 3 times with 200 µl per well PBS-T. The detection antibody applied was a goat anti-human IgG HRP-conjugated mAb, (Jackson Immunoresearch), diluted 1:1000 in PBS-TB, 100 µl per well and incubation for 1 hour. Then the plate was washed 3 times with 200 µl per well PBS-T. Antibody binding to antigen finally was quantified by incubation with the HRP substrate: 100 µl 2,2'-azino-di [3-ethyl-benzthiazoline-6-sulphonic acid] ("ABTS") substrate buffer (Roche Diagnostics, ABTS tablets) and the plate was incubated for 5 to 10 minutes until green dye developed. The staining was measured at 405 nm on a 96-well plate reader.

The FACS assay was performed as follows:

For optimal growth under cell culture conditions, the human natural killer lymphoma cell line NKL depends on the presence of about 5 ng/ml hIL2 in the medium (Basal Iscove's medium (Biochrom AG); 10% v/v fetal bovine serum (Biochrom AG); 100 µg/ml Penicillin/Streptomycin (Biochrom AG)). NKL cells, $1 \times 10^6$ per ml, were deprived of hIL2 for 24 hours in preparation of the experiment by culturing in hIL2-free medium. Immediately prior to the experiment, the cells were washed with hIL2-free medium. All following incubations were done at 4° C. for 30 minutes; for washing, the PBS-F buffer (phosphate buffered saline, 3% v/v fetal bovine serum) was used at 4° C., as well. First $2 \times 10^5$ NKL cells in 200 µl medium were incubated with 1 µg of recombinant human hIL2 or left without hIL2 under the same conditions. Subsequently, cells were washed 3 times, each wash with 2 ml PBS-F. Then $2 \times 10^5$ cells were incubated with the different mouse anti-hIL2 mAbs, 1 µg in 200 µl medium, at 4° C. for 30 minutes. The cells were washed again three times, as indicated above, and lastly incubated with a FITC-conjugated goat anti-mouse IgG detection mAb (Jackson Immunoresearch), diluted 1:1000 in 200 µl PBS-F. After three additional washes, cellular fluorescence of cells holding hIL2 on their surface versus plain cells was analyzed on a FACS machine.

The proliferation assay was performed as follows:

For optimal growth under cell culture conditions, the murine CTL cell line CTLL-2 (LGCPromochem) depends on the presence of about 5 ng/ml hIL2 in the medium (Basal Iscove's medium (Biochrom AG); 10% v/v fetal bovine serum (Biochrom AG); 100 µg/ml Penicillin/Streptomycin (Biochrom AG); 0.5 mM 2-Mercaptoethanol (Gibco)). Both mouse and human hIL2 work equally well maintaining survival and proliferation of CTLL-2 cells. CTLL-2 cells, $1 \times 10^6$ per ml, were deprived of hIL2 for 12 hours in preparation of the experiment by culturing in hIL2-free medium.

Immediately prior to the experiment, the cells were washed with hIL2-free medium. A 96-well tissue culture plate was used to perform the proliferation experiment and assess inhibition of hIL2 bioactivity by the different mAbs. A final assay volume of 200 µl was applied per well, this volume including: $5 \times 10^4$ CTLL-2 cells, 2 ng/ml hIL2 (to allow for approximately half-maximal proliferation) and the different anti-hIL2 mAbs at a concentration of 5000 ng/ml, 1000 ng/ml, 200 ng/ml and 40 ng/ml. All samples were prepared in triplicate. The respective mixtures were incubated 48 hours at 37° C. in a humidified chamber in the presence of 5% carbon dioxide. Then viable cells were detected using the AlamarBlue fluorescent dye readout (Biosource International) and a 96-well fluorescence plate reader according to the manufacturer's recommendation.

The mAb202 (commercially available from R&D Systems) was found to (i) bind to soluble antigen, (ii) bind to cell surface-associated antigen, and (iii) efficiently neutralize hIL2 bioactivity. Among the antibodies tested, only mAb 202 scored in all three assays and therefore was considered a promising candidate according to the features defined above and was therefore chosen as a starting point for subsequent experiments.

EXAMPLE 2b

Determination of Primary Sequence of Anti-hIL2 Antibody by Sequencing: Identification of Sequences from the Variable Region of the Heavy Chain ("VH") and the Variable Region of the Light Chain ("VL")

Due to lack of availability of the mAb202 hybridoma clone, the mAb was sequenced to identify VH and VL amino acid sequences. To this end, Fab fragments of mAb202 were prepared. These fragments were subjected to proteolytic digestion with online HPLC for peptide separation. Subsequently, the individual peptides were analyzed with respect to amino acid composition and sequence by an MS/MS mass spectrometry. This approach led to identification of VH and VL protein sequences.

EXAMPLE 2c

Control for Retained Functionality: Fusion of Sequenced VH/VL Regions with Known Mouse Constant Regions A functional verification of the sequencing results obtained from mAb202 protein sequencing described above was desired. Thus, a gene encoding the sequenced VH was synthesized and cloned into an expression vector providing the constant regions of a mouse IgG1. Likewise, a gene encoding the sequenced VL was synthesized and cloned into an expression vector providing a mouse C kappa domain. These two expression vectors would ideally allow reconstruction of the original mAb202, the functionality of which could then be re-tested as above. After co-expression of both vectors in 293 cells, an anti-IL2 mAb was detected in the cellular supernatants with features comparable to those observed with the original mAb202. The concordance of activity (by ELISA as well as in a a proliferation assay using a CTLL-2 cell line) observed for the reconstructed mAb following protein sequencing with those of the parental mAb202 may be taken as a confirmation that the sequences determined for the VH and VL regions of this antibody were correct.

EXAMPLE 2d

Humanization of Heavy Chain

The intention of humanization is to fully retain binding specificity and biological activity of an antibody while minimizing the content of non-human sequence present in a mAb. The latter aim results in an antibody which is less likely to elicit an immune response when administered to a human subject than its parent antibody, of non-human origin. Initially, an expression vector for a chimeric heavy chain comprising the original mouse VH together with C1, C2 and C3 domains of human IgG1 isotype was generated. After expression of the chimeric heavy chain, when combined with the chimeric light chain (see below), the features of the original mouse mAb could be reproduced (see below). The next logical step was to humanize the VH region. In order to avoid changes in specificity, the CDR sequences remained unchanged. Therefore, on the basis of the original mouse VH, the most closely related human VH framework sequence was searched. Of all human VH frameworks, human framework 1-3/3-07/J6 was found to bear the highest degree of homology to the original murine framework. Human framework 1-3/3-07/J6 was found to differ in 16 amino acid residues from the corresponding mouse VH frameworks. The alignment below shows a direct comparison between original mouse and human 1-3/3-07/J6 VH frameworks; original CDR sequences are underlined and amino acid identity between both sequences is indicated by an asterisk.

```
VH_mouse      DVRLVESGGGLVKPGGSLKLSCAAYGFTFSSYTLAWVRQTPEKRLEWVAAIDSSSYTYSPDTVRG
1-3/3-07/J6   (SEQ ID NO: 29)

EVQLVESGGGLVQPGGSLRLSCAASGFTFSSYTLAWVRQAPGKGLEWVAAIDSSSYTYSPDTVRG
              z* ********* ***** ***** ************** * * *********************
              (SEQ ID NO: 30)

VH_mouse      RFTISRDNAKNTLYLQMSSLKSEDTAMYYCTRDSNWDALDYWGQGTSVIVSS
1-3/3-07/J6   (SEQ ID NO: 31)

RFTISRDNAKNSLYLQMNSLRAEDTAVYYCARDSNWDALDYWGQGTTVTVSS
              ********* * zz** * *************** * ***
              (SEQ ID NO: 32)
```

The constructs containing the original mouse VH or the humanized VH will in the following text be respectively referred to as cHC (chimeric heavy chain comprising a mouse VH and human C1, C2, C3) and hHC (humanized heavy chain comprising a VH containing mouse CDR regions within a human VH framework and human C1, C2, C3). For purposes of recombinant protein expression of the humanized heavy chain, open reading frames encoding the humanized VH in combination with C1, C2 and C3 domains of human IgG1 isotype were cloned into a suitable vector (Raum T et al. (2001) Cancer Immunol Immunother. 50, 141-50).

EXAMPLE 2e

Humanization of Light Chain

Humanization was performed analogously to the approach described above for the heavy chain. In brief, an expression vector for a chimeric light chain comprising the original mouse VL together with a human Ck domain was generated and tested after co-expression with the chimeric heavy chain (see above). Again, as a second step, on the basis of the original mouse VL the most closely related human VL framework sequence was searched. All three CDRs were retained. Human VL framework 012/Jk4 turned out to be the closest relative in sequence. A total of 22 amino acid residues were different in the VL frameworks between the mouse VL and human 012/Jk4. The alignment below shows a direct comparison between original mouse and human 012/Jk4 frameworks; original CDR sequences are underlined, amino acid identity between both sequences is indicated by an asterisk.

```
VL_mouse  DIVMTQSQKFMSTSVGDRVSVTCKASQNVGTNVGWYQQKPGQSPKALIYSASFRYS
012/Jk4   (SEQ ID NO: 33)
```

```
DIQMTQSPSSLSASVGDRVTITCKASQNVGTNVGWYQQKPGKAPKLLIYSASFRYS
** ****zzzz* ******zz**********************zz** **********
   (SEQ ID NO: 34)

VL_mouse GVPDRFTGSGSGTDFSLTISNVKSEDLAEYFCQQYYTYPYTFGGGTKLEIK
O12/Jk4  (SEQ ID NO: 35)

GVPSRFSGSGSGTDFTLTISSLQPEDFATYYCQQYYTYPYTFGGGTKVEIK
         *** ** ******** ****zzzz** * * *************** ***
         (SEQ ID NO: 36)
```

The constructs containing the original mouse VL or the humanized VL will in the following text be respectively referred to as cLC (chimeric light chain comprising a mouse VL and human Ckappa) and hLC (humanized light chain comprising a VL containing mouse CDR regions within a human VL framework and human Ckappa). For purposes of recombinant protein expression of the humanized light chain, open reading frames encoding the humanized VL in combination with the human Ck domain were cloned into a suitable vector (Raum T et al. (2001) Cancer Immunol Immunother. 50, 141-50).

EXAMPLE 2e.1

Permutation of Human and Mouse Sequences as Entire Framework Regions; Evaluation of Binding and Neutralization by a Proliferation Assay After successful humanization of both the heavy and the light chain had been performed, features of the resulting humanized mAbs were tested in comparison to the chimeric mAb, i.e. the antibody molecule containing fully murine variable domains. Since the chimeric mAb showed neutralization of IL2 bioactivity comparable to the original mAb, it was used as a reference for these experiments. Pairs of expression vectors encoding heavy and light chains were used for transient co-transfection of 293 cells (the applied protocol was identical to the transfection procedure described in Example 1b, except that the cells were transfected with two plasmids simultaneously).

After expression in 293 cells comparable quantities of the different mAb versions in the cellular supernatants were verified by an anti-hIgG ELISA, which was carried out as follows: A 96-well ELISA plate (Nunc) was incubated with a 1:2,000 dilution in PBS of the anti-hIgG mAb (Abcam LTD), 100 µl per well, 12 hours at 4° C. Each well was washed 3 times with 200 µl of PBS-T buffer, then 100 µl of neat supernatants harvested from 293 cells and serial dilution of supernatants in medium were filled into each well and incubated for 1 hour at 20° C. Again, each well was washed 3 times with 200 µl of PBS-T buffer. A 1:1,000 dilution in PBS-TB of the goat anti-human IgG HRP-conjugated mAb (Jackson Immunoresearch) was added to the wells, 100 µl per well and incubated for 1 hour at 20° C. Then the plate was washed 3 times with 200 µl per well PBS-T. Antibody binding to hIgG finally was quantified by incubation with the HRP substrate: 100 µl ABTS substrate buffer (Roche Diagnostics, ABTS tablets) and the plate incubated for 5 to 10 minutes until green dye developed. The staining was measured at 405 nm on a 96-well plate reader. Only supernatants with comparable quantities of mAb were used for all follow up experiments. Antigen-binding of the various mAbs was tested by ELISA (see above).

The features of the generated mAbs regarding binding of soluble antigen and regarding neutralization of IL2 bioactivity was analysed by ELISA and a CTLL-2 proliferation assay, respectively (see Example 2a above for detailed experimental protocols). In the ELISA experiment, increasing absorbance units will be indicative for increased amounts of mAb binding to hIL2 antigen. In the CTLL-2 proliferation assay, increasing fluorescence units will be indicative for an increased number of metabolically active (=alive) cells. All cellular supernatants ("SN") containing the different mAb versions were controlled for even mAb concentrations by an anti-hIgG ELISA before they were subjected to the following experiments. The results of a representative experiment are shown in FIG. 1. Here, both combinations hLC+h-HC (hLC=humanized light chain, hHC=humanized heavy chain) and cLC+hHC (cLC=chimeric light chain) show comparable binding to hIL2 antigen. The results from the CTLL-2 assay (FIG. 2) show that hLH+hHC does not lead to any detectable neutralization of hIL2 bioactivity because detected fluorescence is not different from the control SN. In contrast, cLH+hHC reduces the number of living cells as evident by a mAb concentration-dependent reduction in fluorescence. Application of the two individual chains cLC or hHC in this assay had no impact on hIL2-dependent cell survival (data not shown). Each data point in the representative experiment shown in FIG. 2 represents the mean result of duplicate samples. The results of the assays described are summarized in Table 1:

TABLE 1

| light chain | heavy chain | antigen binding | Neutralization |
|---|---|---|---|
| hLC | HHC | + | − |
| cLC | HHC | + | + |

These results demonstrate that despite binding to soluble antigen appears not to be different neutralization is lost as soon as hLC is used with the humanized heavy chain variant. The conclusion is that humanization of VL entailed some functional impairment for the mAb.

In order to determine where, i.e. within which framework region, this impairment was introduced, humanization of the VL framework of cLC was performed in different segments, changing only a single framework at a time (i.e. framework region 1, framework region 2 or framework region 3) rather than all three frameworks at a time from mouse to human. An abbreviated nomenclature was developed, and will be used hereinbelow, in designating these humanization variants. According to this nomenclature, three capital letters are used to create triplets designating each of the first three framework regions 1, 2 and 3, wherein the first position of the triplet designates the nature of framework region 1, second position of the triplet designates the nature of framework region 2, and the third position of the triplet designates the nature of framework region 3. For example, "HMM" would indicate a human framework region 1 in a VL that is otherwise of murine origin, whereas "MHM" indicates that only framework region 2 is human, whereas framework regions 1 and 3 are of murine origin.

The features of the different human/mouse hybrid VL domains were analyzed with respect to their effects. Again, binding of hIL2 antigen and neutralization of IL2 bioactivity were analysed by ELISA and a CTLL-2 proliferation assay, respectively (see Example 2a above for detailed experimental protocols). In the ELISA experiment, increasing absorbance units are indicative of increased amounts of mAb binding to hIL2 antigen. In the CTLL-2 proliferation assay, increasing fluorescence units are indicative of an increased number of metabolically active (=alive) cells. All cellular supernatants ("SN") containing the different mAb versions were controlled for uniform mAb concentrations using an anti-hIgG ELISA before they were subjected to the following experiments. FIG. 3 shows the results from a representative comparative experiment. Here, it can be seen that all human/mouse hybrid VL versions show comparable binding to hIL2 antigen when combined with hHC. The results of the CTLL-2 assay (FIG. 4) show that neutralization of hIL2 bioactivity is only observed as long as VL framework 2 is murine; MHM+ hHC did not change the number of living cells compared to control SN. Each data point in the representative experiment shown in FIG. 4 represents the mean of duplicate samples. The results of the assays described are summarized in Table 2:

TABLE 2

| light chain | heavy chain | antigen binding | Neutralization |
| --- | --- | --- | --- |
| HMM | HHC | + | + |
| MHM | HHC | + | − |
| MMH | HHC | + | + |
| HMH | HHC | + | + |

These experiments show quite clearly that framework 2 of the VL determines whether or not the mAb is capable of neutralizing IL2 bioactivity. A more detailed comparison of mouse and human sequences of framework 2 reveals that these sequences differ in three amino acids.

Specifically, the mouse framework 2 comprises the partial amino acid sequence QSPKA (SEQ ID NO:37), whereas the corresponding human sequence is KAPKL (SEQ ID NO:38) (amino acids differing between human and mouse species have been underline for clarity).

EXAMPLE 2e.2

Permutation of Human and Any Mouse Sequences within Framework 2; Evaluation of Binding and Neutralization by a Proliferation Assay and a Target Gene Induction Assay To determine whether all three amino acid changes or only some are decisive in terms of providing a neutralizing mAb, an additional set of experiments was performed. To this end, the mouse-derived amino acid residues QS or A were re-introduced into the hLC.

The features of the resulting mAbs with respect to the binding of soluble antigen and the neutralization of IL2 bioactivity were analyzed by ELISA and CTLL-2 proliferation assay, respectively (see Example 2a above for detailed experimental protocols). In the ELISA experiment, increasing absorbance units are indicative of increased amounts of mAb binding to hIL2 antigen. In the CTLL-2 proliferation assay, increasing fluorescence units are indicative of an increased number of metabolically active (=alive) cells. All cellular SN containing the different mAb versions were controlled for uniform mAb concentrations by an anti-hIgG ELISA before they were subjected to the following experiments. FIG. 5 shows results from a representative experiment. As can clearly be seen, both versions QSPKL+hHc (SEQ ID NO:39) and KAPKA+hHC (SEQ ID NO:13) show comparable binding to hIL2 antigen. The CTLL-2 assay (FIG. 6) shows that QSKPL+hHC OSPKL+hHC does not lead to any detectable neutralization of hIL2 bioactivity because detected fluorescence is not different from the control SN. In contrast, KAPKA+hHC (SEQ ID NO:13) reduces the number of living cells as evident by a mAb concentration dependent reduction in fluorescence. Each data point in the representative experiment shown in FIG. 6 represents the means of duplicate samples. The results of the assays described are summarized in Table 3.

TABLE 3

| light chain | heavy chain | antigen binding | neutralization |
| --- | --- | --- | --- |
| hLC | HHC | + | − |
| hLC_QSPKL | HHC | + | − |
| hLC_KAPKA | HHC | + | + |

This shows that a single amino acid residue located in VL framework 2 defines if the mAb neutralizes IL2 bioactivity: the alanine residue in this position, derived from mouse framework 2, permits neutralization, the leucine residue, derived from human framework 2, does not.

EXAMPLE 3

Determination of the Mode of Neutralization

In the following, the term "Anti-IL2" denotes a humanized anti-IL2 antibody comprising a light chain comprising an amino acid sequence as set out in SEQ ID NO: 9 (itself comprising a VL region with an amino acid sequence as set out in SEQ ID NO: 7) and a heavy chain comprising an amino acid sequence as set out in SEQ ID NO: 10 (itself comprising a VL region with an amino acid sequence as set out in SEQ ID NO: 8). The VL of Anti-IL2 comprises the amino acid sequence "KAPKA" as explained above in Example 2e.2.

It was desired to better understand the mode of neutralization of hIL2 by Anti-IL2. To this end, experiments were performed to study the nature of binding of hIL2 to, on the one hand, components of the hIL2 receptor and, on the other hand, to Anti-IL2.

Since NKL cells require IL2 for survival, it can be inferred that these cells do express a functional receptor for IL2. A FACS experiment was performed according to the procedures detailed above. Briefly, the cells were incubated with a mixture of the anti-hIL2 mAb and a species-specific secondary detection antibody ("premix"). The secondary antibody was conjugated to a fluorescent label. Cellular fluorescence was monitored in the presence and absence of hIL2 using FACS. The following experimental scenarios were carried out to address the question of whether a certain order of incubations was required for the effects observed.

In a first scenario the premix was incubated with or without hIL2 for 30 min, then NKL cells were added. Cellular fluorescence was observed in a hIL2-dependent fashion. In a second scenario NKL cells were incubated with or without hIL2 for 30 min, then the premix was added. Again, cellular fluorescence was observed in a hIL2-dependent fashion.

These experiments demonstrate that hIL2, when bound to Anti-IL2, can still bind to its receptor and further, that hIL2 when associated with its receptor can still interact with Anti-IL2. These results demonstrate that the epitope of hIL2 bound by Anti-IL2 generated as described above is distinct—at least partially—from the epitope of hIL2 bound by the hIL2 receptor. This mode of neutralization is noteworthy in that it implies that neutralization of hIL2 may be accomplished by binding this molecule in either its soluble or its receptor-bound form. Seen chronologically, then, this means that the binding event between hIL2 and Anti-IL-2 may take place either before or following formation of the complex between hIL2 and the hIL2-receptor; in either case, neutralization of the bioactivity of hIL2 is effected. By extrapolation one may therefore assume that neutralization is also effected in the event that the two relevant binding events—formation of the complex between hIL2 and hIL2-receptor and the complex between hIL2 and Anti-IL2—occur simultaneously.

It should be noted that such a mode of neutralization as observed for Anti-IL2 stands in sharp contrast to other known modes of neutralization in which the epitope bound by a neutralizing anti-ligand antibody and a the ligand receptor are one and the same; In such a conventional scenario, it is not possible for the ternary complex between ligand, ligand-receptor and neutralizing anti-ligand antibody to exist. Expressed differently, in such a conventional mode of neutralization, ligand must be bound by neutralizing anti-ligand antibody while the ligand is still in soluble form, and so that formation of a complex between ligand and ligand-receptor is precluded.

EXAMPLE 4

IL2-dependent Binding of Anti-IL2 to the Human Natural Killer Lymphoma Cell Line NKL In this example, the specificity of Anti-IL2 binding to cell surface associated hIL2 was studied. The Anti-IL2 parent Ab (mAb202) showed strictly IL2-dependent binding to the cell surface of NKL cells. This particular feature therefore had to be confirmed for Anti-IL2.

NKL cells were deprived of hIL2 for 24 h prior to the experiment. Anti-IL2 or a human IgG1 isotype control antibody were incubated in the absence or presence of a 2-fold molar excess of hIL2 at 20° C. for 60 min. The respective mixes were then added to NKL cells ($10^5$ cells per sample) and further incubated for 30 min on ice. Subsequently, the cells were washed extensively and a fluorescence-labeled goat anti-human IgG detection antibody was added, followed by incubation for 30 min on ice. Again the cells were washed and then subjected to FACS analysis to study cell-associated fluorescence.

Figure 10:
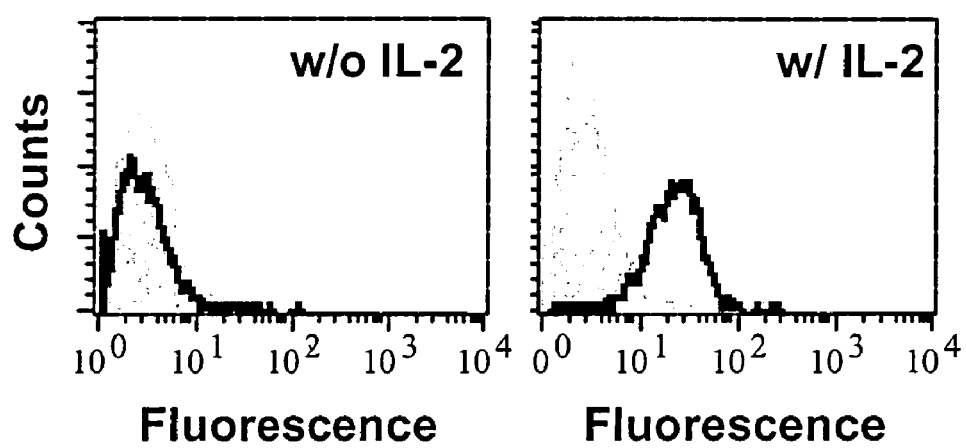

As expected, in the absence of hIL2, no significant cell-associated fluorescence was detectable with either Anti-IL2 or the control antibody (FIG. 10, left plot). In the presence of hIL2, cell associated fluorescence with the control antibody was unchanged (FIG. 10, right plot, shaded peak). In contrast, incubation with hIL2 and Anti-IL2 resulted in a substantial increase in fluorescence (FIG. 10, right plot, black-outlined peak), indicative of specific IL2-dependent binding of Anti-IL2 to the cell surface. Thus, the ability to recognize cell surface-associated hIL2 was conserved in Anti-IL2. This experiment provided evidence that Anti-IL2 not only recognizes hIL2 in solution, but also recognizes hIL2 that is associated with one or several of its receptor components. Consequently, hIL2 can associate with Anti-IL2 and the IL2 receptor component(s) in a non-exclusive fashion.

EXAMPLE 5

Anti-IL2 Abrogates IL2-dependent Up-regulation of CD124 Cell Surface Expression on CTLL-2 Cells Following stimulation with hIL2, CTLL-2 cells proliferate and up-regulate cell surface expression of CD124 (IL-4R alpha) (Puri, R. K., et al. (1990). Immunology 70, 492). Consequently, CTLL-2 cells acquire increased sensitivity to concomitant stimulation through IL-4 via the IL2 stimulus. Therefore, Anti-IL2 may not only limit IL2 mediated proliferation but also affect CD124 expression.

Figure 11:
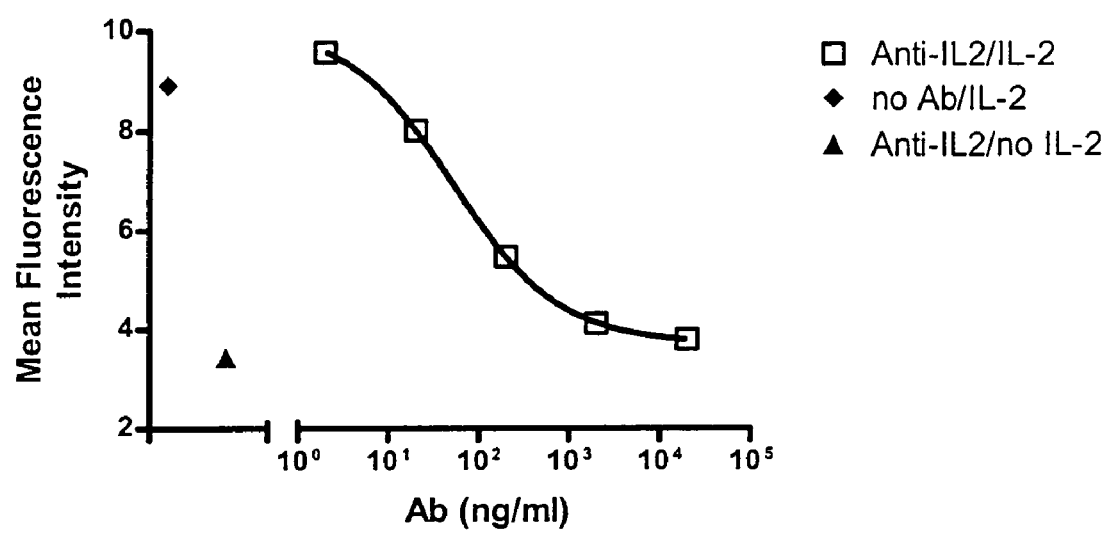

To test this hypothesis, CTLL-2 cells were cultured in the absence of hIL2 for 12 h prior to the experiment and then stimulated with 0.5 ng/ml hIL2 for 5 h in the presence or absence of titrated Anti-IL2 concentrations. CD124 expression levels were assessed by FACS analysis using a fluorescence labeled CD124-specific antibody. The mean fluorescence intensities detected were plotted versus the different Anti-IL2 concentrations (FIG. 11, open squares with black line); mean fluorescence values recorded in the absence of Anti-IL2 (FIG. 11, filled diamond) or in the absence of IL2 (FIG. 11, filled triangle) were included as controls. As evident from FIG. 11, Anti-IL2 reduced CD124 expression in a dose-dependent fashion; the $IC_{50}$ computed from this assay was approximately $3.3 \times 10^{-10}$ M. These data imply that Anti-IL2 not only affects proliferation of CTLL-2 cells but also other IL2-dependent cellular responses, such as CD 124 expression.

EXAMPLE 6

Anti-IL2 Specifically Blocks IL2 Signal Transduction Downstream of the IL2R

This experiment was performed to further rule out the possibility that Anti-IL2 mediates its effects on hIL2-dependent cellular responses in part by some cytotoxic mechanism, and to confirm that the mechanism of Anti-IL2 action is highly specific for hIL2-driven signals but does not affect related pathways. Among the most rapid cellular events of IL2-mediated cellular signals is the tyrosine phosphorylation of the transcription factor STAT3 (Leonard, W. J. 2000. IL2 *Family Cytokines and their Receptors*). Other cytokines, such as IL-6, trigger partially overlapping cellular signalling pathways, which also involve STAT3 (Hemmann, U., et al. (1996). J Biol Chem 271, 12999; Stahl, N., et al. (1995). Science 267, 1349).

Figure 12:
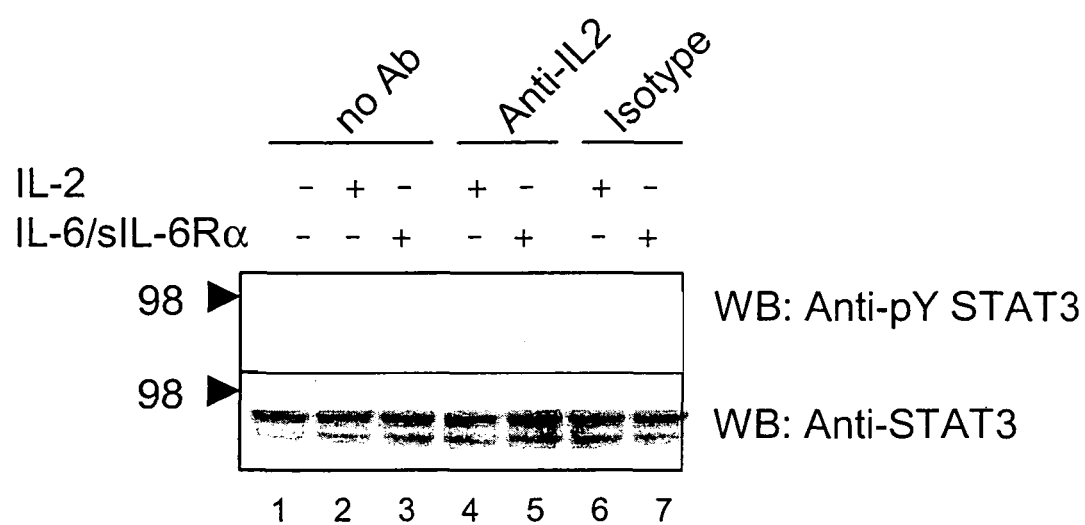

Therefore, Anti-IL2 was tested regarding its effects on IL2- and IL6-driven tyrosine phosphorylation of STAT3. Peripheral blood lymphocytes were isolated from fresh donor blood, incubated at $2 \times 10^6$ cells/ml, prestimulated 48 h with lectin and then allowed to rest in medium for 24 h prior to stimulation. Cells were then stimulated with saturating concentrations of IL2 or IL6/sIL6Rα without mAb or in the presence of Anti-IL2 or an isotype control monoclonal antibody for 15 minutes. Following separation of cytoplasmic extracts by SDS-PAGE, the phosphorylation status of STAT3 was investigated by immune blotting using a STAT3 tyrosine phosphorylation-specific antibody (FIG. 12, upper panel). To control for comparable loading, a blot for total STAT3 protein was also performed (FIG. 12, lower panel). The electrophoretic mobility of standard proteins is indicated on the left of each panel in FIG. 12.

Both IL2 and IL-6 stimulation greatly enhanced cellular tyrosine phosphorylation of STAT3 in the absence of Anti-IL2 (FIG. 12, lanes 2 and 3 versus 1, or lanes 6 and 7 versus 1). Anti-IL2 therefore specifically affects STAT3 tyrosine phosphorylation after IL2 stimulation, but not after IL6 stimulation (FIG. 12, lanes 4 versus 5). These data demonstrate that Anti-IL2 is highly specific for interference with hIL2 biology and does not affect pathways regulated by other factors, nor does Anti-IL2 possess evident cytotoxic effects.

EXAMPLE 7

Figure 13:
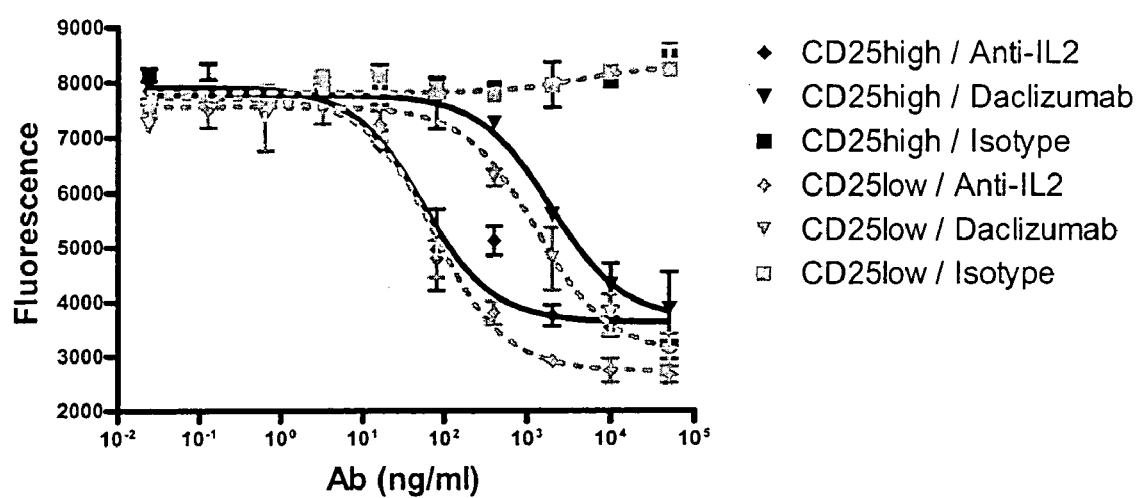

The Efficacy of Anti-IL2 and Daclizumab is Differentially Affected by CD25 Expression Levels The inhibitory activity of Daclizumab, a humanized anti-CD25 mAb, was compared side-by-side to that of Anti-IL2 and an isotype control antibody in a proliferation assay using the IL2-dependent cell line NKL (FIG. 13).

To investigate the effect of CD25 cell surface expression levels on the inhibition of IL2-induced cell proliferation by either Anti-IL2 or Daclizumab, NKL cells were FACS-sorted for low or high level expression of CD25 and both cell populations studied side-by-side in this experiment. The anti-CD25 mAb used for FACS sorting did not interfere with the binding of IL2 or Daclizumab to CD25 (data not shown). Immediately after sorting, a clear distinction of $CD25^{low}$ and $CD25^{high}$ populations was possible by FACS, in the course of the five-day experiment the two populations would converge, leading to CD25 expression levels comparable to the population prior to sorting. This implies that the results obtained in this assay only reflect clearly separated $CD25^{low}$ versus $CD25^{high}$ populations for the initial phase but not for the later phases of this experiment. Therefore, differences to be observed regarding inhibition of proliferation by Anti-IL2 or Daclizumab comparing $CD25^{low}$ and $CD25^{high}$ populations are limited due to non-stable CD25 expression levels; still a clear trend indicating differential CD25 dependence of Daclizumab and Anti-IL2 efficacy can be deduced from these data. The NKL cells were starved for 16 hours in preparation of the experiment by culturing in hIL2-free medium. Per well a final assay volume of 200 µl was applied which included: $1 \times 10^4$ NKL cells, 2 ng/ml hIL2 (to allow for half-maximal proliferation), and the different monoclonal antibodies at titrated concentrations. All samples were prepared in duplicate. Incubation of the respective mixtures took place for 120 hours, then viable cells were visualized using a fluorescent dye.

In general Anti-IL2 was more efficient in neutralization of IL2-mediated proliferation compared to Daclizumab in this assay. As anticipated, the efficacy of Anti-IL2 was not affected by CD25 expression levels: in $CD25^{low}$ and $CD25^{high}$ NKL cells, the curves obtained with Anti-IL2 run essentially on top of one another. In contrast, the curves obtained with Daclizumab show a clear difference in $CD25^{low}$ compared to CD25 NKL cells. The isotype control Ab had no effect (FIG. 13). In summary, this experiment provided in vitro evidence that efficacy of Daclizumab but not Anti-IL2 is dependent on CD25 levels.

EXAMPLE 8

Impact of Anti-IL2 or Daclizumab on IL2-dependent Proliferation of Primary Human NK Cells Not only primary T cells, but also primary NK cells can proliferate in response to IL2 stimulation. Thus, in a further experiment, inhibition of IL2-induced proliferation of freshly isolated human NK cells was studied.

Figure 14:
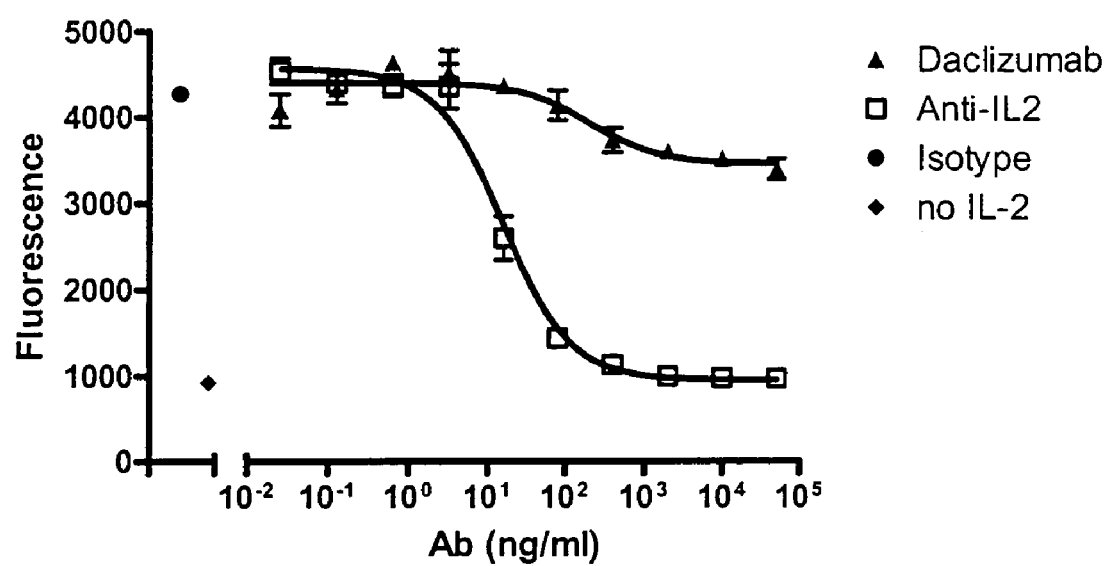

The cells were obtained by negative isolation from donor blood and incubated with hIL2 (5.5 ng/ml) in the presence or absence of titrated Anti-IL2 or Daclizumab. A control antibody was only applied at the highest concentration; another control was performed with cells in the absence of IL2 and antibody. Viable cells were quantified using a fluorescent dye at the end of a one-week incubation period. Anti-IL2 substantially reduced IL2-driven proliferation of primary human NK cells in this experiment. With high Anti-IL2 concentrations, proliferation is essentially limited to the levels observed in the absence of IL2 indicative of Anti-IL2 affecting all IL2-responsive NK cells present in this assay. In contrast, Daclizumab only showed effect of much reduced amplitude, suggesting that only a fraction of NK cells was affected by the presence of this antibody (FIG. 14). To further investigate this finding, the levels of CD25 expression were monitored during the one-week incubation with IL2 and antibodies: only about 11% of total NK cells from the donor shown acquired CD25 expression with a maximum on day 3, and a drop to 2% on day 7. Consistently, freshly isolated NK cells from all donors were devoid of detectable CD25 expression and similar levels and kinetics of CD25 expression were found with NK cells from all donors analyzed (data not shown). This explained why Daclizumab could inhibit proliferation of only a fraction of NK cells (FIG. 14). Anti-IL2 again showed independence of CD25 expression levels and blocked proliferation of all NK cells with an $IC_{50}$ value of approximately $3 \times 10^{-10}$ M. These results provide a strong indication that Anti-IL2 but not Daclizumab is capable of interference with IL2-mediated signals through the intermediate affinity IL2 receptor CD122/CD132, independent of CD25.

EX. 9

Impact of Anti-IL2 or Daelizumab on IL2-dependent Release of IFN-gamma by NK Cells Besides proliferation, a typical and rapid response of primary NK cells to cytokine stimulation is the release of IFN-gamma. The release of the latter was measured in a further experiment, as dependent on both Anti-IL2 and Daclizumab.

Figure 15:
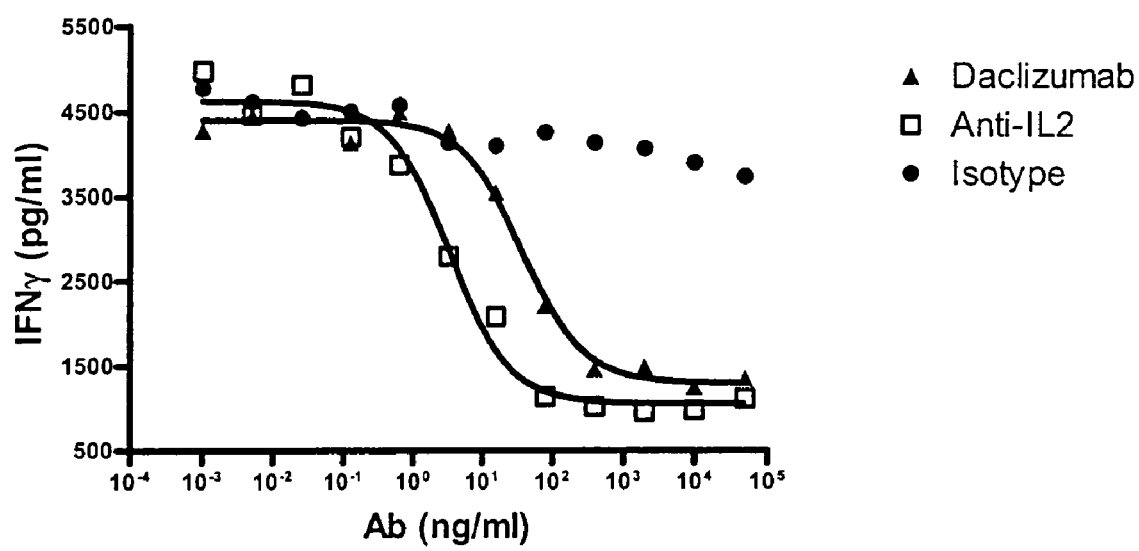

In this assay, freshly isolated human NK cells were stimulated with a cocktail comprising hIL2 (5.5 ng/ml), hIL12 (5 ng/ml) and hIL18 (5 ng/ml), triggering efficient production and release of IFN-gamma by these cells. The effects of titrated Anti-IL2, Daclizumab and an isotype control antibody on IFN-gamma release within the first 48 h of incubation were compared. Both Anti-IL2 and Daclizumab reduced expression of IFN-gamma in a dose-dependent fashion, whereas the control antibody had no effect (FIG. 15). Anti-IL2 was a more potent inhibitor of IFN-gamma release, scoring an $IC_{50}$ of approximately $1.3 \times 10^{-10}$ M, as compared to approximately $1.1 \times 10^{-9}$ M for Daclizumab (FIG. 15). In contrast to the experiment described in the previous example, all NK cells in this experimental setup acquired CD25 expression (data not shown), explaining the more profound effect of Daclizumab on IFN-gamma compared to NK cell proliferation.

Table 4 summarizes the equilibrium binding constant ($K_D$) for Anti-IL2 and Daclizumab. Furthermore, IC50 values obtained in side-by-side comparative experiments with both Abs as described above in Examples 8 and 9.

TABLE 4

| Characteristic | Unit | Anti-IL2 | Daclizumab |
|---|---|---|---|
| Binding Affinity | Equilibrium dissociation constant ($K_D$) | $6.8 \pm 6.1 \times 10^{-10}$ M (BiaCore)<br>$2.5 \pm 1.6 \times 10^{-9}$ M (Cell Surface) | $3.0 \times 10^{-9}$ M[#] |
| Proliferation of Human Primary NK Cells | IC50 | $1.0 \pm 0.6 \times 10^{-10}$ M | $1.4 \pm 0.4 \times 10^{-9}$ M[*] |
| IFN-gamma production by Human NK Cells | IC50 | $1.3 \pm 1.0 \times 10^{-10}$ M | $1.1 \pm 0.8 \times 10^{-9}$ M |

[#]according to Junghans, R. P., et al. (1990). Cancer Res 50, 1495.
[*]based on ~10% of total NK cell population, which expressed CD25

---

The invention claimed is:

1. A humanized monoclonal antibody or fragment thereof which specifically binds to human interleukin-2 (IL2), wherein said humanized monoclonal antibody neutralizes the activity of human IL2 by binding to said human IL2 prior to, during, and/or subsequent to the binding of said human IL2 to the human IL2-receptor, and wherein a light chain variable region of said humanized monoclonal antibody comprises in a second framework region the contiguous amino acid sequence KAPKA (SEQ ID NO: 13).

2. The humanized monoclonal antibody or fragment thereof of claim 1, wherein the contiguous amino acid sequence KAPKA (SEQ ID NO: 13) is located at amino acid positions 42-46 of the second framework region.

3. The humanized monoclonal antibody or fragment thereof of claim 1, wherein at least one of a first, third and/or fourth light chain framework regions correspond(s) to human germline sequence for that/those region(s).

4. The humanized monoclonal antibody or fragment thereof of claim 1, wherein the light chain variable region further comprises in a CDR1 region an amino acid sequence as set out in SEQ ID NO: 1, in a CDR2 region an amino acid sequence as set out in SEQ ID NO: 2 and in a CDR3 region an amino acid sequence as set out in SEQ ID NO: 3; and wherein a heavy chain variable region comprises in a CDR1 region an amino acid sequence as set out in SEQ ID NO: 4, in a CDR2 region an amino acid sequence as set out in SEQ ID NO: 5 and in a CDR:3 region an amino acid sequence as set out in SEQ ID NO: 6.

5. The humanized monoclonal antibody or fragment thereof of claim 1, wherein at least one of a first, third and/or fourth light chain framework regions correspond(s) to the human germline sequence for that/those region(s).

6. The humanized monoclonal antibody or fragment thereof of claim 1, wherein amino acid sequence of the first light chain framework region, remaining amino acid sequences of the second light chain framework region, and amino acid sequence of the third light chain framework region, correspond to any of those of human germline subgroup VKI at loci O12, O2, O18, O8, A30, L1, L15, L4, L18, L5, L19, L8, L23, L9, L11 or L12; or of human germline subgroup VL1 at locus la; or any of those of human germline subgroup VL2 at loci 2c, 2e, 2a2or 2b2.

7. The humanized monoclonal antibody or fragment thereof of claim 1, wherein an amino acid sequence of a first heavy chain framework region, an amino acid sequence of a second heavy chain framework region, and an amino acid sequence of a third heavy chain framework region independently correspond to any of those of human germline subgroup VH3.

8. The humanized monoclonal antibody or fragment thereof of claim 7, wherein an amino acid sequence of a first heavy chain framework region, an amino acid sequence of a second heavy chain framework region, and an amino acid sequence of a third heavy chain framework region are as in locus 3-07 of human germline subgroup VH3.

9. The humanized monoclonal antibody or fragment thereof of claim 6, wherein the amino acid sequence of a fourth light chain framework region corresponds to that of human JK4 (FGGGTKVEIK) (SEQ ID NO: 14).

10. The humanized monoclonal antibody or fragment thereof of claim 1, wherein said humanized monoclonal antibody comprises a light chain variable region comprising an amino acid sequence as set out in SEQ ID NO. 7 and a heavy chain variable region comprising an amino acid sequence as set out in SEQ ID NO. 8.

11. The humanized monoclonal antibody or fragment thereof of claim 1, wherein said humanized monoclonal antibody comprises a light chain comprising an amino acid sequence as set out in SEQ ID NO. 9 and a heavy chain comprising an amino acid sequence as set out in SEQ ID NO. 10.

12. The humanized monoclonal antibody or fragment thereof according to claim 1, wherein said antibody is an IgG.

13. The humanized monoclonal antibody or fragment thereof according to claim 12, wherein said IgG is an IgG1 or Ig04.

14. The humanized monoclonal antibody or fragment thereof according to claim 1, wherein said fragment is an scFv, an Fv, a diabody, a tandem diabody, a Fab, a Fab' or a F(ab)2.

15. The humanized monoclonal antibody or fragment thereof according to claim 14, wherein said fragment is an scFv.

16. The humanized monoclonal antibody or fragment thereof according to claim 15, wherein said scFv comprises an amino acid sequence as set out in SEQ ID NO. 11 or SEQ ID NO. 12.

17. A pharmaceutical composition comprising a humanized monoclonal antibody or fragment thereof according to claim 1.

18. The pharmaceutical composition of claim 17, wherein said pharmaceutical composition further comprises one or more anti-inflammatory or anti-cancer medicaments.

19. The humanized monoclonal antibody or fragment thereof of claim 15, wherein said scFv comprises a light chain variable region having an amino acid sequence as set out in SEQ ID NO. 7 and a heavy chain variable region having an amino acid sequence as set out in SEQ ID NO. 8.

* * * * *

UNITED STATES PATENT AND TRADEMARK OFFICE
CERTIFICATE OF CORRECTION

PATENT NO. : 7,964,707 B2
APPLICATION NO. : 11/916017
DATED : June 21, 2011
INVENTOR(S) : Patrick Bäuerle et al.

Page 1 of 1

It is certified that error appears in the above-identified patent and that said Letters Patent is hereby corrected as shown below:

In title page, item (57) Abstract, lines 2-3, delete "interlukin-2" and insert --interleukin-2-- therefor.

In claim 6, column 137, line 53, delete "VL2at" and insert --VL2 at-- therefor.

In claim 6, column 137, line 53, delete "2a2or" and insert --2a2 or-- therefor.

In claim 13, column 138, line 36, delete "Ig04" and insert --IgG4-- therefor.

Signed and Sealed this
Fourth Day of October, 2011

David J. Kappos
*Director of the United States Patent and Trademark Office*